(12) United States Patent
Kawata et al.

(10) Patent No.: US 8,354,542 B2
(45) Date of Patent: Jan. 15, 2013

(54) HETEROCYCLIC COMPOUND, LIGHT-EMITTING ELEMENT, LIGHT-EMITTING DEVICE, ELECTRONIC DEVICE AND LIGHTING DEVICE

(75) Inventors: Yuko Kawata, Kanagawa (JP); Hiroshi Kadoma, Kanagawa (JP); Harue Osaka, Kanagawa (JP); Nobuharu Ohsawa, Kanagawa (JP); Satoshi Seo, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 65 days.

(21) Appl. No.: 12/972,774

(22) Filed: Dec. 20, 2010

(65) Prior Publication Data

US 2011/0147792 A1 Jun. 23, 2011

(30) Foreign Application Priority Data

Dec. 23, 2009 (JP) ................. 2009-291593

(51) Int. Cl.
*C07D 235/04* (2006.01)
*C07D 405/10* (2006.01)
*B32B 9/00* (2006.01)
*H01J 1/62* (2006.01)
(52) U.S. Cl. .............. 548/305.1; 548/302.7; 548/304.7; 428/690; 428/917; 313/504; 313/506; 315/169.3
(58) Field of Classification Search ............. 548/302.7, 548/304.7, 305.1; 428/690, 917; 313/504, 313/506; 315/169.3
See application file for complete search history.

(56) References Cited

U.S. PATENT DOCUMENTS

| 7,696,348 B2* | 4/2010 | Egawa et al. ................. 544/353 |
| 7,898,171 B2* | 3/2011 | Egawa et al. ................. 313/504 |
| 7,901,791 B2* | 3/2011 | Nakashima et al. .......... 428/690 |
| 7,927,720 B2* | 4/2011 | Nomura et al. ............... 428/690 |
| 2010/0244672 A1 | 9/2010 | Nomura et al. |

FOREIGN PATENT DOCUMENTS

| EP | 10194725 | 7/2009 |
| JP | 2009-158848 | 7/2009 |

OTHER PUBLICATIONS

Nomura, R. et al, "Synthesis of Metal-Carbene Containing Polymers by Polycondensation of a Bifunctional Alkoxycarbene with Diamines," Macromolecules, vol. 33, No. 6, Mar. 1, 2000, pp. 1936-1939.

Search Report re European application No. EP 10194725.7, dated Feb. 10, 2011.

\* cited by examiner

*Primary Examiner* — Golam M M Shameem
(74) *Attorney, Agent, or Firm* — Husch Blackwell LLP

(57) ABSTRACT

Objects of the present invention are to provide the following: a novel heterocyclic compound which can be used as a material in which a light-emitting substance of a light-emitting layer in a light-emitting element is dispersed; a novel heterocyclic compound having a high electron-transport property; a light-emitting element having high current efficiency; and a light-emitting device, an electronic device and a lighting device each having reduced power consumption. Provided are a heterocyclic compound represented by General Formula (G1-1) or (G1-2) below, and a light-emitting element, a light-emitting device, an electronic device and a lighting device each including the heterocyclic compound. Such use of the heterocyclic compound represented by General Formula (G1-1) or (G1-2) makes it possible to provide a light-emitting element having high current efficiency, and a light-emitting device, an electronic device and a lighting device each having reduced power consumption.

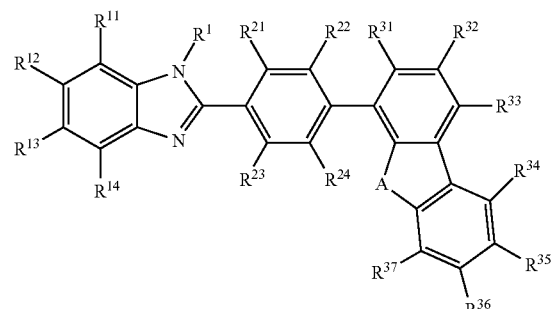

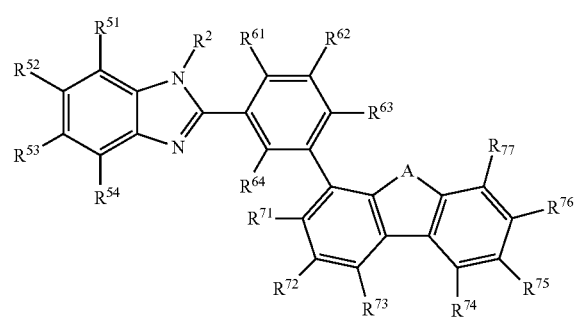

15 Claims, 36 Drawing Sheets

HETEROCYCLIC COMPOUND, LIGHT-EMITTING ELEMENT, LIGHT-EMITTING DEVICE, ELECTRONIC DEVICE AND LIGHTING DEVICE

BACKGROUND OF THE INVENTION

1. Field of the Invention

The present invention relates to a heterocyclic compound. The present invention also relates to a light-emitting element, a light-emitting device, an electronic device, and a lighting device each using the heterocyclic compound.

2. Description of the Related Art

In recent years, research and development have been extensively conducted on light-emitting elements using electroluminescence (EL). In the basic structure of such a light-emitting element, a layer which contains a light-emitting substance is interposed between a pair of electrodes. By voltage application to this element, light emission from the light-emitting substance can be obtained.

Since such light-emitting elements are self-luminous elements, they have advantages over liquid crystal displays in having high pixel visibility and eliminating the need for a backlight, for example, thereby being considered as suitable for flat panel display elements. Light-emitting elements are also highly advantageous in that they can be thin and lightweight. Furthermore, very high speed response is one of the features of such elements.

Furthermore, since such light-emitting elements can be formed in a film form, they make it possible to provide planar light emission. An element having a large area can thus be formed. This is difficult to obtain with point light sources typified by incandescent lamps and LEDs or linear light sources typified by fluorescent lamps. Thus, light-emitting elements have great potential as planar light sources applicable to lightings and the like.

Light-emitting elements using electroluminescence can be broadly classified according to whether they use an organic compound or an inorganic compound as a light-emitting substance. In the case where an organic compound is used as the light-emitting substance, application of a voltage to a light-emitting element causes injection of electrons and holes into a layer that includes the organic compound having a light-emitting property from a pair of electrodes, and thus a current flows. Then, carriers (electrons and holes) recombine, thereby forming the excited state of the organic compound having a light-emitting property. When the excited state is changed to the ground state, light is emitted.

The excited state generated by an organic compound can be a singlet excited state or a triplet excited state. Luminescence from the singlet excited state (S*) is referred to as fluorescence, and luminescence from the triplet excited state (T*) is referred to as phosphorescence. In addition, the statistical generation ratio thereof in a light-emitting element is considered to be as follows: S*:T*=1:3.

With a compound that can convert energy of a singlet excited state into light emission (hereinafter, called a fluorescent compound), only light emission from the singlet excited state (fluorescence) is observed and that from the triplet excited state (phosphorescence) is not observed, at room temperature. Therefore the internal quantum efficiency (the ratio of generated photons to injected carriers) of a light-emitting element using a fluorescent compound is assumed to have a theoretical limit of 25% based on the ratio, S*:T*=1:3.

In contrast, with a compound that can convert energy of a triplet excited state into light emission (hereinafter, called a phosphorescent compound), light emission from the triplet excited state (phosphorescence) is observed. Further, with a phosphorescent compound, since intersystem crossing (i.e., transition from a singlet excited state to a triplet excited state) easily occurs, the internal quantum efficiency can be increased to 75% to 100% in theory. In other words, the emission efficiency can be 3 to 4 times as much as that of an element using a fluorescent compound. For this reason, light-emitting elements using phosphorescence compounds are now under active development in order to realize light-emitting elements having higher efficiency (e.g., see Patent Document 1).

When a light-emitting layer of a light-emitting element is formed using a phosphorescent compound described above, in order to suppress concentration quenching or quenching due to triplet-triplet annihilation in the phosphorescent compound, the light-emitting layer is often formed such that the phosphorescent compound is dispersed in a matrix of another compound. Here, the compound serving as the matrix is called a host material, and the compound dispersed in the matrix, such as a phosphorescent compound, is called a guest material.

In the case where a phosphorescent compound is a guest material, a host material needs to have higher triplet excitation energy (energy difference between the ground state and the triplet excited state) than the phosphorescent compound.

Furthermore, since the singlet excitation energy (energy difference between the ground state and the singlet excited state) is higher than the triplet excitation energy, a material that has high triplet excitation energy also has high singlet excitation energy. Therefore the above substance that has high triplet excitation energy is also effective in a light-emitting element using a fluorescent compound as a light-emitting substance.

In addition, a light-emitting element having high current efficiency is expected to realize a light-emitting device, an electronic device, and a lighting device each having low power consumption.

REFERENCE

[Patent Document 1] Japanese Published Patent Application No. 2009-158848

SUMMARY OF THE INVENTION

An object of one embodiment of the present invention is to provide a novel heterocyclic compound which can be used as a host material in which a light-emitting substance of a light-emitting layer in a light-emitting element is dispersed. Another object of one embodiment of the present invention is to provide a novel heterocyclic compound having a high electron-transport property. Yet another object of one embodiment of the present invention is to provide a light-emitting element having high current efficiency. Still another object of one embodiment of the present invention is to provide a light-emitting device, an electronic device, and a lighting device each having reduced power consumption by use of the above light-emitting element.

One embodiment of the present invention is a heterocyclic compound having a structure represented by General Formula (G1-1) below.

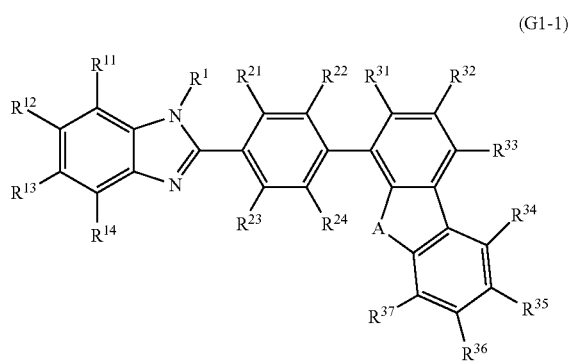

(G1-1)

In General Formula (G1-1), A represents oxygen or sulfur, $R^1$ represents an alkyl group having 1 to 4 carbon atoms or a substituted or unsubstituted aryl group having 6 to 13 carbon atoms, and $R^{11}$ to $R^{14}$, $R^{21}$ to $R^{24}$, and $R^{31}$ to $R^{37}$ separately represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by General Formula (G2-1) below.

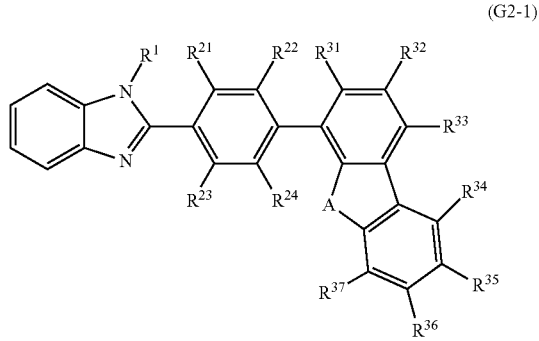

(G2-1)

In General Formula (G2-1), A represents oxygen or sulfur, $R^1$ represents an alkyl group having 1 to 4 carbon atoms or a substituted or unsubstituted aryl group having 6 to 13 carbon atoms, and $R^{21}$ to $R^{24}$ and $R^{31}$ to $R^{37}$ separately represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by General Formula (G2-1) below.

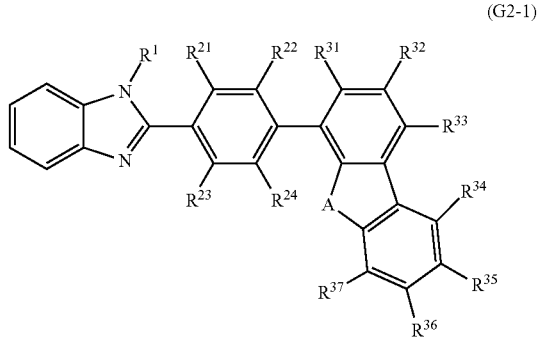

(G2-1)

In General Formula (G2-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $R^{31}$ to $R^{37}$ separately represent hydrogen or a substituted or unsubstituted aryl group having 6 to 13 carbon atoms.

Another embodiment of the present invention is a heterocyclic compound having a structure represented by General Formula (G2-1) below.

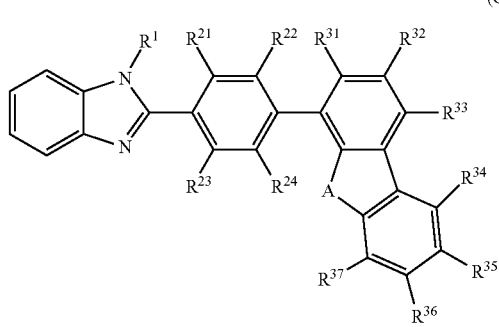

(G2-1)

In General Formula (G2-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $R^{31}$ to $R^{37}$ separately represent hydrogen or a substituted or unsubstituted aryl group having 6 to 13 carbon atoms. At least one of $R^{31}$ to $R^{37}$ represents a substituted or unsubstituted aryl group having 6 to 13 carbon atoms.

Yet another embodiment of the present invention is a heterocyclic compound having a structure represented by General Formula (G3-1) below.

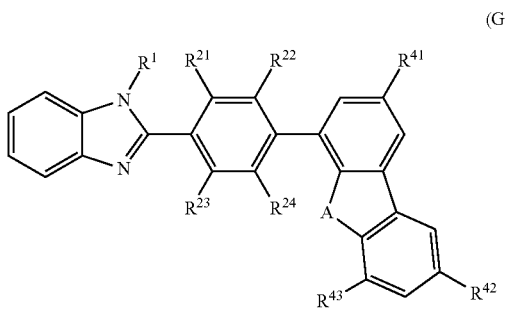

(G3-1)

In General Formula (G3-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $R^{41}$ to $R^{43}$ separately represent hydrogen or a substituted or unsubstituted aryl group having 6 to 13 carbon atoms. At least one of $R^{41}$ to $R^{43}$ represents a substituted or unsubstituted aryl group having 6 to 13 carbon atoms.

Another embodiment of the present invention is a heterocyclic compound having a structure represented by General Formula (G4-1) below.

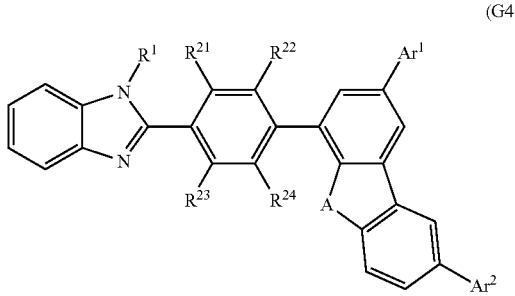

(G4-1)

In General Formula (G4-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $Ar^1$ and $Ar^2$ separately represent a substituted or unsubstituted aryl group having 6 to 13 carbon atoms.

One embodiment of the present invention is a heterocyclic compound having a structure represented by General Formula (G1-2) below.

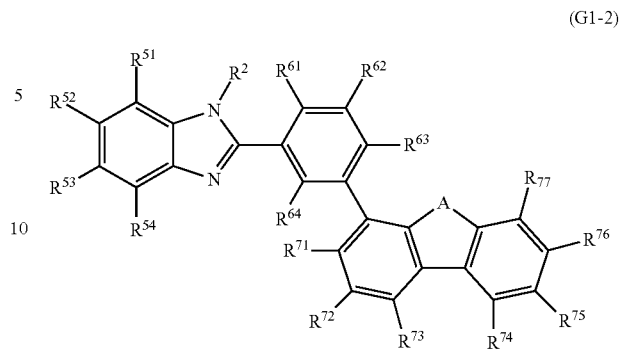

(G1-2)

In General Formula (G1-2), A represents oxygen or sulfur, $R^2$ represents an alkyl group having 1 to 4 carbon atoms or a substituted or unsubstituted aryl group having 6 to 13 carbon atoms, and $R^{51}$ to $R^{54}$, $R^{61}$ to $R^{64}$, and $R^{71}$ to $R^{77}$ separately represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by General Formula (G2-2) below.

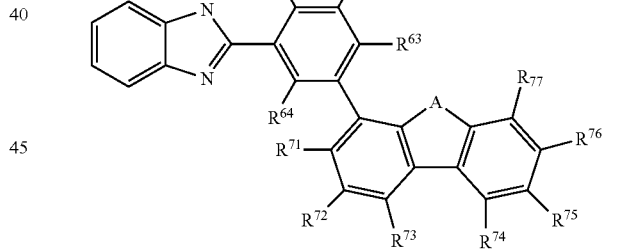

(G2-2)

In General Formula (G2-2), A represents oxygen or sulfur, $R^2$ represents an alkyl group having 1 to 4 carbon atoms or a substituted or unsubstituted aryl group having 6 to 13 carbon atoms, and $R^{61}$ to $R^{64}$ and $R^{71}$ to $R^{77}$ separately represent any of hydrogen, an alkyl group having 1 to 4 carbon atoms, and a substituted or unsubstituted aryl group having 6 to 13 carbon atoms.

Another embodiment of the present invention is a heterocyclic compound having a structure represented by General Formula (G2-2) below.

(G2-2)

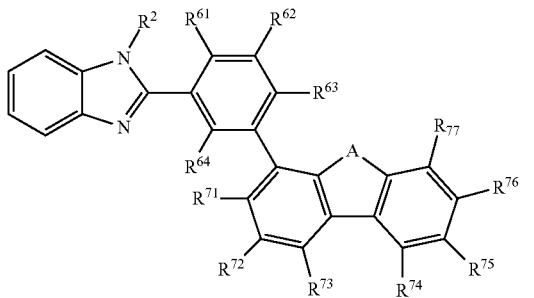

In General Formula (G2-2), A represents oxygen or sulfur, $R^2$ represents an alkyl group having 1 to 4 carbon atoms or a substituted or unsubstituted aryl group having 6 to 13 carbon atoms, $R^{61}$ to $R^{64}$ separately represent any of hydrogen, an alkyl group having 1 to 4 carbon atoms, and a substituted or unsubstituted aryl group having 6 to 13 carbon atoms, and $R^{71}$ to $R^{77}$ separately represent hydrogen or a substituted or unsubstituted aryl group having 6 to 13 carbon atoms.

The heterocyclic compound of one embodiment of the present invention which is represented by any of General Formulae (G1-1) to (G4-1) and (G2-1) and (G2-2) described above can be preferably used as a material for a light-emitting element or an organic device such as an organic transistor. Thus, one embodiment of the present invention is a light-emitting element including the heterocyclic compound described above.

The heterocyclic compound of one embodiment of the present invention has a wide energy gap. Therefore the current efficiency of a light-emitting element can be high when such a heterocyclic compound is used as a host material in which a light-emitting substance of a light-emitting layer is dispersed. In particular, the heterocyclic compound of one embodiment of the present invention can be used as a host material in which a light-emitting substance that emits fluorescence in the visible light region or a light-emitting substance that emits red to green phosphorescence is dispersed, whereby a light-emitting element having high current efficiency can be obtained. Thus, another embodiment of the present invention is a light-emitting element having a light-emitting layer that includes the heterocyclic compound described above and a light-emitting substance.

Further, since the heterocyclic compound of one embodiment of the present invention has a high electron-transport property, the heterocyclic compound can be preferably used as a material for an electron-transport layer in a light-emitting element. Another embodiment of the present invention is thus a light-emitting element having at least a light-emitting layer and an electron-transport layer between a pair of electrodes, in which the electron-transport layer includes the heterocyclic compound described above.

Since the light-emitting element of one embodiment of the present invention which is obtained as above can have low drive voltage and high current efficiency, a light-emitting device (such as an image display device) using this light-emitting element can realize low power consumption. Thus, one embodiment of the present invention is a light-emitting device including the above light-emitting element. In addition, an electronic device and a lighting device each including the light-emitting device are also embodiments of the present invention.

The light-emitting device in this specification covers an image display device using a light-emitting element and also the following devices: a module including a light-emitting element to which a connector such as an anisotropic conductive film, a tape automated bonding (TAB) tape, or a tape carrier package (TCP) is attached; a module in which the top of the TAB tape or the TCP is provided with a printed wiring board; a module in which an integrated circuit (IC) is directly mounted on a light-emitting element by a chip on glass (COG) technique; and the like. Furthermore, a light-emitting device used in a lighting device and the like is also included.

One embodiment of the present invention can provide a novel heterocyclic compound which can be used as a host material in which a light-emitting substance of a light-emitting layer in a light-emitting element is dispersed. Another embodiment of the present invention can provide a novel heterocyclic compound which has a high electron-transport property. Further, by using the heterocyclic compound of one embodiment of the present invention, the light-emitting element can have high current efficiency. Furthermore, by using this light-emitting element, a light-emitting device, an electronic device, and a lighting device each having reduced power consumption can be provided according to one embodiment of the present invention.

DETAILED DESCRIPTION OF THE INVENTION

Figure 1A:
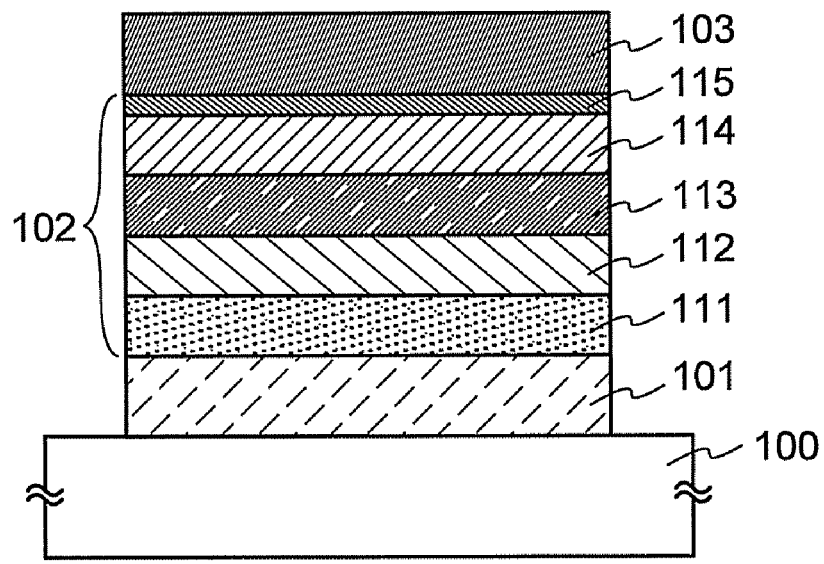
FIGS. 1A and 1B each illustrate a light-emitting element of one embodiment of the present invention.

Embodiments of the present invention will now be described with reference to the accompanying drawings. Note that the invention is not limited to the description below, and it will be easily understood by those skilled in the art that various changes and modifications can be made without departing from the spirit and scope of the invention. Therefore, the invention should not be construed as being limited to the description in the following Embodiments and Examples.

Embodiment 1

In Embodiment 1, a heterocyclic compound of one embodiment of the present invention will be described.

One embodiment of the present invention is the heterocyclic compound represented by General Formula (G1-1).

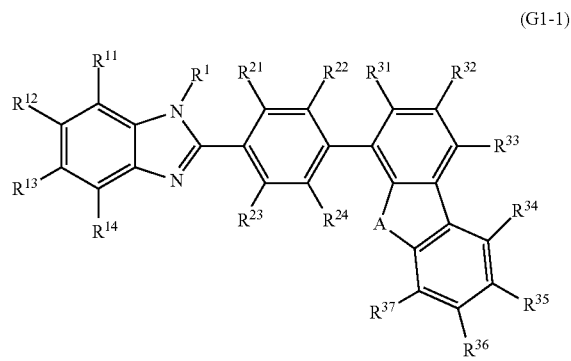

(G1-1)

In General Formula (G1-1), A represents oxygen or sulfur, $R^1$ represents an alkyl group having 1 to 4 carbon atoms or a substituted or unsubstituted aryl group having 6 to 13 carbon atoms, and $R^{11}$ to $R^{14}$, $R^{21}$ to $R^{24}$, and $R^{31}$ to $R^{37}$ separately represent any of hydrogen, an alkyl group having 1 to 4 carbon atoms, and a substituted or unsubstituted aryl group having 6 to 13 carbon atoms. Note that the carbon atoms in an aryl group in this specification mean carbon atoms which form a ring of the main skeleton, not including carbon atoms in a substituent bonded to the main skeleton.

Preferred is a heterocyclic compound (G2-1) of one embodiment of the present invention in which $R^{11}$ to $R^{14}$ are each substituted with hydrogen in General Formula (G1-1), because a material for this heterocyclic compound is readily available and such a heterocyclic compound is easy to synthesize.

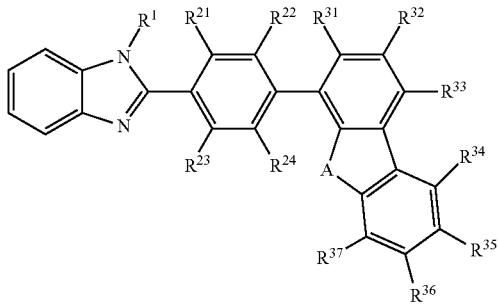

(G2-1)

In General Formula (G2-1), A represents oxygen or sulfur, $R^1$ represents an alkyl group having 1 to 4 carbon atoms or a substituted or unsubstituted aryl group having 6 to 13 carbon atoms, and $R^{21}$ to $R^{24}$ and $R^{31}$ to $R^{37}$ separately represent any of hydrogen, an alkyl group having 1 to 4 carbon atoms, and a substituted or unsubstituted aryl group having 6 to 13 carbon atoms.

Another embodiment of the present invention is the heterocyclic compound having the structure represented by General Formula (G2-1) below.

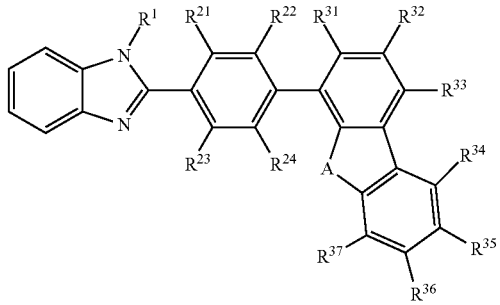

(G2-1)

In General Formula (G2-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $R^{31}$ to $R^{37}$ separately represent hydrogen or a substituted or unsubstituted aryl group having 6 to 13 carbon atoms. At least one of $R^{31}$ to $R^{37}$ represents a substituted or unsubstituted aryl group having 6 to 13 carbon atoms.

Yet another embodiment of the present invention is the heterocyclic compound having the structure represented by General Formula (G3-1) below.

(G2-1)

In General Formula (G2-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $R^{31}$ to $R^{37}$ separately represent hydrogen or a substituted or unsubstituted aryl group having 6 to 13 carbon atoms.

Another embodiment of the present invention is the heterocyclic compound having the structure represented by General Formula (G2-1) below.

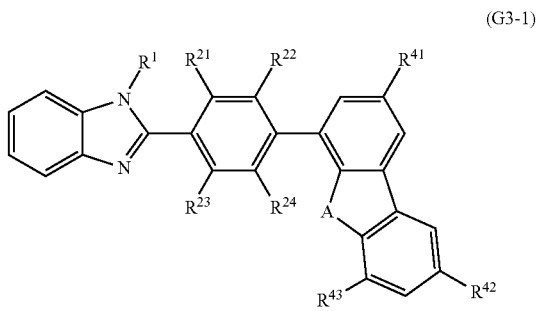

(G3-1)

In General Formula (G3-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $R^{41}$ to $R^{43}$ separately represent hydrogen or a substituted or unsubstituted aryl group having 6 to 13 carbon atoms. At least one of $R^{41}$ to $R^{43}$ represents a substituted or unsubstituted aryl group having 6 to 13 carbon atoms.

Still another embodiment of the present invention is the heterocyclic compound having the structure represented by General Formula (G4-1) below.

(G4-1)

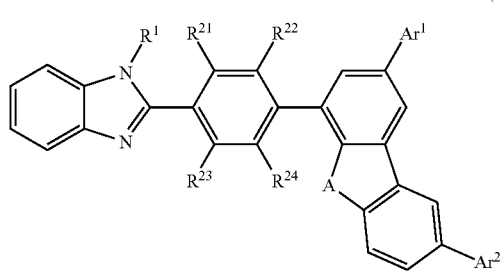

In General Formula (G4-1), A represents oxygen or sulfur, $R^1$ represents an alkyl group having 1 to 4 carbon atoms or a substituted or unsubstituted aryl group having 6 to 13 carbon atoms, $R^{21}$ to $R^{24}$ separately represent any of hydrogen, an alkyl group having 1 to 4 carbon atoms, and a substituted or unsubstituted aryl group having 6 to 13 carbon atoms, and $Ar^1$ and $Ar^2$ separately represent a substituted or unsubstituted aryl group having 6 to 13 carbon atoms.

As specific structures of $R^1$ in General Formulae (G1-1) to (G4-1), there are substituents represented by Structural Formulae (1-1) to (1-22).

(1-1)

CH₃

(1-2)

H₃C—CH₂

(1-3)

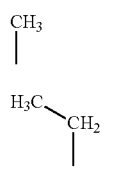

(1-4)

H₃C—CH—CH₃

(1-5)

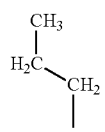

(1-6)

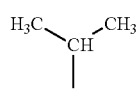

(1-7)

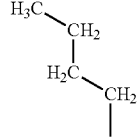

(1-8)

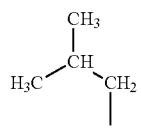

(1-9)

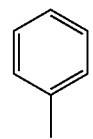

(1-10)

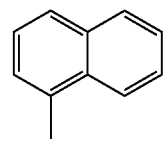

(1-11)

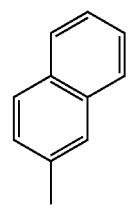

(1-12)

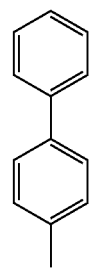

(1-13)

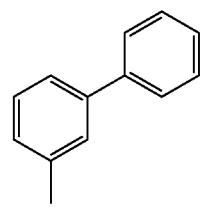

(1-14)

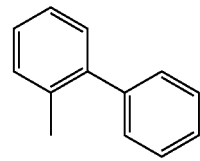

(1-15)

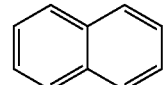

(1-16) 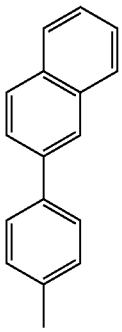

(1-17) 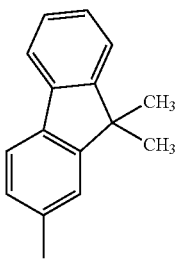

(1-18) 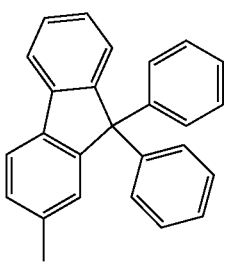

(1-19) 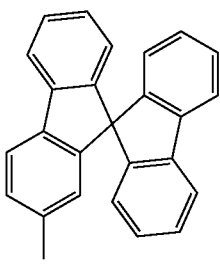

(1-20) 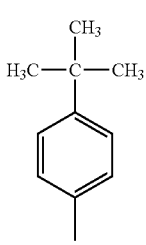

(1-21) 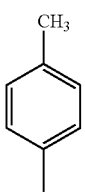

(1-22) 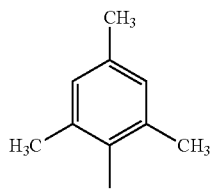

As specific structures of $R^{11}$ to $R^{14}$, $R^{21}$ to $R^{24}$, and $R^{31}$ to $R^{37}$ in General Formula (G1-1), there are substituents represented by Structural Formula (2-1) in addition to Structural Formulae (1-1) to (1-22) illustrated above.

(2-1) 

As specific structures of $R^{21}$ to $R^{24}$ and $R^{31}$ to $R^{37}$ in General Formula (G2-1), there are substituents represented by the above-described Structural Formulae (1-1) to (1-22) and (2-1) illustrated above.

As specific structures of $R^{21}$ to $R^{24}$ in General Formulae (G3-1) and (G4-1), there are substituents represented by Structural Formulae (1-1) to (1-22) and (2-1) illustrated above.

As specific structures of $R^{41}$ to $R^{43}$ in General Formula (G3-1), there are substituents represented by Structural Formulae (1-9) to (1-22) and (2-1) illustrated above.

Further, as specific structures of $Ar^1$ and $Ar^2$ in General Formula (G4-1), there are substituents represented by Structural Formulae (1-9) to (1-22) illustrated above.

Specific examples of the heterocyclic compound represented by General Formula (G1-1) include, but are not limited to, heterocyclic compounds represented by Structural Formulae (100) to (219).

(100) 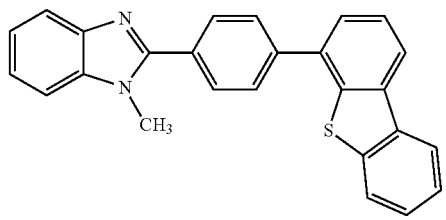

(101) 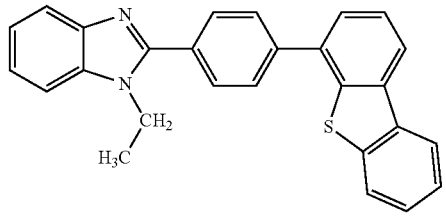

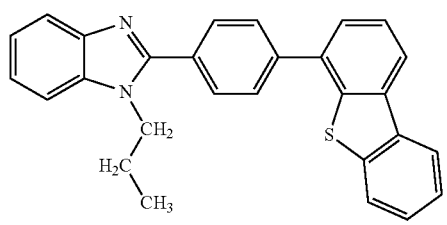
(102)
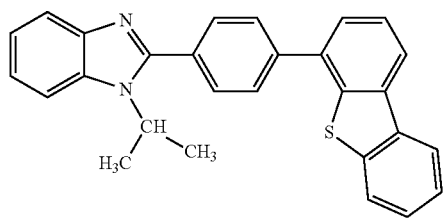
(103)
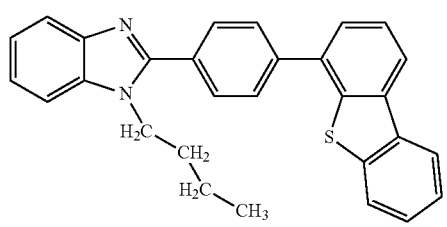
(104)
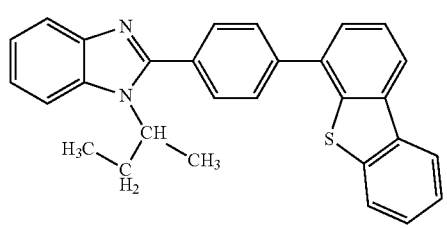
(105)
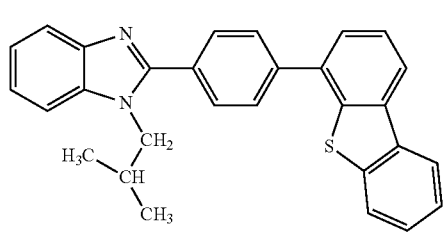
(106)
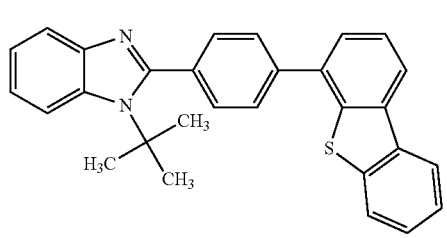
(107)
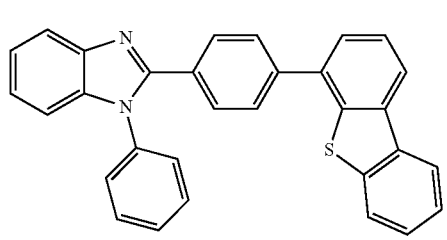
(108)
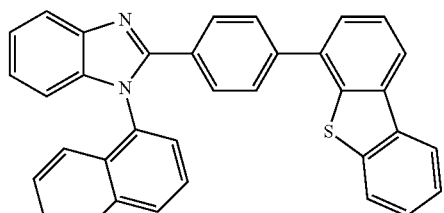
(109)
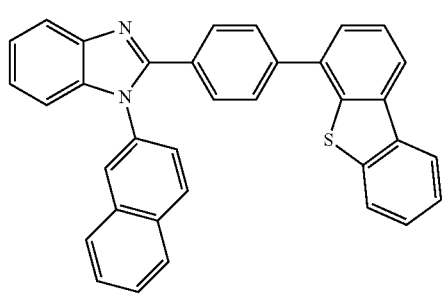
(110)
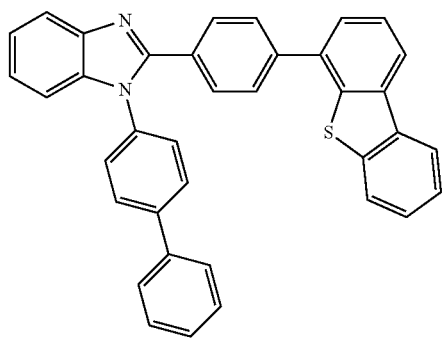
(111)
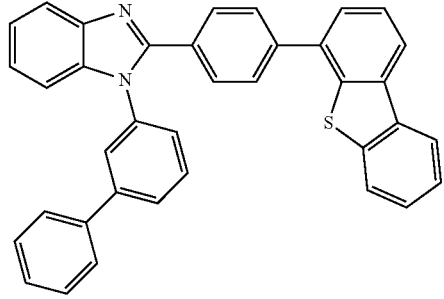
(112)
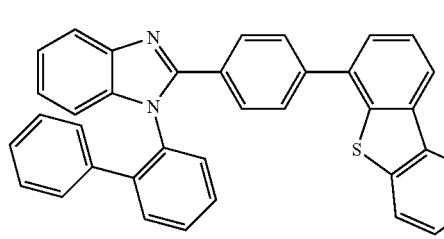
(113)

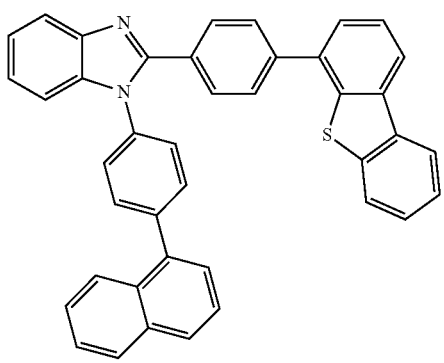
(114)
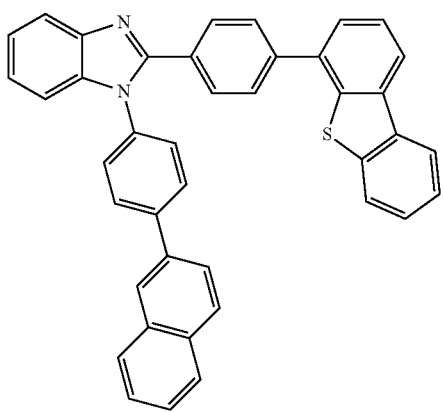
(115)
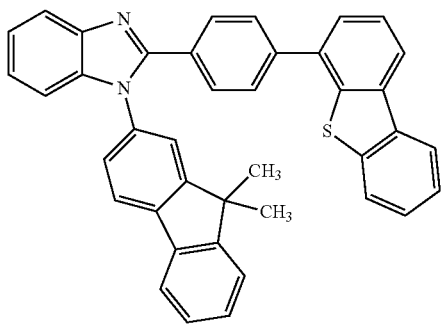
(116)
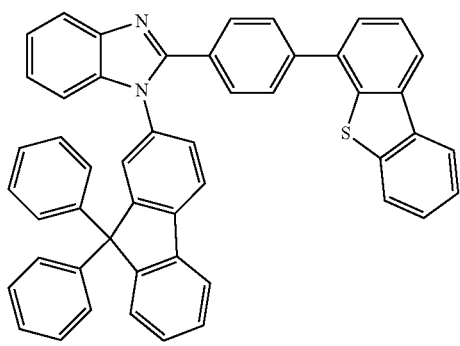
(117)
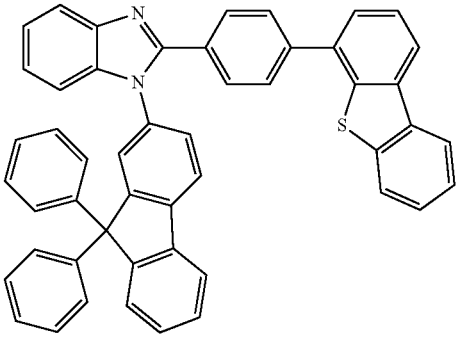
(118)
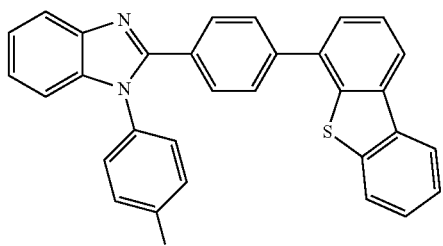
(119)
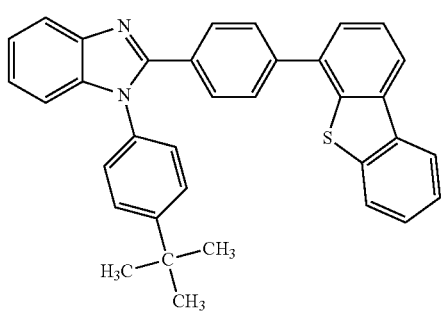
(120)
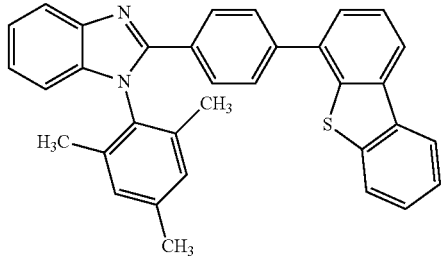
(121)
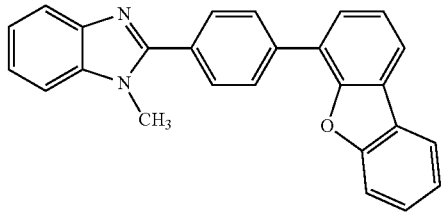
(122)
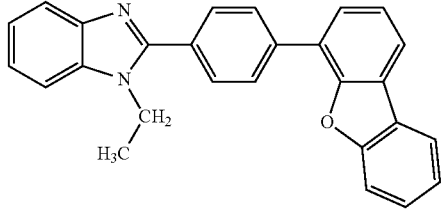
(123)

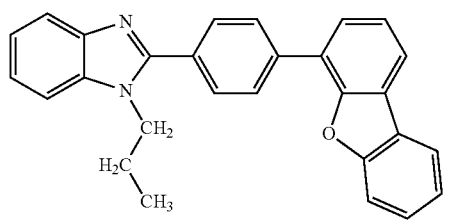 (124)
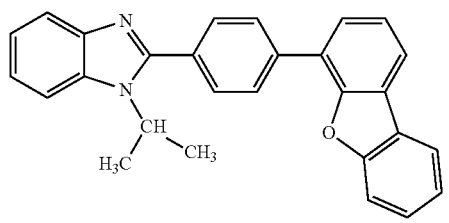 (125)
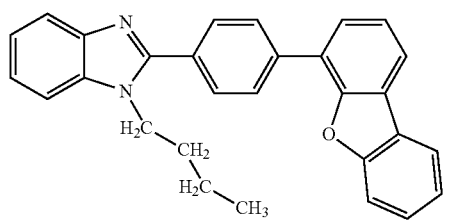 (126)
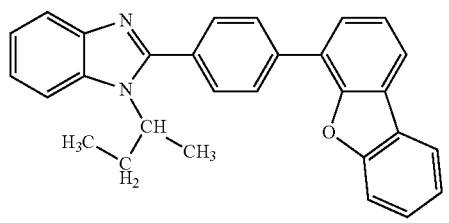 (127)
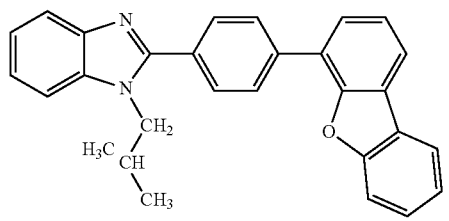 (128)
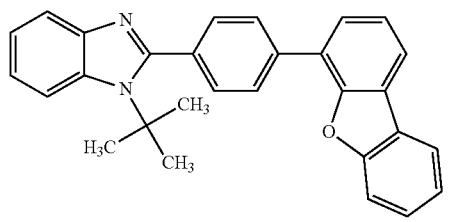 (129)
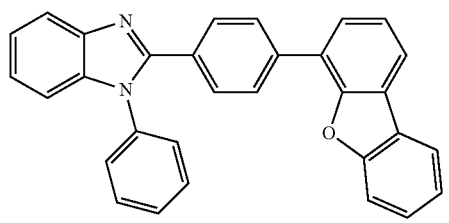 (130)
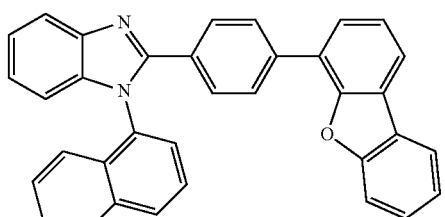 (131)
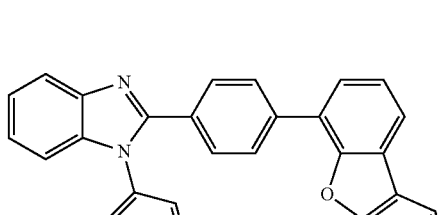 (132)
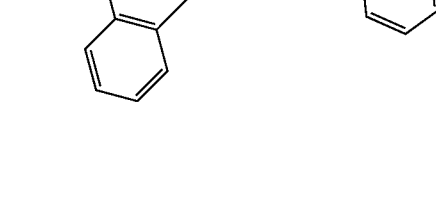 (133)
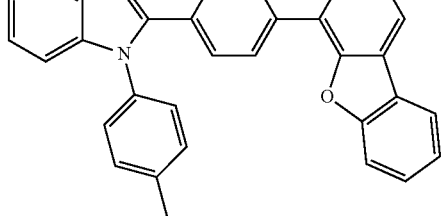 (134)
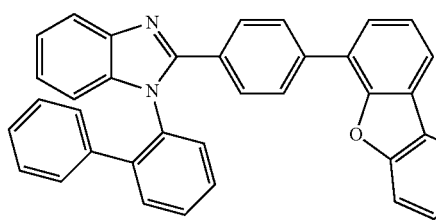 (135)

(136) 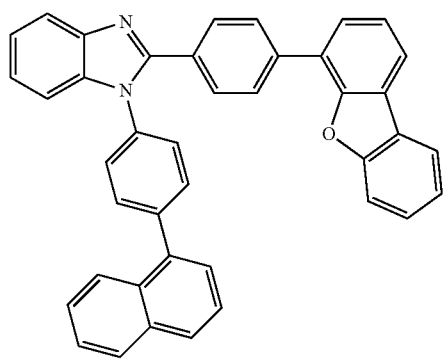
(137) 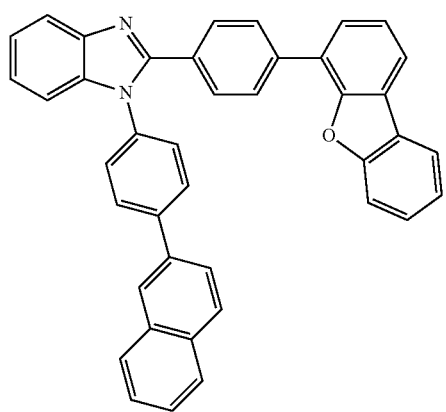
(138) 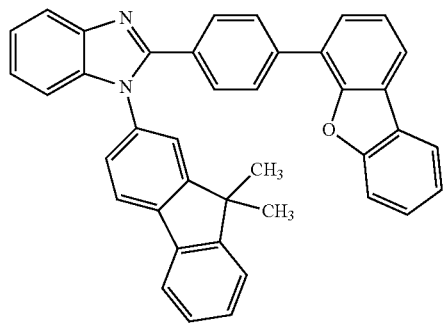
(139) 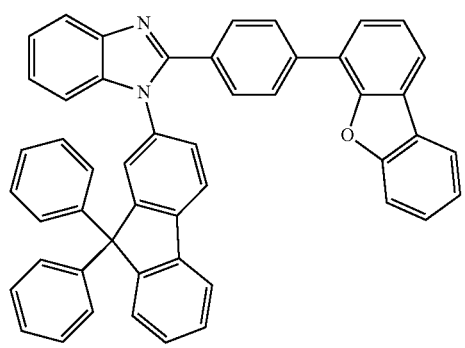
(140) 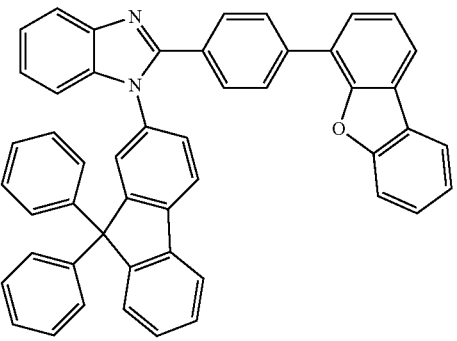
(141) 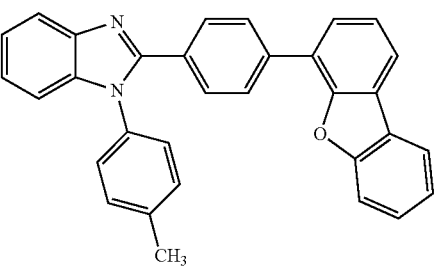
(142) 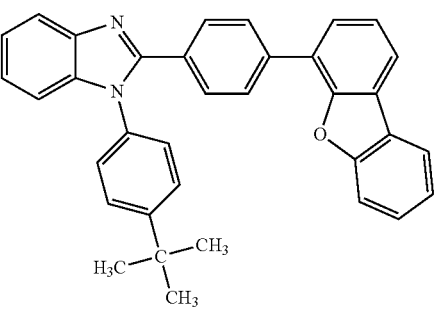
(143) 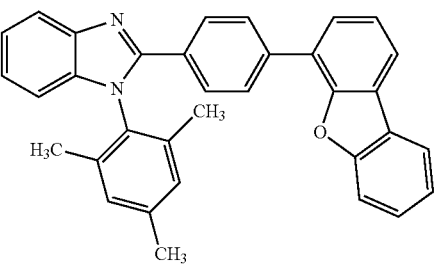
(144) 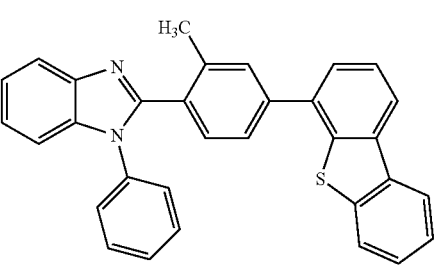

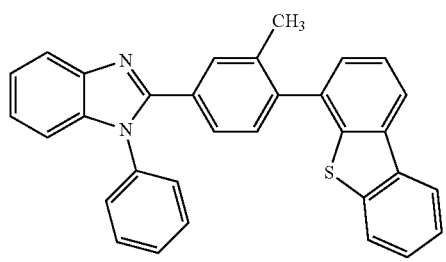
(145)
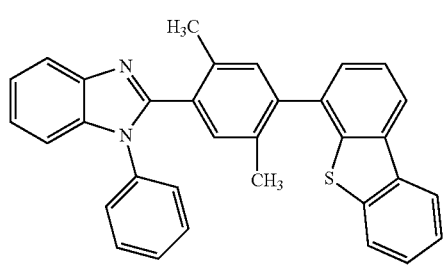
(146)
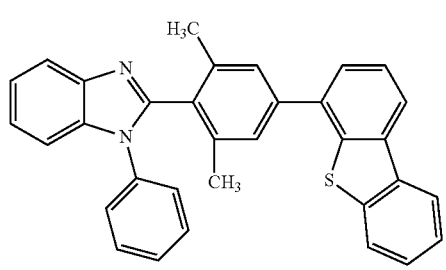
(147)
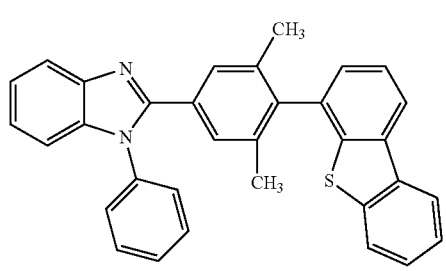
(148)
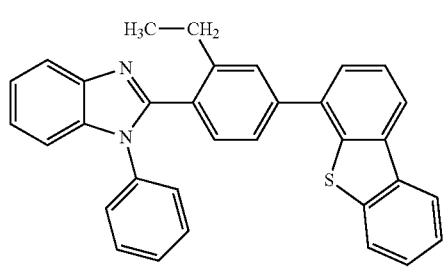
(149)
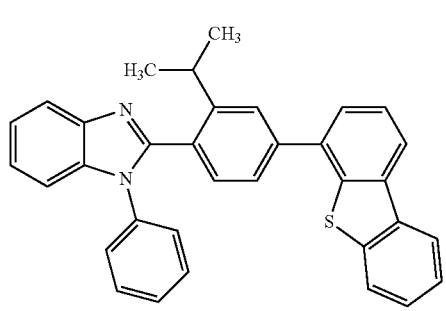
(150)
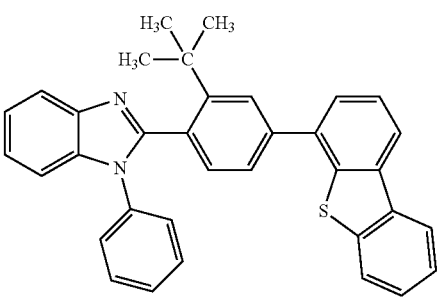
(151)
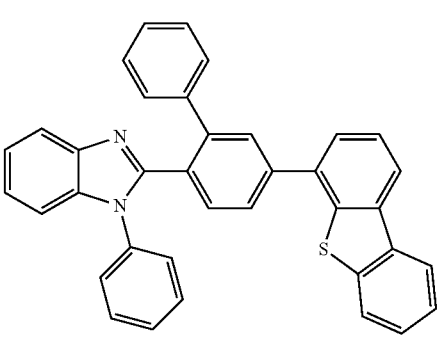
(152)
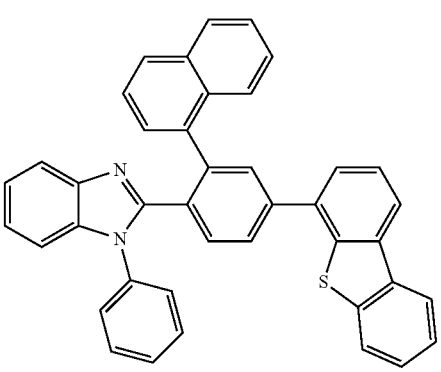
(153)
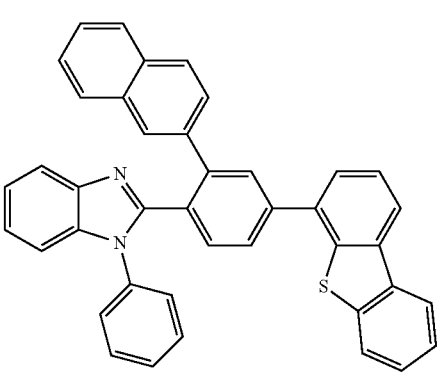
(154)

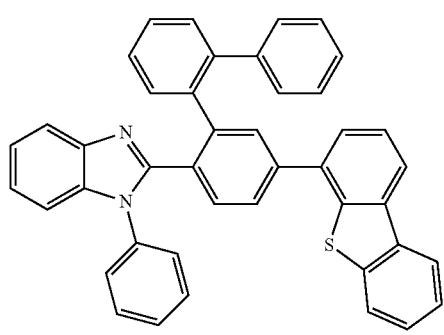
(155)
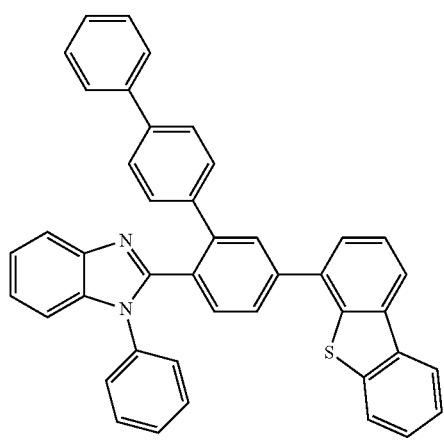
(156)
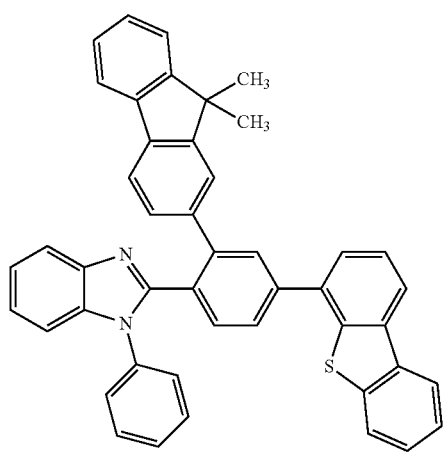
(157)
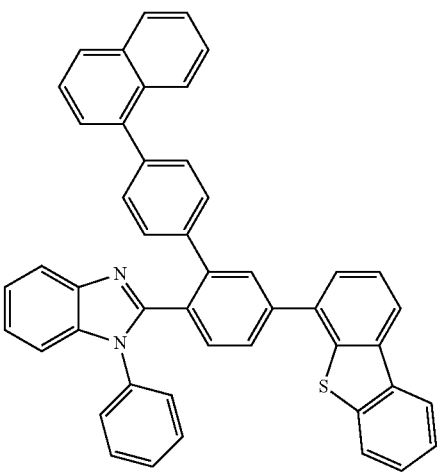
(158)
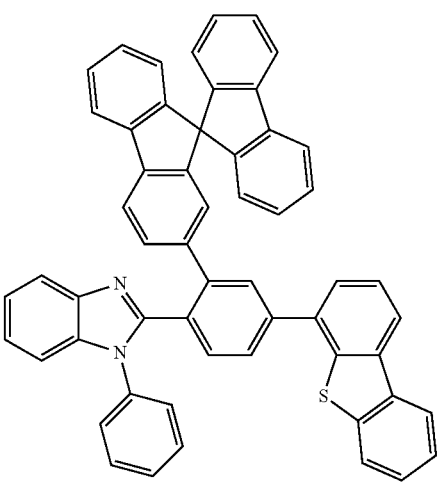
(159)
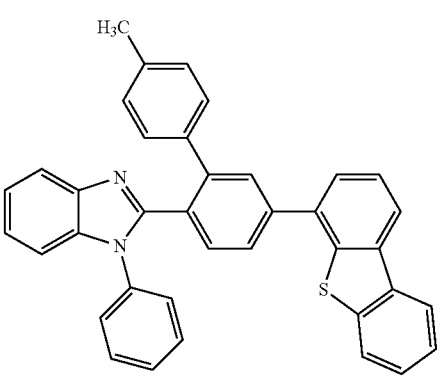
(160)

-continued
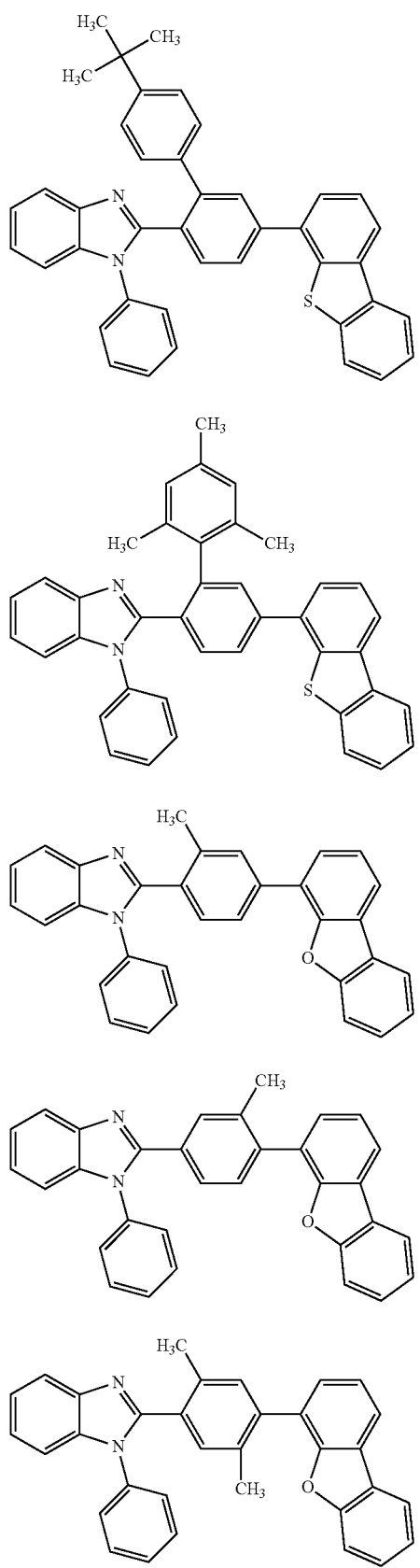
(161)
(162)
(163)
(164)
(165)
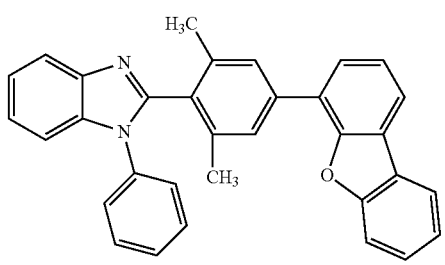
(166)
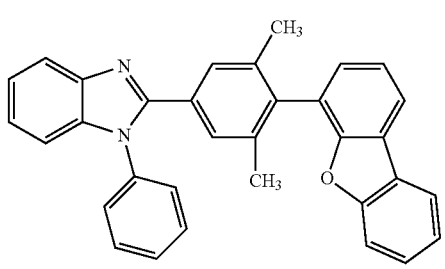
(167)
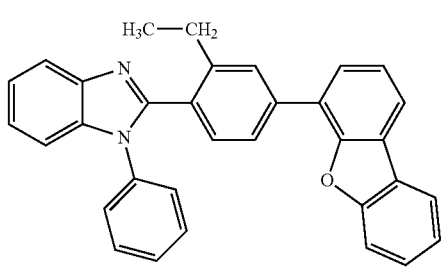
(168)
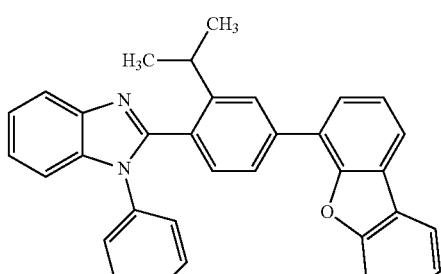
(169)
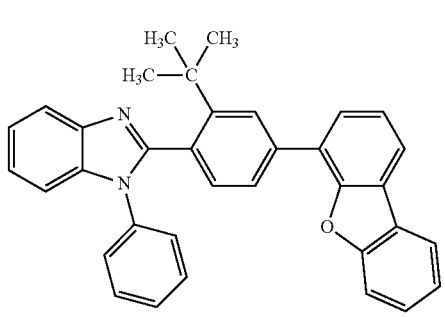
(170)

(171)
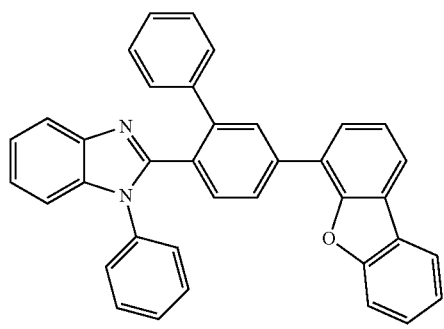
(172)
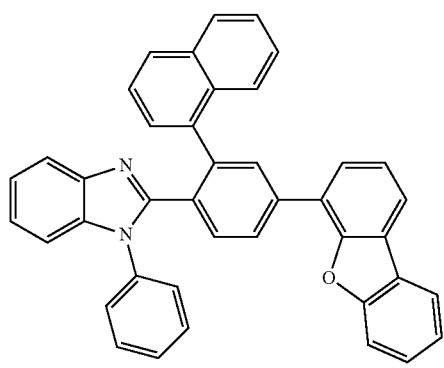
(173)
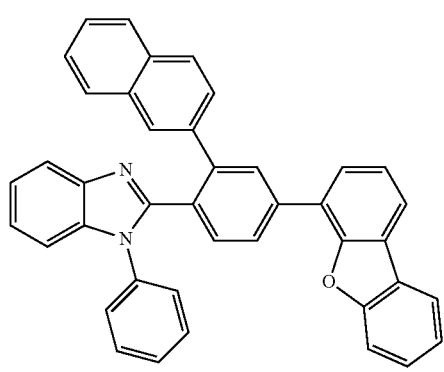
(174)
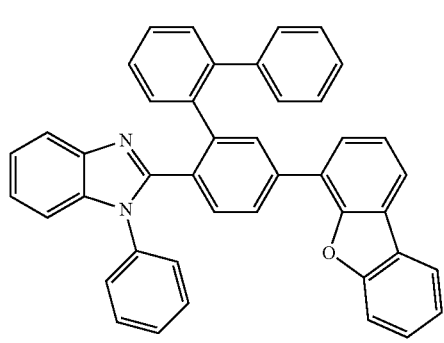
(175)
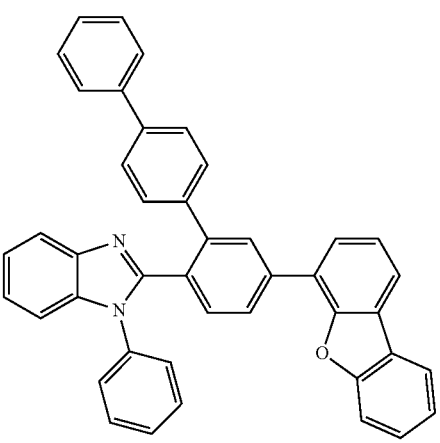
(176)
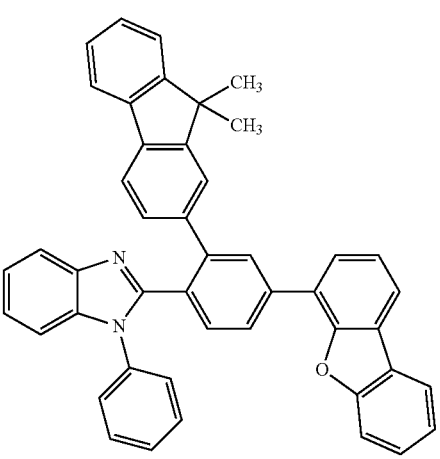
(177)
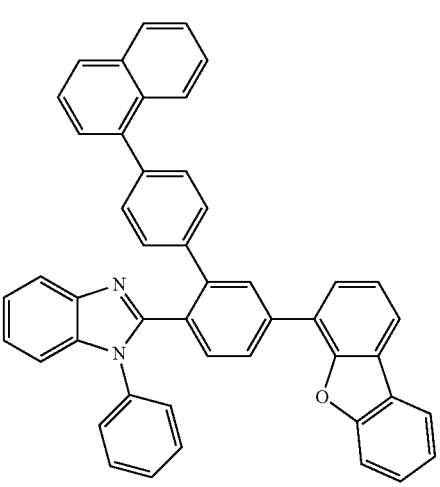

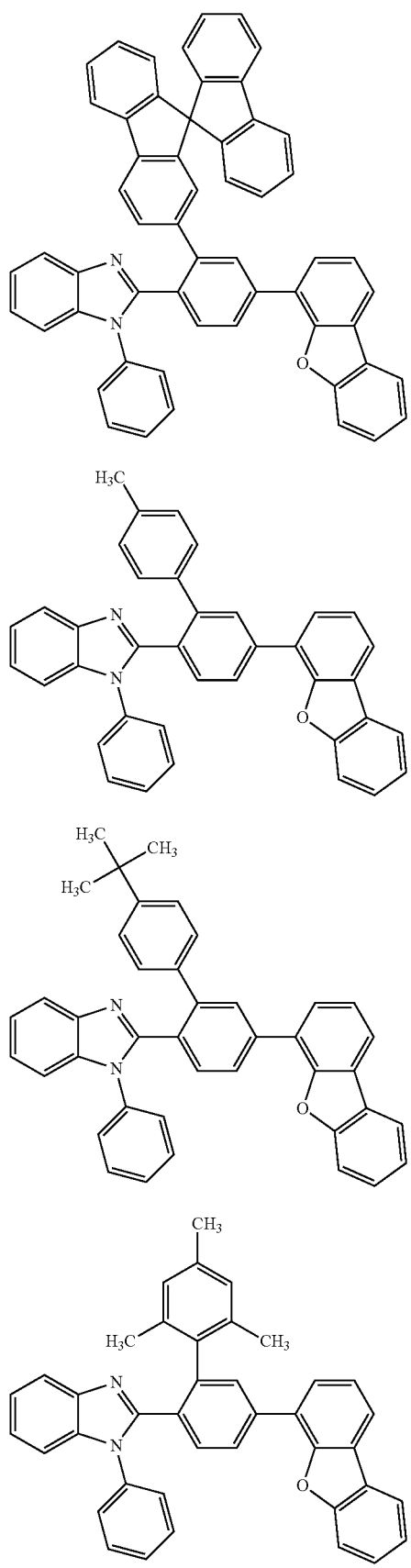
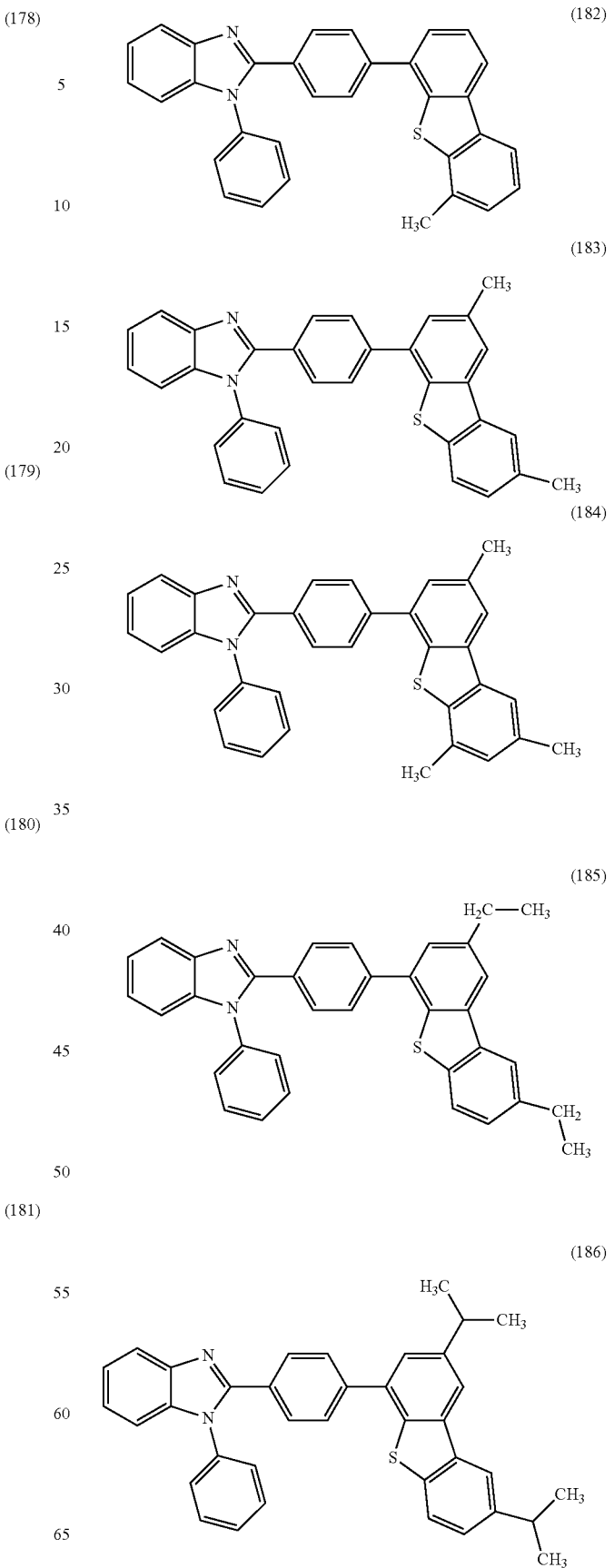

(187)
(188)
(189)
(190)
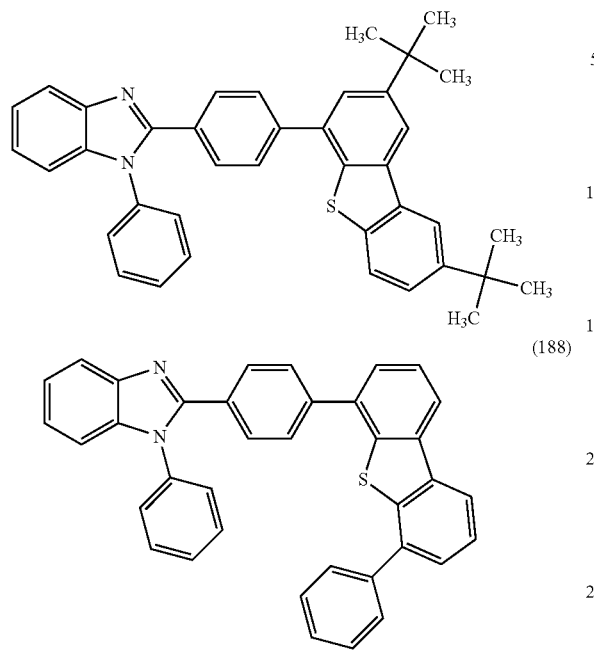
(191)
(192)
(193)
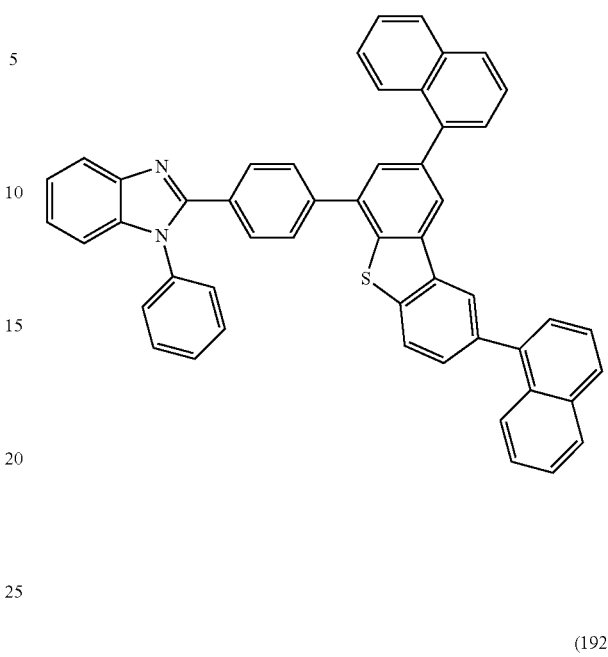
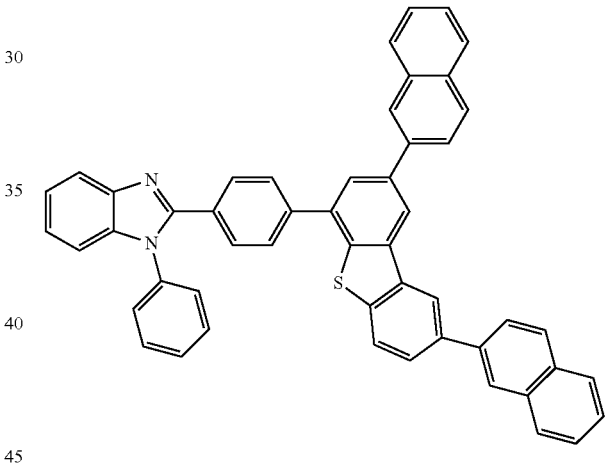
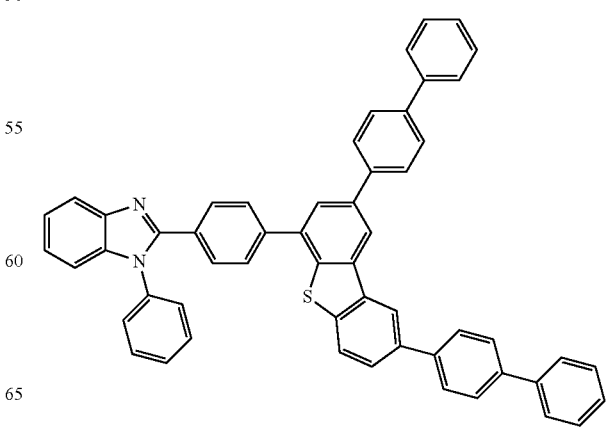

37
-continued
(194)
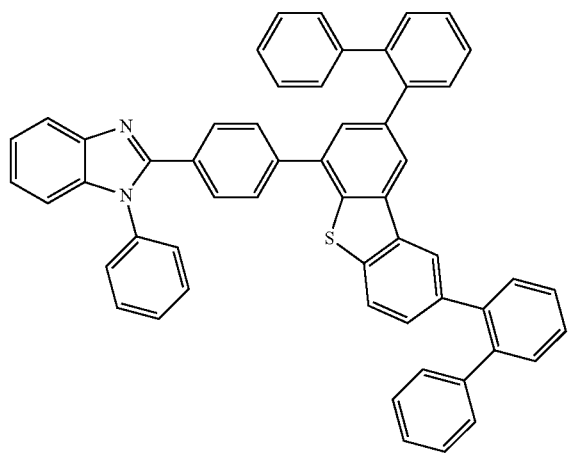
(195)
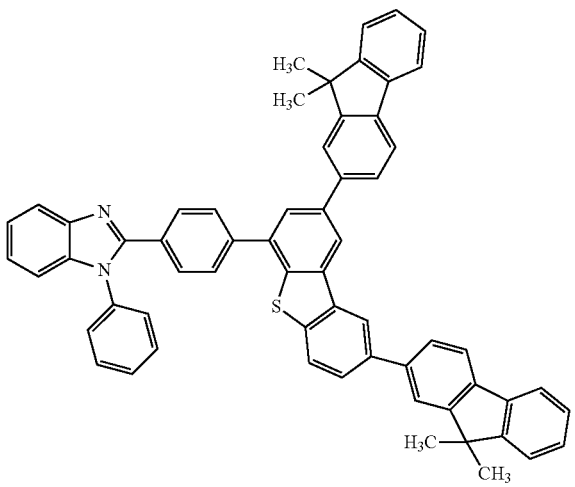
(196)
38
-continued
(197)
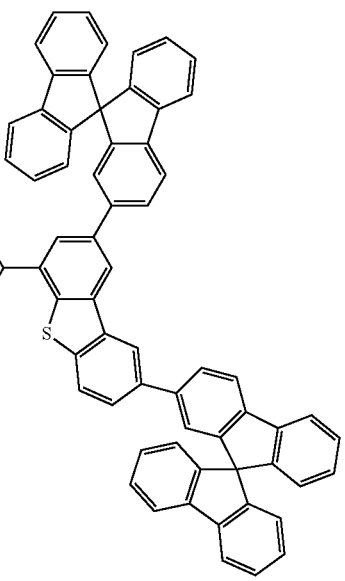
(198)
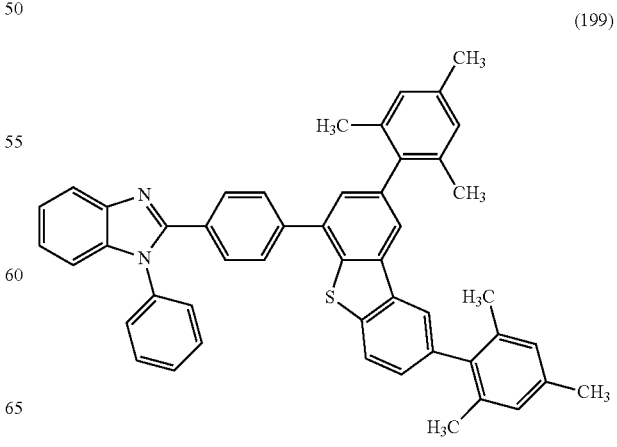
(199)

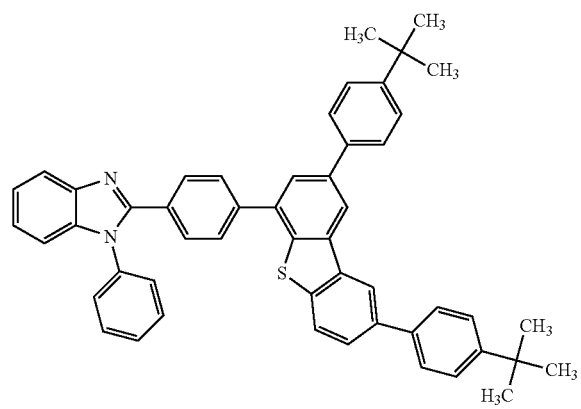
(200)
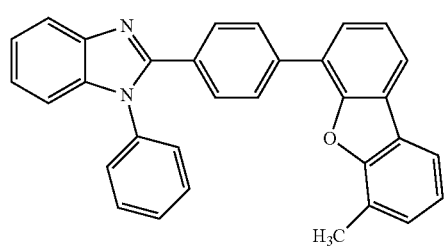
(201)
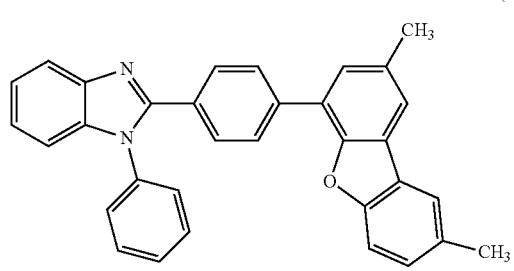
(202)
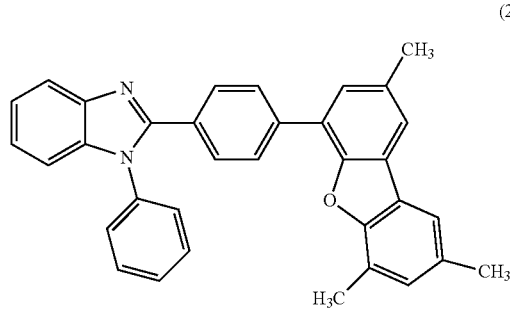
(203)
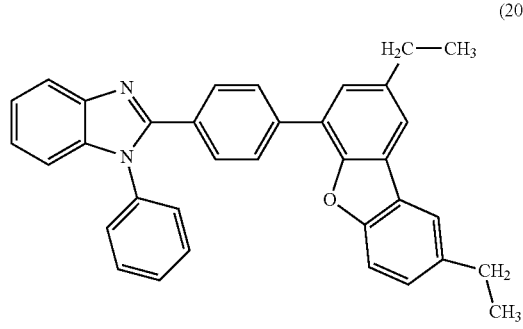
(204)
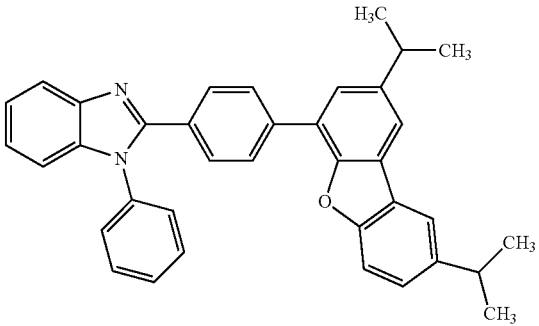
(205)
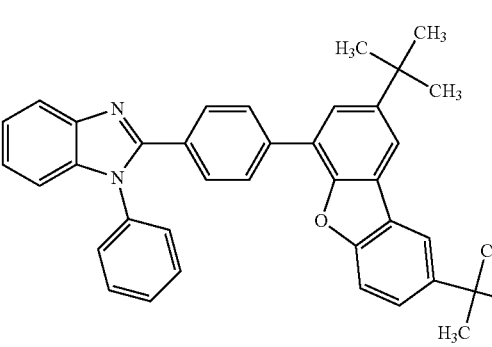
(206)
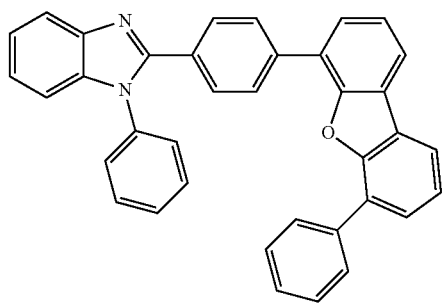
(207)
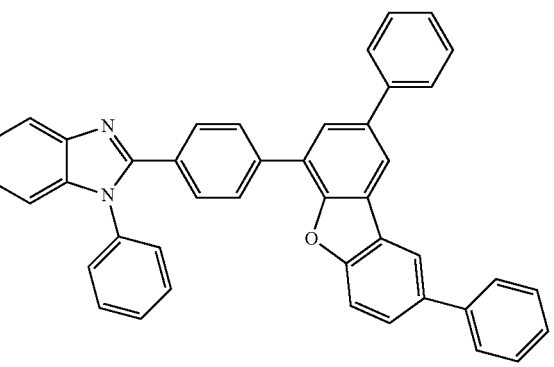
(208)

(209)
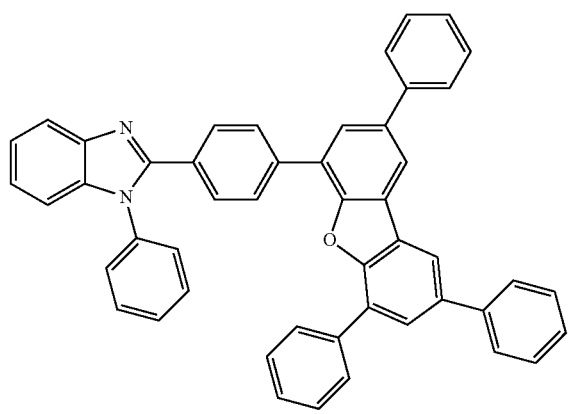
(210)
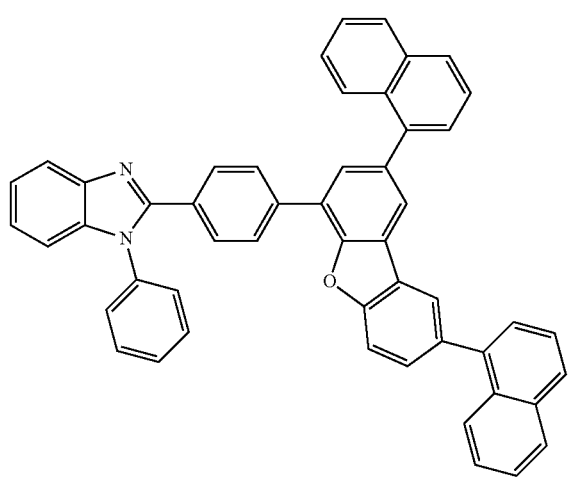
(211)
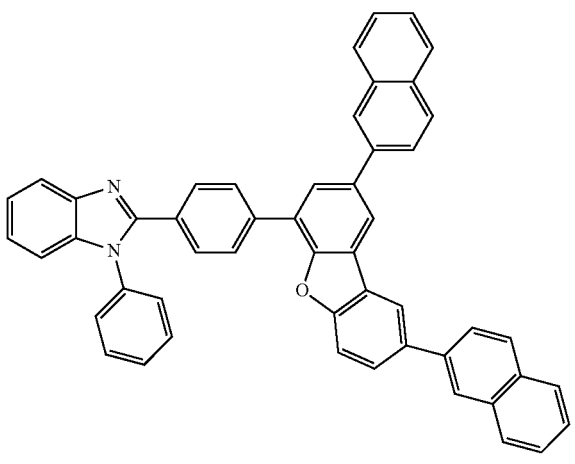
(212)
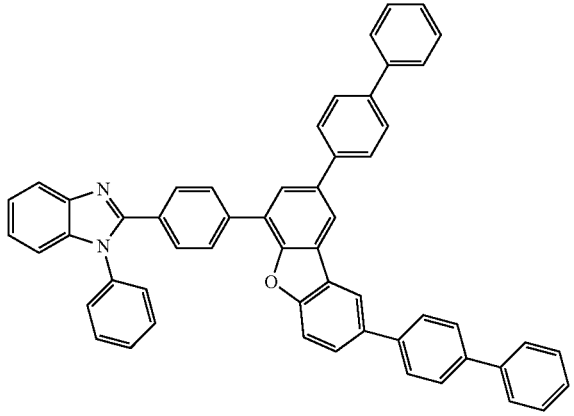
(213)
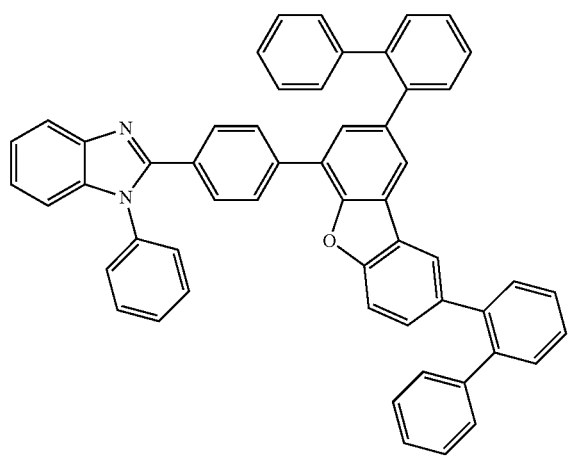
(214)
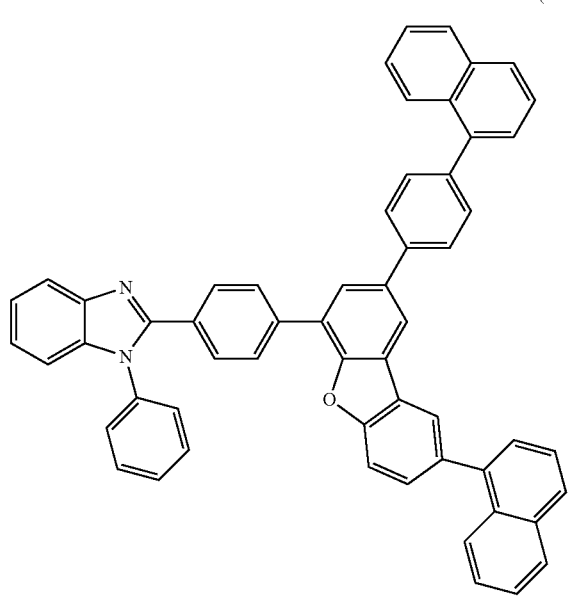

(215)

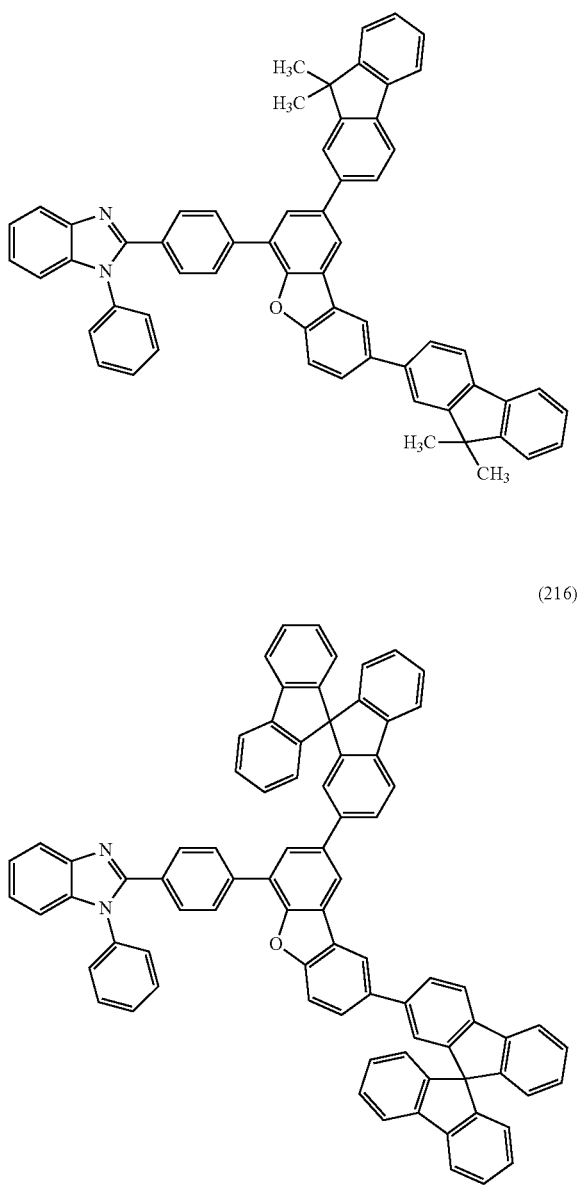

(216)

(217)

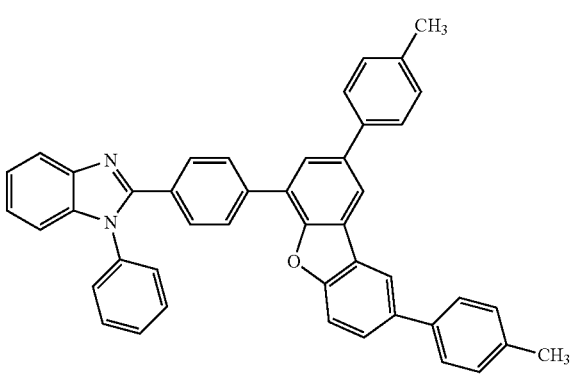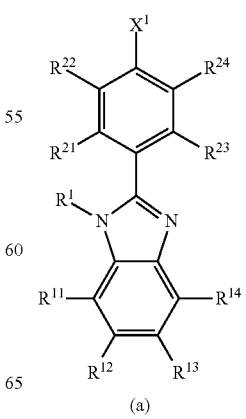

(218)

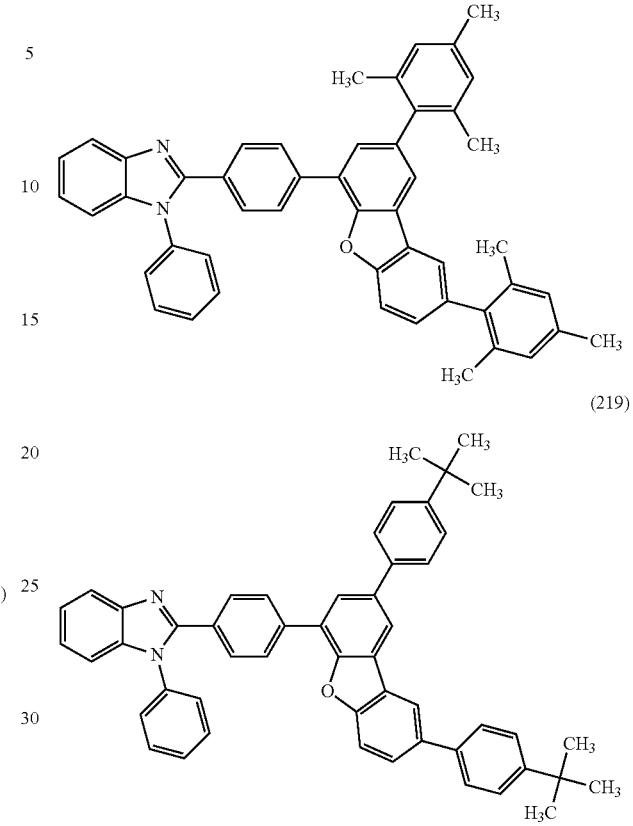

(219)

A variety of reactions can be applied to a method of synthesizing the heterocyclic compound which is one embodiment of the present invention. For example, synthesis reactions described below enable the synthesis of the heterocyclic compound of one embodiment of the present invention represented by General Formula (G1-1). Note that the method of synthesizing the heterocyclic compound which is one embodiment of the present invention is not limited to the synthesis methods below.

<Method of Synthesizing Heterocyclic Compound Represented by General Formula (G1-1)>

First, Synthesis Scheme (A-1) will be illustrated below.

(A-1)

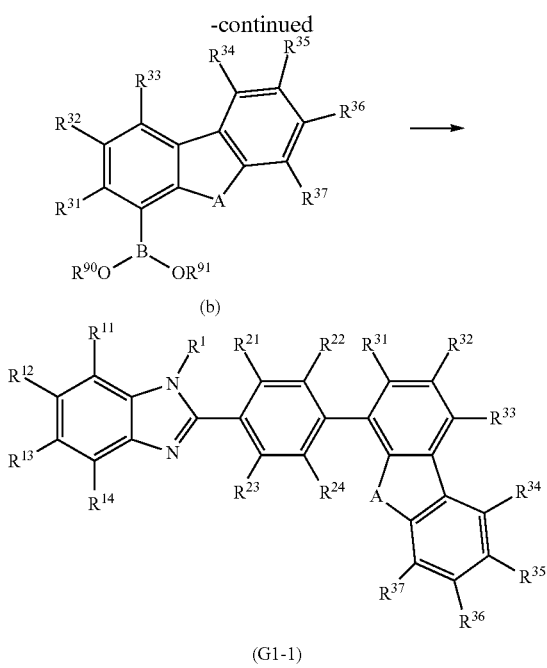

(G1-1)

The heterocyclic compound (G1-1) of one embodiment of the present invention can be synthesized as illustrated in Synthesis Scheme (A-1). Specifically, a halide of a benzimidazole derivative (Compound a) is coupled with boronic acid or an organoboron compound of a dibenzofuran derivative or a dibenzothiophene derivative (Compound b) by a Suzuki-Miyaura Reaction, whereby the heterocyclic compound (G1-1) described in this embodiment can be obtained.

In Synthesis Scheme (A-1), A represents oxygen or sulfur, $R^1$ represents an alkyl group having 1 to 4 carbon atoms or a substituted or unsubstituted aryl group having 6 to 13 carbon atoms, and $R^{11}$ to $R^{14}$, $R^{21}$ to $R^{24}$, and $R^{31}$ to $R^{37}$ separately represent any of hydrogen, an alkyl group having 1 to 4 carbon atoms, and a substituted or unsubstituted aryl group having 6 to 13 carbon atoms. Further, $R^{90}$ and $R^{91}$ separately represent hydrogen or an alkyl group having 1 to 6 carbon atoms. In Synthesis Scheme (A-1), $R^{90}$ and $R^{91}$ may be bonded to each other to form a ring. Furthermore, $X^1$ represents a halogen, preferably bromine or iodine.

Examples of the palladium catalyst that can be used in Synthesis Scheme (A-1) include, but are not limited to, palladium(II)acetate, tetrakis(triphenylphosphine)palladium(0), bis(triphenylphosphine)palladium(II) dichloride, and the like.

Examples of the ligand of the palladium catalyst which can be used in Synthesis Scheme (A-1) include, but are not limited to, tri(ortho-tolyl)phosphine, triphenylphosphine, tricyclohexylphosphine, and the like.

Examples of the base that can be used in Synthesis Scheme (A-1) include, but are not limited to, an organic base such as sodium tert-butoxide, inorganic bases such as potassium carbonate, and sodium carbonate.

Examples of the solvent that can be used in Synthesis Scheme (A-1) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is more preferable to use a mixed solvent of toluene and water, a mixed solvent of toluene, ethanol, and water, a mixed solvent of water and an ether such as ethylene glycol dimethyl ether.

As a coupling reaction in Synthesis Scheme (A-1), the Suzuki-Miyaura Reaction using the boronic acid or the organoboron compound represented by Compound b may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than halogen; however, the present invention is not limited thereto.

Further, in the Suzuki-Miyaura Coupling Reaction illustrated in Synthesis Scheme (A-1), an organoboron compound or boronic acid of a benzimidazole derivative may be coupled with a halide of a dibenzofuran derivative or a dibenzothiophene derivative or with a dibenzofuran derivative or dibenzothiophene derivative which has a triflate group as a substituent.

Thus, the heterocyclic compound of this embodiment can be synthesized.

As described above, the heterocyclic compound of one embodiment of the present invention is a compound in which the 2-position of benzimidazole and the 4-position of dibenzofuran or dibenzothiophene are bonded through a phenylene group. Note that the 2-position of dibenzofuran or dibenzothiophene, instead of the 4-position, could possibly be bonded to the phenylene group.

In that case, a technique for halogenating the 2-position of dibenzofuran or dibenzothiophene is given, for example. However, an attempt at such halogenation, which employed the method described in a document (macromolecules, Vol. 33, No. 6, 2000, pp. 1936-1939), was found difficult, because impurities were generated in the reaction and the substance to be produced was difficult to separate from the impurities. Furthermore, these substances were used as materials in a Suzuki-Miyaura Reaction as an attempt to synthesize a benzimidazole derivative in which the 2-position of benzimidazole and the 2-position of dibenzofuran or dibenzothiophene were bonded through a phenylene group; however, the substance to be produced was difficult to separate from impurities and was not able to be obtained with high purity. Specifically, after a halide of a benzimidazole derivative was made into a boronic acid compound, a coupling reaction of this compound and a halide of the 2-position of dibenzothiophene was attempted. Further, the halide of the 2-position of dibenzothiophene was made into a boronic acid compound, and then a coupling reaction of this compound and the halide of a benzimidazole derivative was attempted.

In contrast, in the case where the 4-position of dibenzofuran or dibenzothiophene was subjected to boron oxidation and coupling using the resulting substance as a material was carried out by a Suzuki-Miyaura Reaction to synthesize a benzimidazole derivative in which the 2-position of benzimidazole and the 4-position of dibenzofuran or dibenzothiophene were bonded through a phenylene group, the substance to be produced was able to be obtained with high purity.

Therefore, as compared with a heterocyclic compound in which the 2-position of benzimidazole and the 2-position of dibenzofuran or dibenzothiophene are bonded through a phenylene group, the heterocyclic compound of one embodiment of the present invention, in which the 2-position of benzimidazole and the 4-position of dibenzofuran or dibenzothiophene are bonded through a phenylene group, can be obtained easily with high purity by synthesis, and thus has high industrial applicability and is particularly preferred as an organic EL material.

Since the heterocyclic compound of one embodiment of the present invention has a wide energy gap, the heterocyclic compound is suitable for use as a host material in which a light-emitting substance of a light-emitting layer in a light-emitting element is dispersed. Further, since the heterocyclic compound of one embodiment of the present invention has a high electron-transport property, the heterocyclic compound can be preferably used as a material for an electron-transport layer in a light-emitting element. Further, the use of the heterocyclic compound of this embodiment can provide a light-emitting element having high current efficiency and a light-emitting device, an electronic device, and a lighting device each having reduced power consumption.

Embodiment 2

In Embodiment 2, a heterocyclic compound of one embodiment of the present invention will be described.

One embodiment of the present invention is the heterocyclic compound represented by General Formula (G1-2).

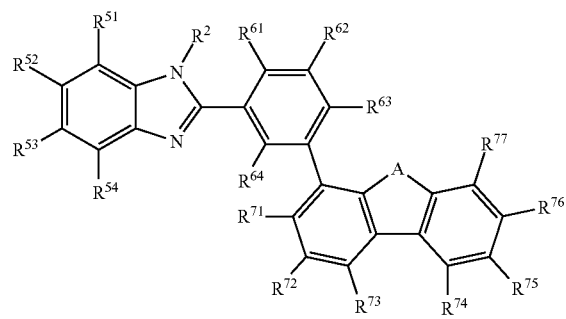

(G1-2)

In General Formula (G1-2), A represents oxygen or sulfur, $R^2$ represents an alkyl group having 1 to 4 carbon atoms or a substituted or unsubstituted aryl group having 6 to 13 carbon atoms, and $R^{51}$ to $R^{54}$, $R^{61}$ to $R^{64}$, and $R^{71}$ to $R^{77}$ separately represent any of hydrogen, an alkyl group having 1 to 4 carbon atoms, and a substituted or unsubstituted aryl group having 6 to 13 carbon atoms.

Preferred is a heterocyclic compound (G2-2) of one embodiment of the present invention in which $R^{51}$ to $R^{54}$ are each substituted with hydrogen in General Formula (G1-1), because a material for this heterocyclic compound is readily available and such a heterocyclic compound is easy to synthesize.

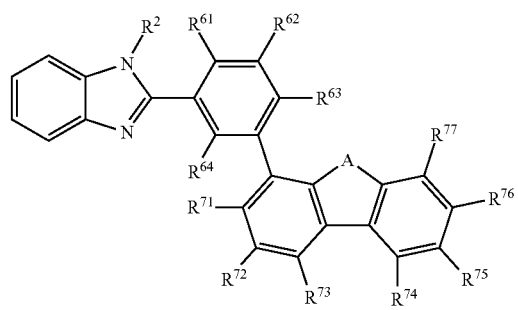

(G2-2)

In General Formula (G2-2), A represents oxygen or sulfur, $R^2$ represents an alkyl group having 1 to 4 carbon atoms or a substituted or unsubstituted aryl group having 6 to 13 carbon atoms, and $R^{61}$ to $R^{64}$ and $R^{71}$ to $R^{77}$ separately represent any of hydrogen, an alkyl group having 1 to 4 carbon atoms, and a substituted or unsubstituted aryl group having 6 to 13 carbon atoms.

Another embodiment of the present invention is the heterocyclic compound having the structure represented by General Formula (G2-2) below.

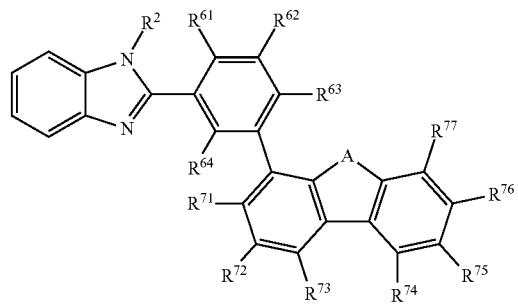

(G2-2)

In General Formula (G2-2), A represents oxygen or sulfur, $R^2$ represents an alkyl group having 1 to 4 carbon atoms or a substituted or unsubstituted aryl group having 6 to 13 carbon atoms, $R^{61}$ to $R^{64}$ separately represent any of hydrogen, an alkyl group having 1 to 4 carbon atoms, and a substituted or unsubstituted aryl group having 6 to 13 carbon atoms, and $R^{71}$ to $R^{77}$ separately represent hydrogen or a substituted or unsubstituted aryl group having 6 to 13 carbon atoms.

As specific structures of $R^1$ in General Formulae (G1-2) to (G2-2), the substituents represented by Structural Formulae (1-1) to (1-22) illustrated in Embodiment 1 can be given.

As specific structures of $R^{51}$ to $R^{54}$, $R^{61}$ to $R^{64}$, and $R^{71}$ to $R^{77}$ in General Formula (G1-2), the substituents represented by Structural Formulae (1-1) to (1-22) and (2-1) illustrated in Embodiment 1 can be given.

As specific structures of $R^{61}$ to $R^{64}$ and $R^{71}$ to $R^{77}$ in General Formula (G2-2), the substituents represented by Structural Formulae (1-1) to (1-22) and (2-1) illustrated in Embodiment 1 can be given.

Specific examples of the heterocyclic compound represented by General Formula (G1-2) include, but are not limited to, heterocyclic compounds represented by Structural Formulae (220) to (295).

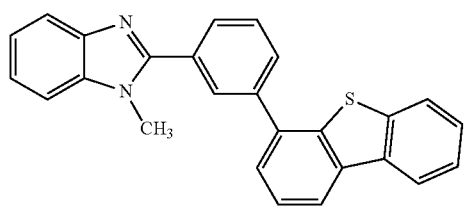 (220)
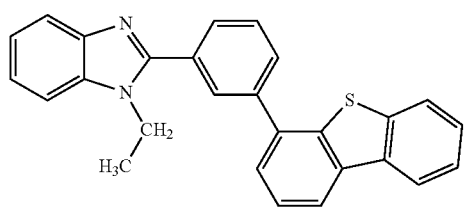 (221)
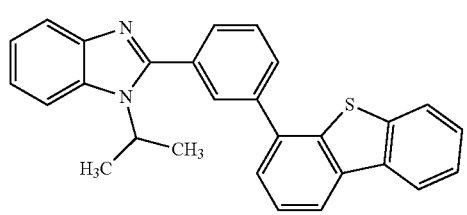 (222)
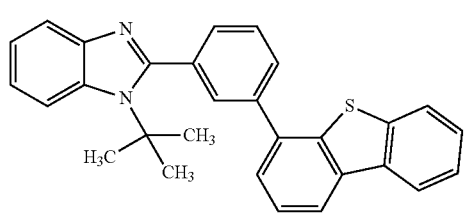 (223)
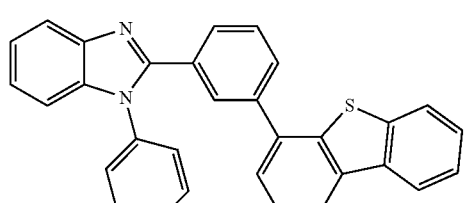 (224)
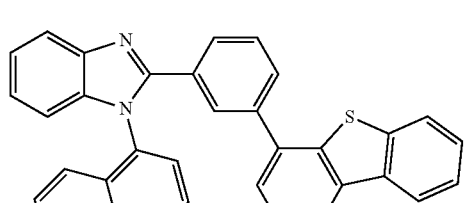 (225)
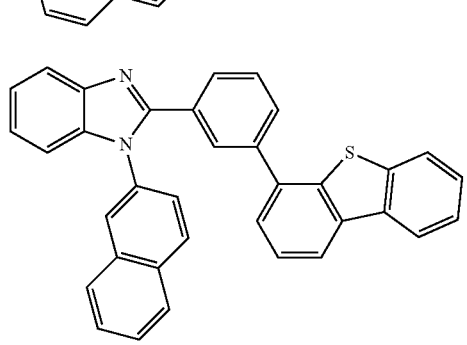 (226)
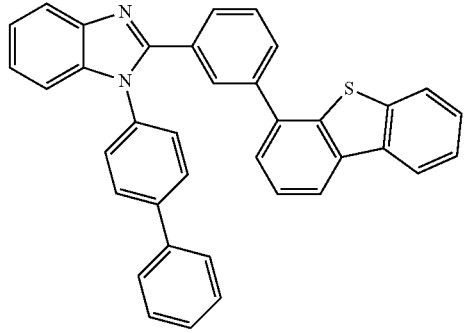 (227)
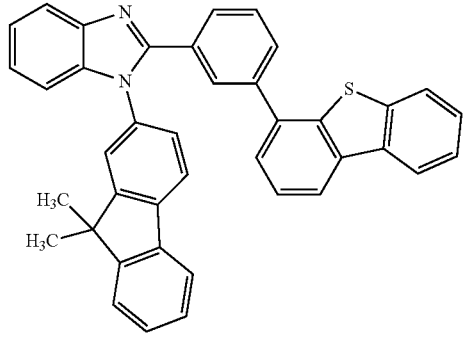 (228)
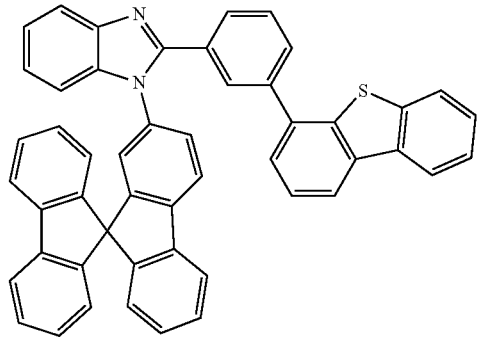 (229)
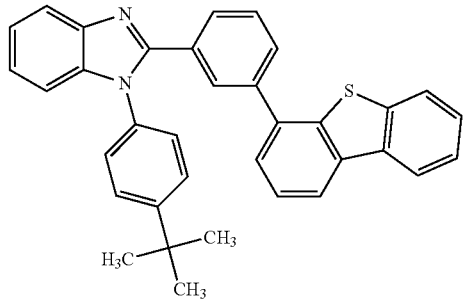 (230)
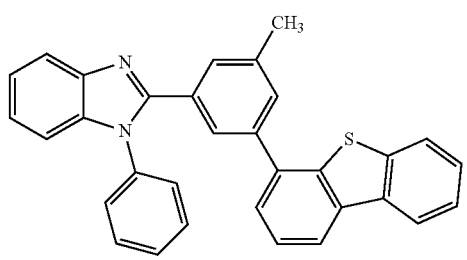 (231)

51
-continued
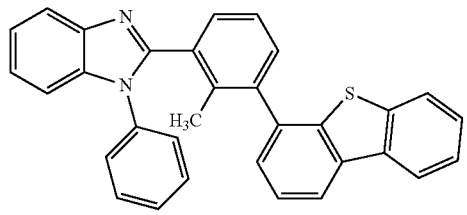
(232)
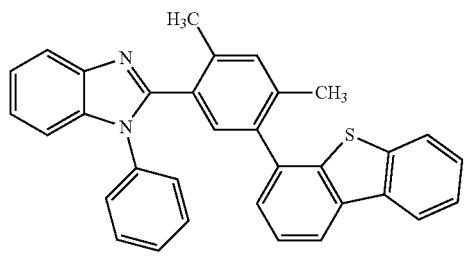
(233)
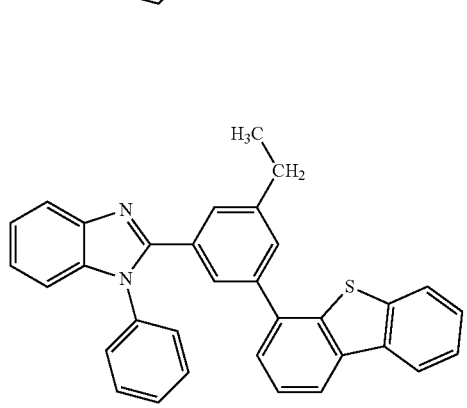
(234)
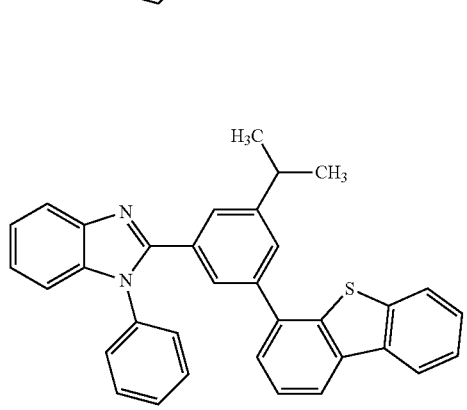
(235)
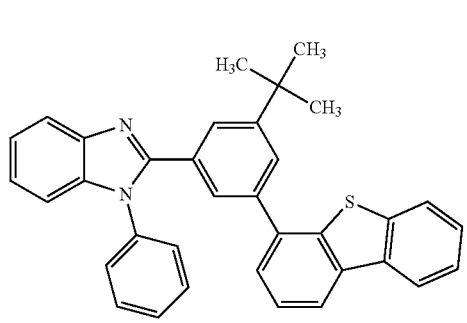
(236)
52
-continued
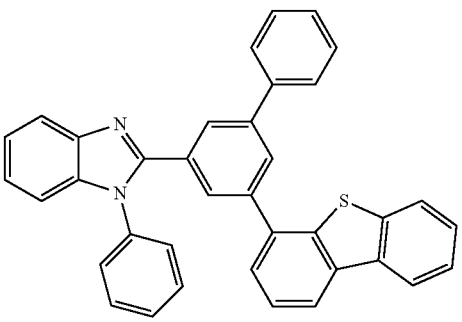
(237)
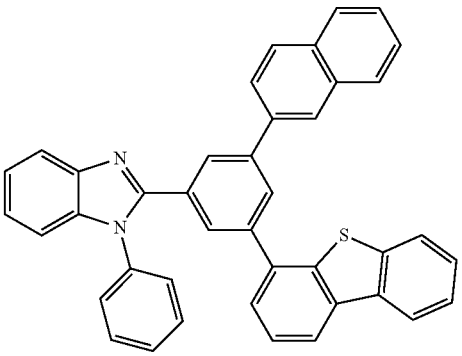
(238)
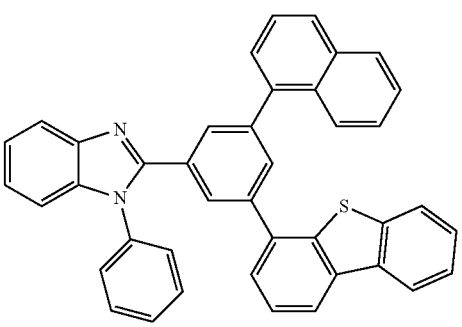
(239)
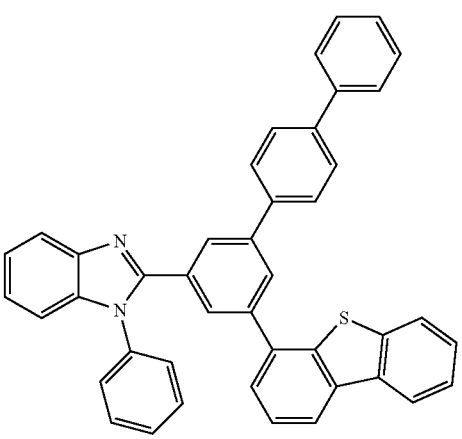
(240)

(241)
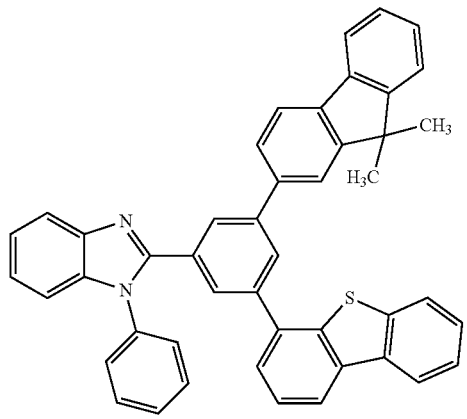
(242)
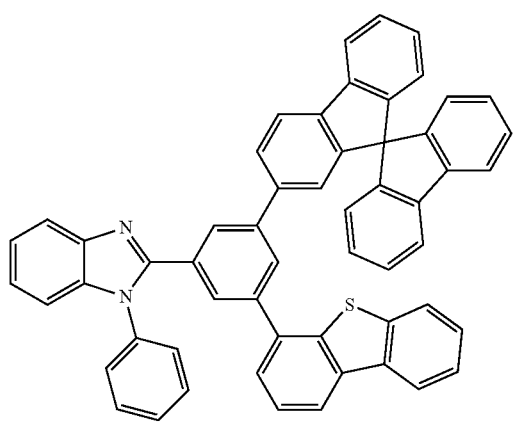
(243)
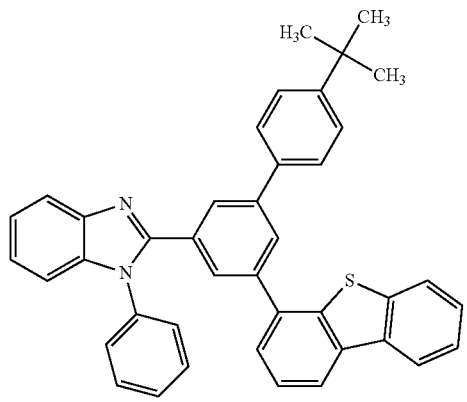
(244)
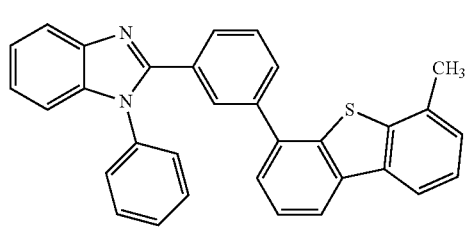
(245)
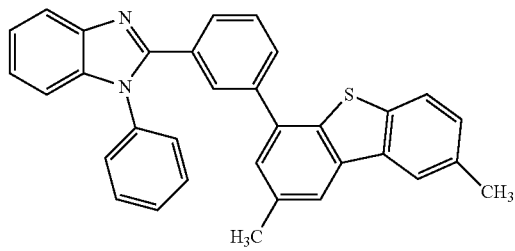
(246)
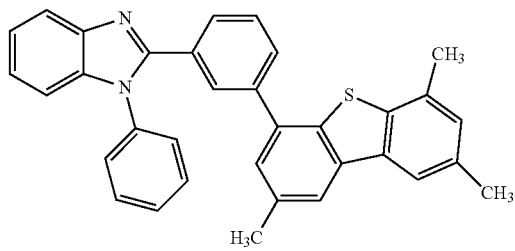
(247)
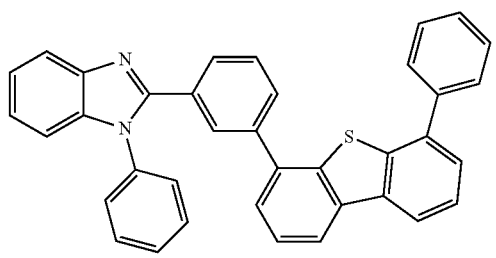
(248)
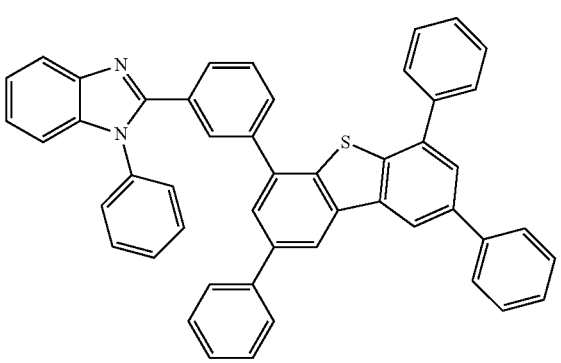
(249)
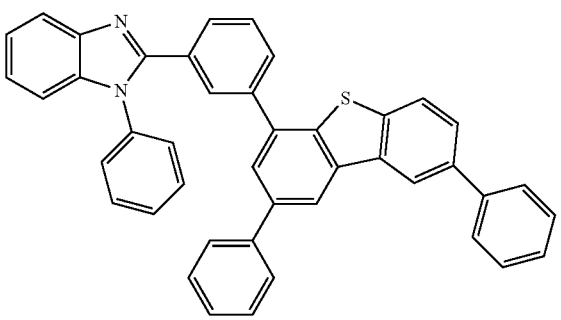

(250)
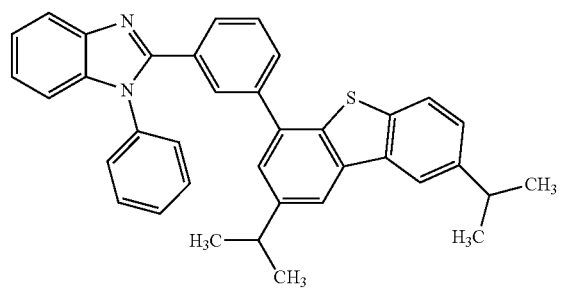
(251)
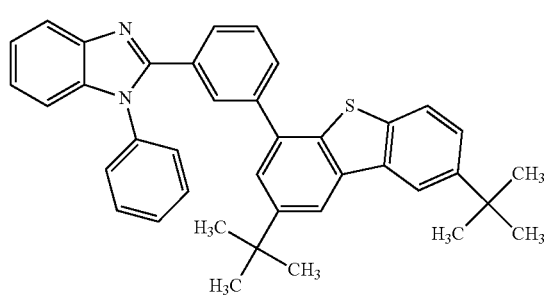
(252)
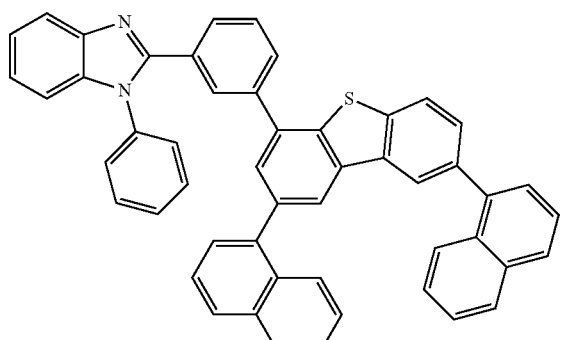
(253)
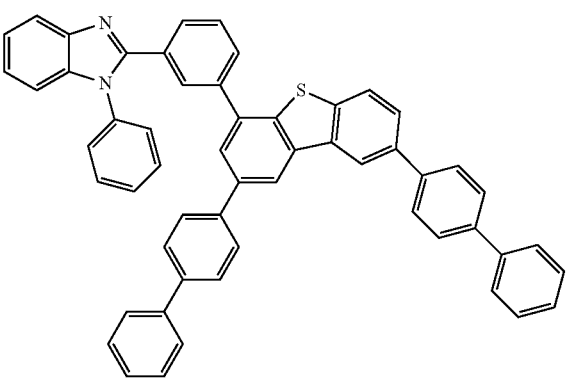
(254)
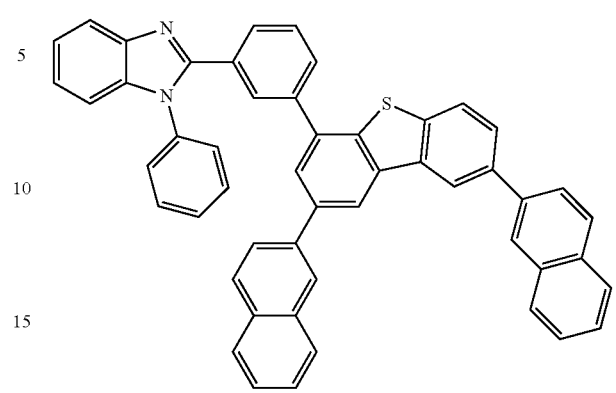
(255)
(256)
(257)
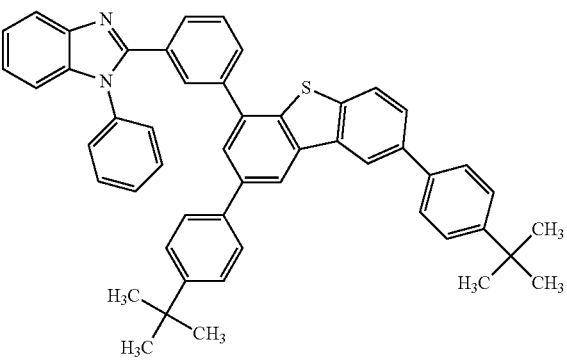

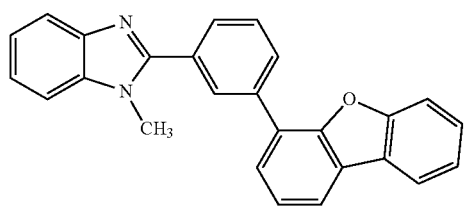
(258)
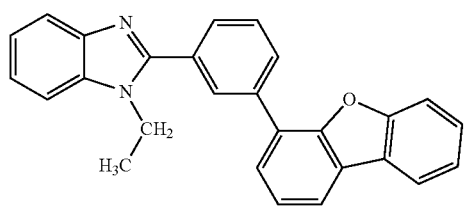
(259)
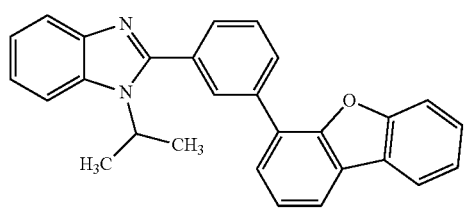
(260)
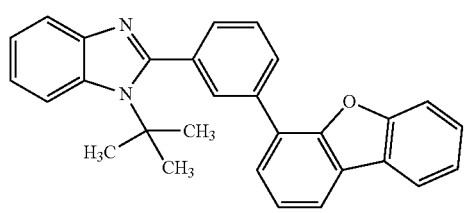
(261)
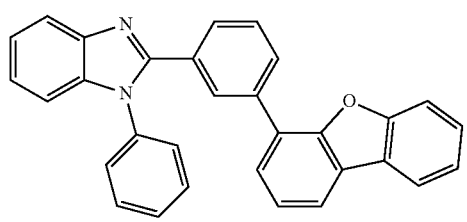
(262)
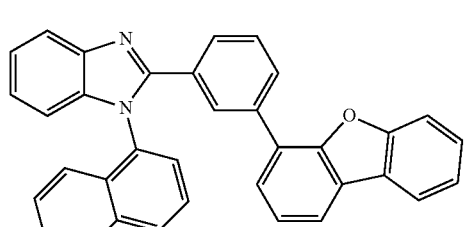
(263)
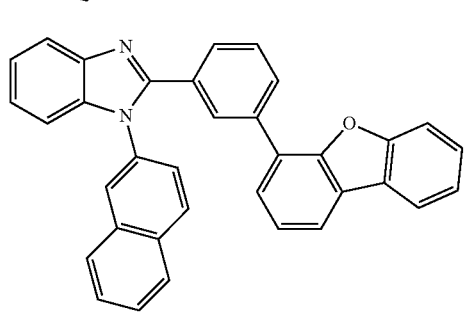
(264)
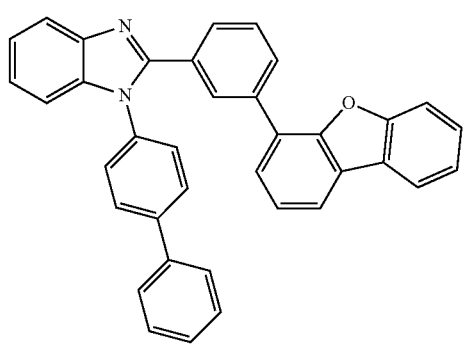
(265)
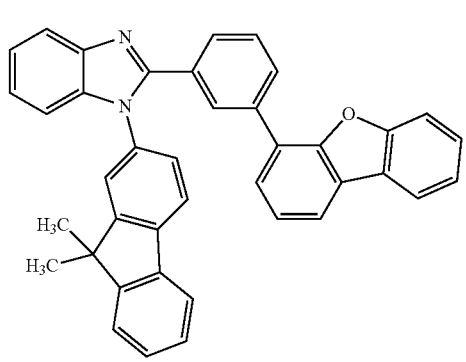
(266)
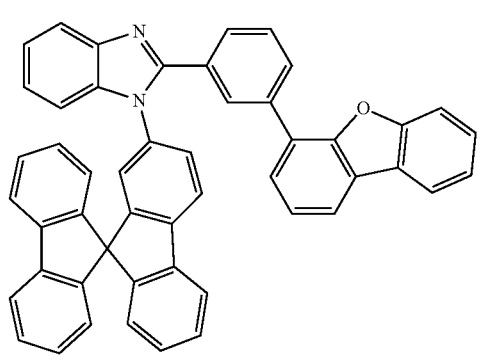
(267)
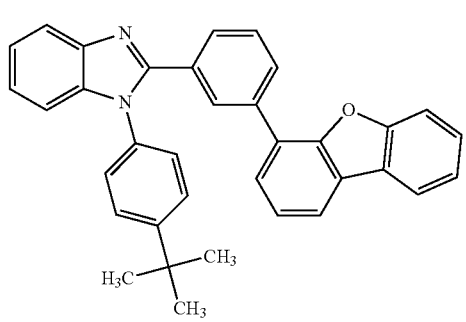
(268)
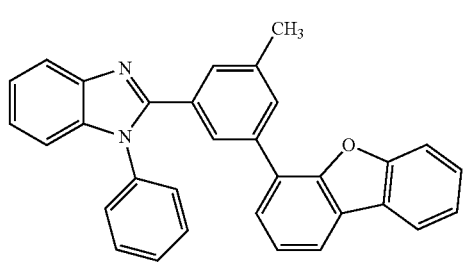
(269)

(270) 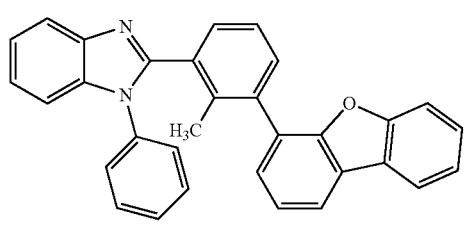
(271) 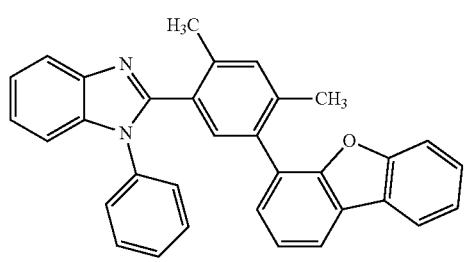
(272) 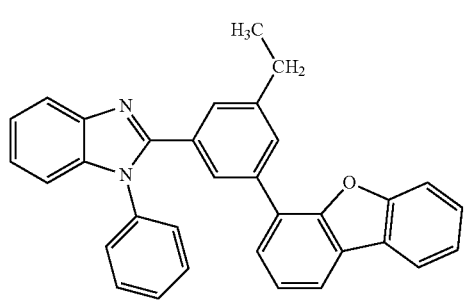
(273) 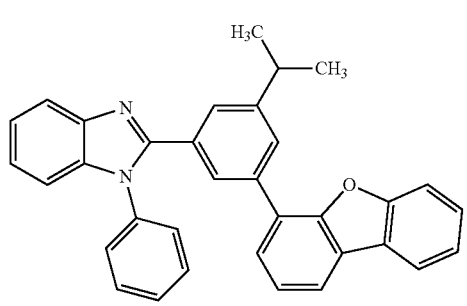
(274) 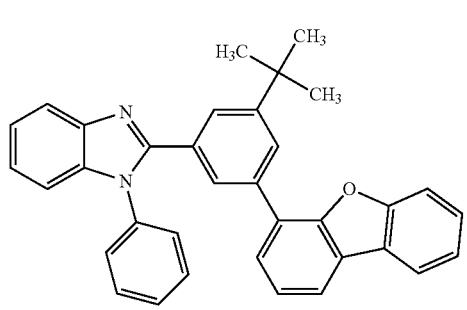
(275) 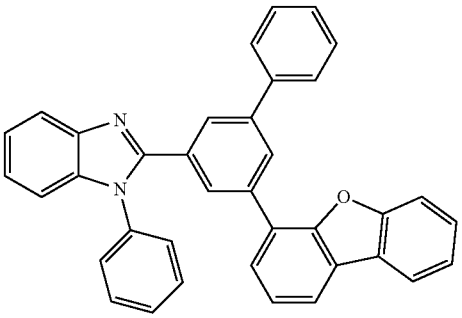
(276) 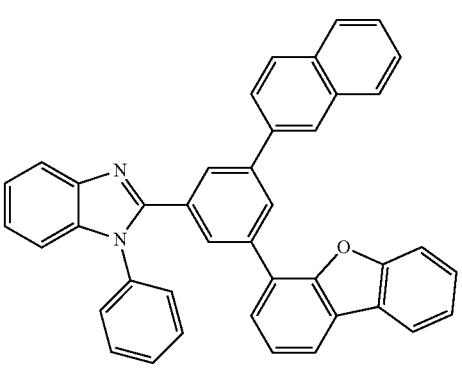
(277) 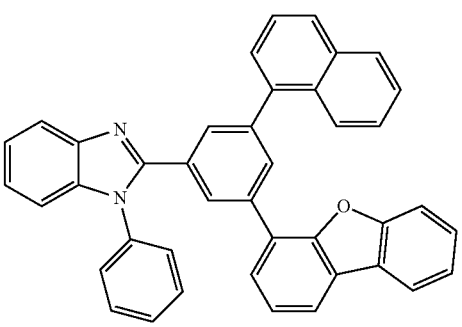
(278) 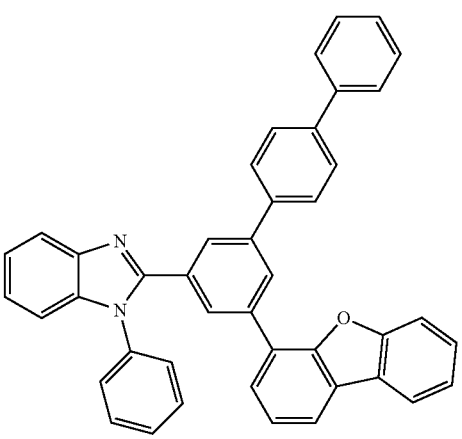

(279) 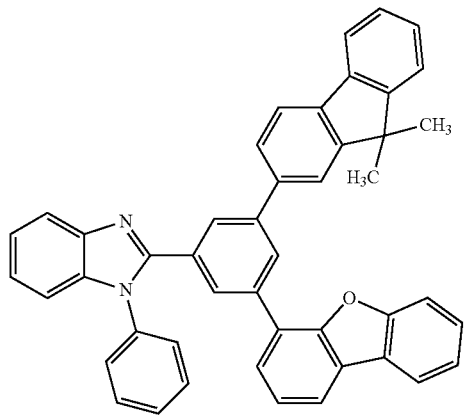
(280) 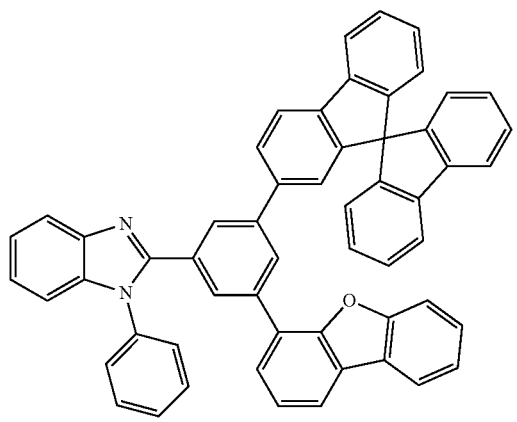
(281) 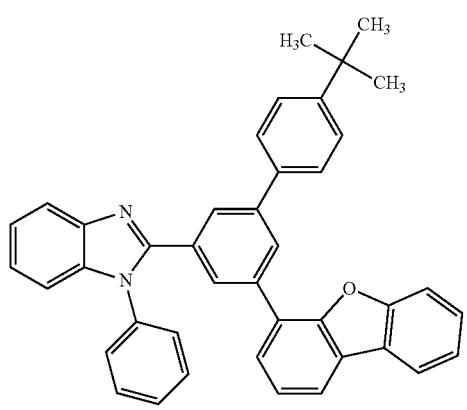
(282) 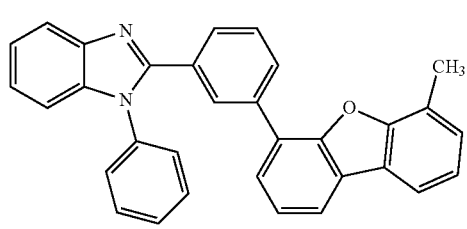
(283) 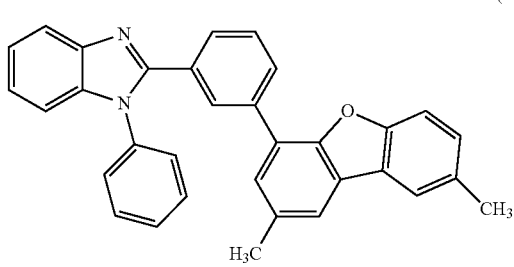
(284) 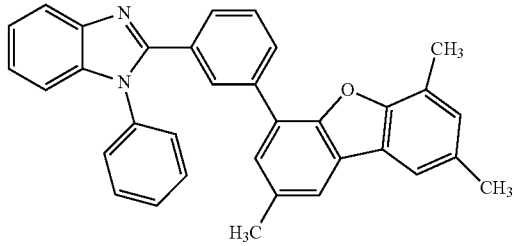
(285) 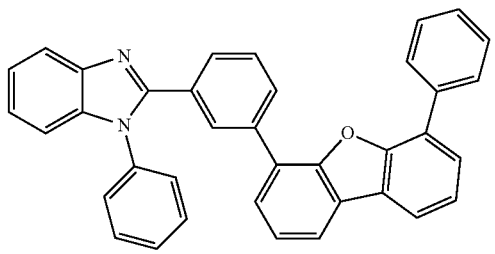
(286) 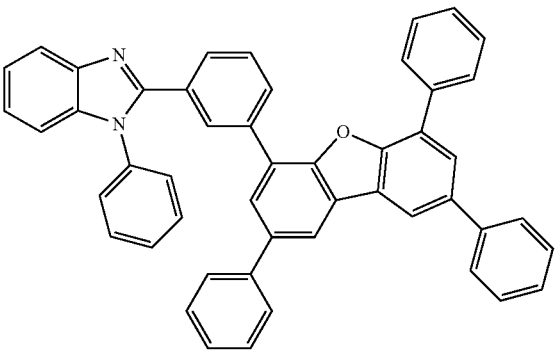
(287) 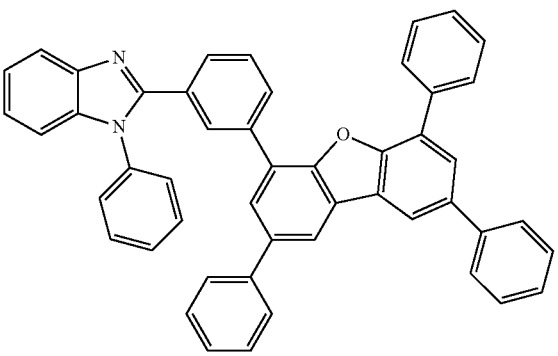

(288)
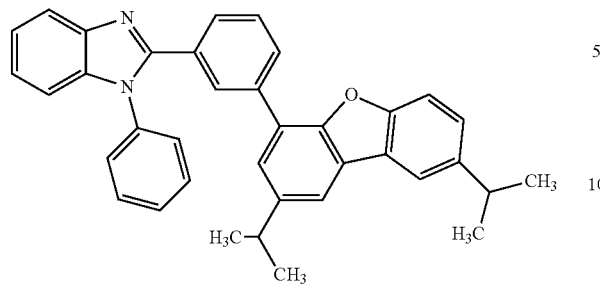
(289)
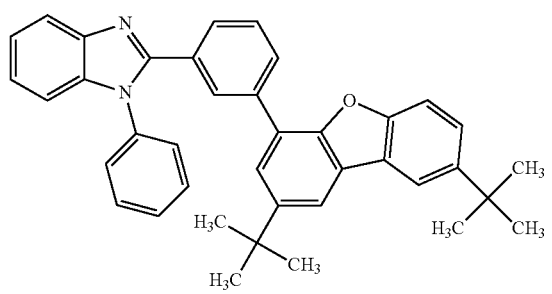
(290)
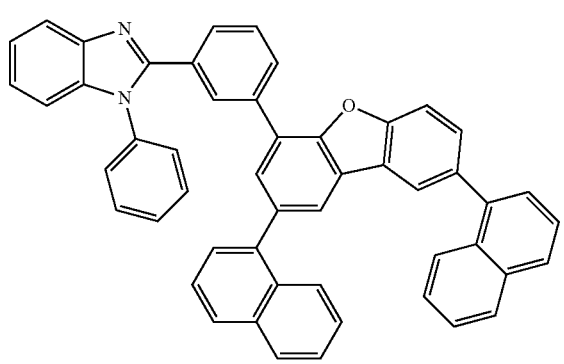
(291)
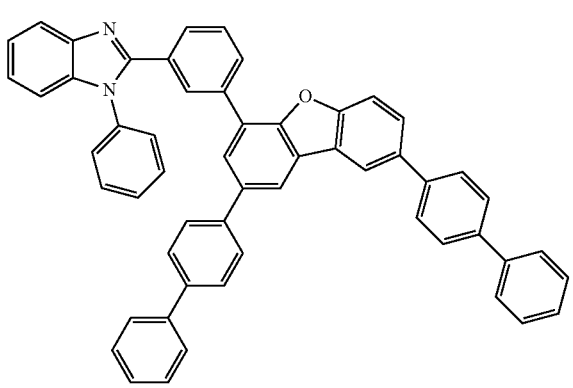
(292)
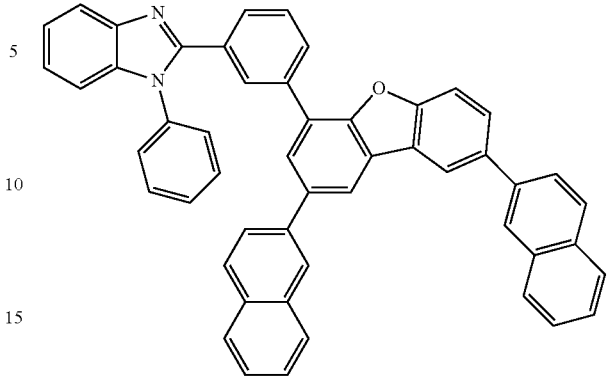
(293)
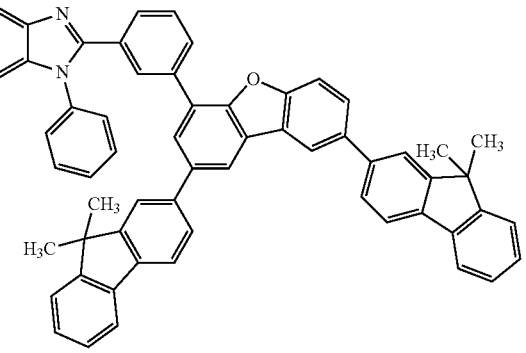
(294)
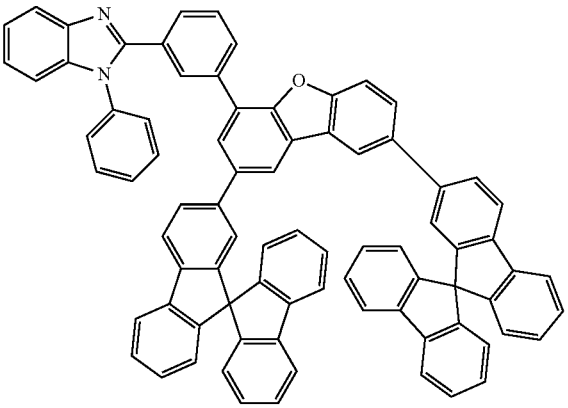
(295)
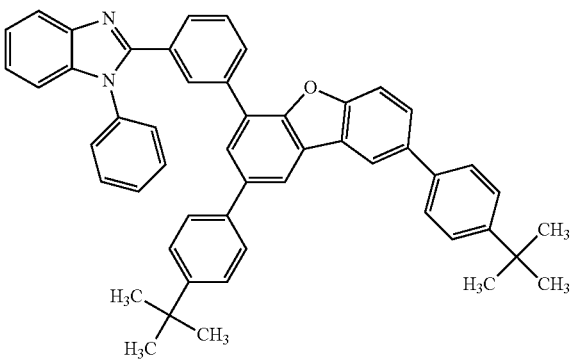
A variety of reactions can be applied to a method of synthesizing the heterocyclic compound which is one embodiment of the present invention. For example, synthesis reactions described below enable the synthesis of the heterocyclic compound of one embodiment of the present invention represented by General Formula (G1-2). Note that the method of synthesizing the heterocyclic compound which is one embodiment of the present invention is not limited to the synthesis methods below.

<Method of Synthesizing Heterocyclic Compound Represented by General Formula (G1-2)>

First, Synthesis Scheme (A-2) will be illustrated below.

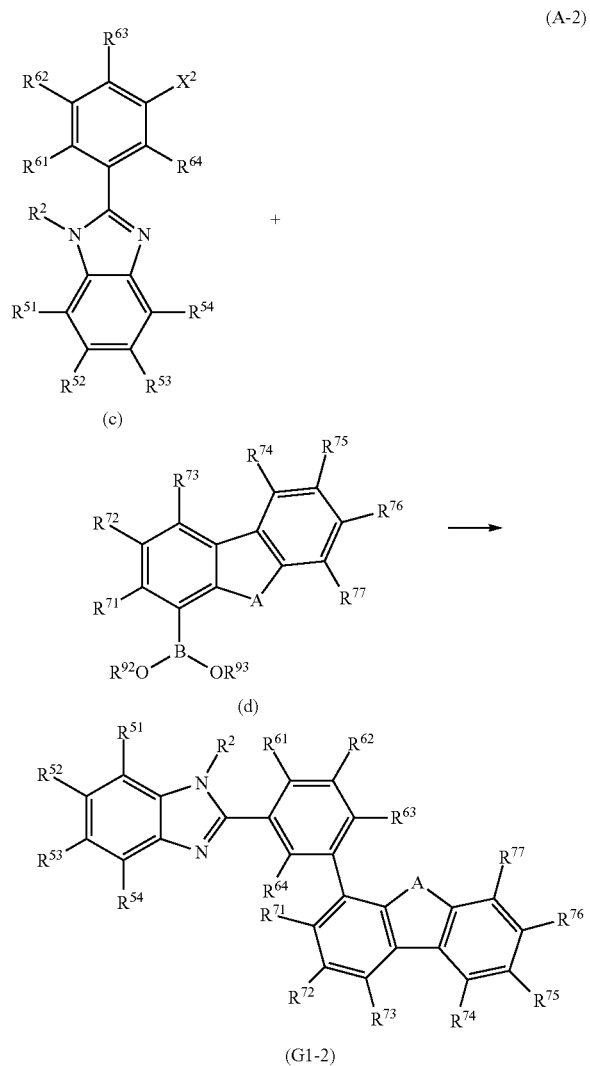

As illustrated in Synthesis Scheme (A-2), a halide of a benzimidazole derivative (Compound c) is coupled with boronic acid or an organoboron compound of a dibenzofuran derivative or a dibenzothiophene derivative (Compound d) by a Suzuki-Miyaura Reaction, whereby the heterocyclic compound (G1-2) described in this embodiment can be obtained.

In Synthesis Scheme (A-2), A represents oxygen or sulfur, $R^2$ represents an alkyl group having 1 to 4 carbon atoms or a substituted or unsubstituted aryl group having 6 to 13 carbon atoms, and $R^{51}$ to $R^{54}$, $R^{61}$ to $R^{64}$, and $R^{71}$ to $R^{77}$ separately represent any of hydrogen, an alkyl group having 1 to 4 carbon atoms, and a substituted or unsubstituted aryl group having 6 to 13 carbon atoms. Further, $R^{92}$ and $R^{93}$ separately represent hydrogen or an alkyl group having 1 to 6 carbon atoms. In Synthesis Scheme (A-2), $R^{92}$ and $R^{93}$ may be bonded to each other to form a ring. Furthermore, $X^2$ represents a halogen, preferably bromine or iodine.

Examples of the palladium catalyst that can be used in Synthesis Scheme (A-2) include, but are not limited to, palladium(II) acetate, tetrakis(triphenylphosphine)palladium (0), bis(triphenylphosphine)palladium(II) dichloride, and the like. Examples of the ligand of the palladium catalyst which can be used in Synthesis Scheme (A-2) include, but are not limited to, tri(ortho-tolyl)phosphine, triphenylphosphine, tricyclohexylphosphine, and the like.

Examples of the base that can be used in Synthesis Scheme (A-2) include, but are not limited to, an organic base such as sodium tert-butoxide, inorganic bases such as potassium carbonate, and sodium carbonate. Examples of the solvent that can be used in Synthesis Scheme (A-2) include, but are not limited to, a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and the like. It is more preferable to use a mixed solvent of toluene and water, a mixed solvent of toluene, ethanol, and water, a mixed solvent of water and an ether such as ethylene glycol dimethyl ether.

As a coupling reaction in Synthesis Scheme (A-2), the Suzuki-Miyaura Reaction using the boronic acid or the organoboron compound represented by Compound d may be replaced with a cross coupling reaction using an organoaluminum compound, an organozirconium compound, an organozinc compound, an organotin compound, or the like. However, the present invention is not limited thereto. Further, in this coupling, a triflate group or the like may be used other than halogen; however, the present invention is not limited thereto.

In the Suzuki-Miyaura Coupling Reaction illustrated in Synthesis Scheme (A-2), an organoboron compound or boronic acid of a benzimidazole derivative may be coupled with a halide of a dibenzofuran derivative or a dibenzothiophene derivative or with a dibenzofuran derivative or dibenzothiophene derivative which has a triflate group as a substituent.

Thus, the heterocyclic compound of this embodiment can be synthesized.

Since the heterocyclic compound of one embodiment of the present invention has a wide energy gap, the heterocyclic compound is suitable for use as a host material in which a light-emitting substance of a light-emitting layer in a light-emitting element is dispersed. Further, since the heterocyclic compound of one embodiment of the present invention has a high electron-transport property, the heterocyclic compound can be preferably used as a material for an electron-transport layer in a light-emitting element. Further, the use of the heterocyclic compound of this embodiment can provide a light-emitting element having high current efficiency and a light-emitting device, an electronic device, and a lighting device each having reduced power consumption.

Embodiment 3

In Embodiment 3, a light-emitting element including the heterocyclic compound of one embodiment of the present invention used for an EL layer will be described with reference to FIGS. 1A and 1B.

In the light-emitting element of this embodiment, the EL layer having at least a light-emitting layer is interposed between a pair of electrodes. The EL layer may also have a plurality of layers in addition to the light-emitting layer. The plurality of layers is a combination of a layer containing a substance having a high carrier-injection property and a layer containing a substance having a high carrier-transport property. Those layers are stacked so that a light-emitting region is formed in a region away from the electrodes, that is, carriers recombine in a region away from the electrodes. In this specification, the layer containing a substance having a high carrier-injection or -transport property is also called a functional layer which functions, for instance, to inject or transport carriers. As the functional layer, a hole-injection layer, a hole-transport layer, an electron-injection layer, an electron-transport layer, or the like can be used.

In the light-emitting element of this embodiment illustrated in FIG. 1A, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1A includes: the first electrode 101 formed over a substrate 100; the hole-injection layer 111, the hole-transport layer 112, the light-emitting layer 113, the electron-transport layer 114, and the electron-injection layer 115 which are stacked over the first electrode 101 in this order; and the second electrode 103 provided over the electron-injection layer 115. Note that, in the light-emitting element described in this embodiment, the first electrode 101 functions as an anode and the second electrode 103 functions as a cathode.

The substrate 100 is used as a support of the light-emitting element. For example, glass, quartz, plastic, or the like can be used for the substrate 100. Alternatively, a flexible substrate may be used. The flexible substrate is a substrate that can be bent, such as a plastic substrate made of polycarbonate, polyarylate, or polyether sulfone, for example. Alternatively, a film (made of polypropylene, polyester, vinyl, polyvinyl fluoride, vinyl chloride, or the like), an inorganic film formed by evaporation, or the like can be used. Note that materials other than glass and plastic can be used as long as they can function as a support of the light-emitting element in its fabrication process.

For the first electrode 101, a metal, an alloy, an electrically conductive compound, a mixture thereof, or the like which has a high work function (specifically, a work function of 4.0 eV or more) is preferably used. Specific examples include indium tin oxide (ITO), indium tin oxide containing silicon or silicon oxide, indium zinc oxide (IZO), indium oxide containing tungsten oxide and zinc oxide (IWZO), and the like. Films of these conductive metal oxides are usually formed by sputtering; however, a sol-gel method or the like may also be used. For example, indium oxide-zinc oxide (IZO) can be formed by a sputtering method using a target obtained by adding 1 wt % to 20 wt % of zinc oxide to indium oxide. IWZO can be formed by a sputtering method using a target obtained by adding 0.5 wt % to 5 wt % of tungsten oxide and 0.1 wt % to 1 wt % of zinc oxide to indium oxide. Further, gold, platinum, nickel, tungsten, chromium, molybdenum, iron, cobalt, copper, palladium, nitrides of metal materials (e.g., titanium nitride), and the like can be given.

Note that, in the EL layer 102, when a layer in contact with the first electrode 101 is formed using a composite material of an organic compound and an electron acceptor (acceptor) described later, the first electrode 101 can be formed using any of a variety of metals, alloys, and electrically conductive compounds, a mixture thereof, and the like regardless of the work function. For example, aluminum (Al), silver (Ag), an alloy containing aluminum (e.g., Al—Si), or the like can be used.

The EL layer 102 formed over the first electrode 101 includes at least the light-emitting layer 113, and part of the EL layer 102 contains the heterocyclic compound which is one embodiment of the present invention. For the part of the EL layer 102, a known substance can be used, and either a low molecular compound or a high molecular compound can be used. Note that the substance used for fowling the EL layer 102 may be only an organic compound or may partly include an inorganic compound.

Figure 1B:
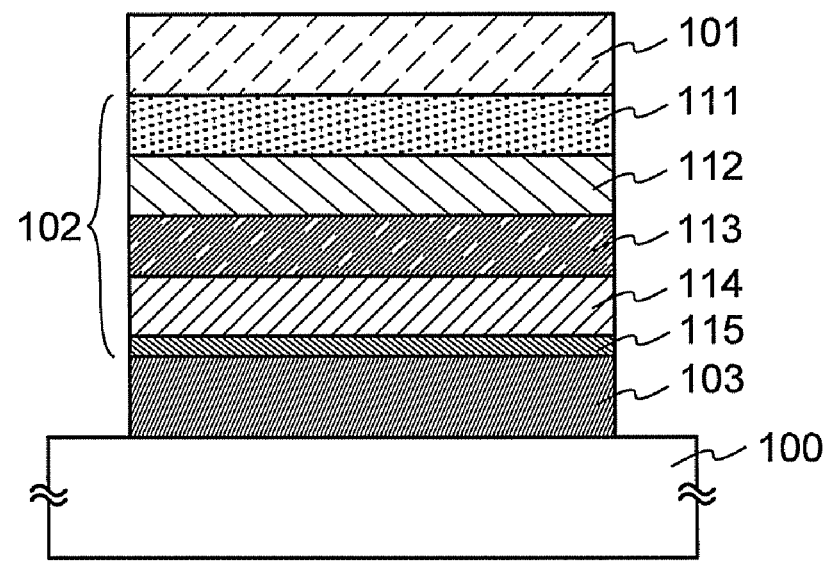

As illustrated in FIGS. 1A and 1B, the EL layer 102 is formed by stacking as appropriate the hole-injection layer 111, the hole-transport layer 112, the electron-transport layer 114, the electron-injection layer 115, and the like in combination as well as the light-emitting layer 113.

The hole-injection layer 111 is a layer including a substance having a high hole-injection property. Examples of the substance having a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide. Alternatively, a phthalocyanine-based compound such as phthalocyanine (abbreviation: $H_2Pc$), copper(II) phthalocyanine (abbreviation: CuPc), or vanadyl phthalocyanine (abbreviation: VOPc) can be used.

Alternatively, the following low molecular organic compounds can be used: 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1), and the like.

Further alternatively, any of high molecular compounds (such as oligomers, dendrimers, or polymers) can be used. Examples of the high molecular compounds include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), poly[N,N'-bis(4-butylphenyl)-N,N'-bis(phenyl)benzidine] (abbreviation: Poly-TPD), and the like. Alternatively, a high molecular compound to which acid is added, such as poly(3,4-ethylenedioxythiophene)/poly(styrenesulfonic acid) (PEDOT/PSS), or polyaniline/poly(styrenesulfonic acid) (PAni/PSS), can be used.

For the hole-injection layer 111, a composite material of an organic compound and an electron acceptor may be used. Such a composite material is excellent in a hole-injection property and a hole-transport property because the electron acceptor causes generation of holes. In this case, the organic compound is preferably a material excellent in transporting the generated holes (a substance having a high hole-transport property).

As the organic compound used for the composite material, a variety of compounds such as an aromatic amine compound, a carbazole derivative, aromatic hydrocarbon, and a high molecular compound (such as oligomer, dendrimer, or polymer) can be used. The organic compound used for the composite material is preferably an organic compound having a high hole-transport property. Specifically, a substance having a hole mobility of $10^{-6}$ cm$^2$/Vs or more is preferably used. Note that a substance other than the above may be used as long as it has a hole-transport property higher than its electron-transport property. The organic compounds which can be used for the composite material are specifically shown below.

Examples of the organic compounds that can be used for the composite material include: aromatic amine compounds such as TDATA, MTDATA, DPAB, DNTPD, DPA3B, PCz-PCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); and carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl-2,3,5,6-tetraphenylbenzene.

Alternatively, the following aromatic hydrocarbon compounds can be used: 2-tert-butyl-9,10-di(2-naphthypanthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butylanthracene, 9,10-bis[2-(1-naphthyl)phenyl]anthracene, 2,3,6,7-tetramethyl-9,10-di(1-naphthyl)anthracene, and the like.

Still alternatively, the following aromatic hydrocarbon compounds can be used: 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

As electron acceptors, organic compounds such as 7,7,8,8-tetracyano-2,3,5,6-tetrafluoroquinodimethane (abbreviation: F$_4$-TCNQ) and chloranil, and a transition metal oxide can be given. In addition, oxides of metals belonging to Groups 4 to 8 in the periodic table can be also given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air and its hygroscopic property is low and is easily treated.

Note that the hole-injection layer 111 may be formed using a composite material of the high molecular compound such as PVK, PVTPA, PTPDMA, or Poly-TPD and the electron acceptor described above.

The hole-transport layer 112 is a layer including a substance having a high hole-transport property. As the substance having a high hole-transport property, it is possible to use an aromatic amine compound such as NPB, TPD, 4,4'-bis[N-(9,9-dimethylfluoren-2-yl)-N-phenylamino]biphenyl (abbreviation: DFLDPBi), or 4,4'-bis[N-(spiro-9,9'-bifluoren-2-yl)-N-phenylamino]biphenyl (abbreviation: BSPB), for example. The substances given here are mainly materials having a hole mobility of $10^{-6}$ cm$^2$/Vs or more. Note that a substance other than the above may be used as long as it has a hole-transport property higher than its electron-transport property. The layer containing a substance having a high hole-transport property is not limited to a single layer, and may be a stack of two or more layers containing any of the above substances.

Alternatively, for the hole-transport layer 112, a high molecular compound such as PVK, PVTPA, PTPDMA, or Poly-TPD can be used.

The light-emitting layer 113 is a layer including a light-emitting substance. Note that this embodiment gives descriptions of the case where the light-emitting layer includes the heterocyclic compound of one embodiment of the present invention described in Embodiment 1 or 2. For the light-emitting layer in which a light-emitting substance (a guest material) is dispersed in another substance (a host material), the heterocyclic compound of one embodiment of the present invention can be used as the host material. By using the heterocyclic compound of one embodiment of the present invention for the light-emitting layer 113, the light-emitting layer 113 can be a light-emitting layer having a high electron-transport property. The guest material which is a light-emitting substance is dispersed in the heterocyclic compound of one embodiment of the present invention, whereby light emission can be obtained from the guest material.

In addition, the substances (host materials) in which the light-emitting substance (guest material) is dispersed can be of a plurality of kinds. The light-emitting layer may thus include another host material in addition to the heterocyclic compound of one embodiment of the present invention.

As the light-emitting substance, for example, a fluorescent compound which emits fluorescence or a phosphorescent compound which emits phosphorescence can be used. The phosphorescent compounds that can be used for the light-emitting layer 113 will be given. Examples of the materials that emits blue light include N,N'-bis[4-(9H-carbazol-9-yl)phenyl]-N,N'-diphenylstilbene-4,4'-diamine abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA), and the like. In addition, examples of the materials that emits green light include N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthrac en-2-amine (abbreviation: 2YGABPhA), N,N,9-triphenylanthracen-9-amine (abbreviation: DPhAPhA), and the like. Further, examples of the materials that emits yellow light include rubrene, 5,12-bis(1,1'-biphenyl-4-yl)-6,11-diphenyltetracene (abbreviation: BPT), and the like. Furthermore, examples of the materials that emits red light include N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), and the like.

In addition, the phosphorescent compounds that can be used for the light-emitting layer 113 will be given. Examples of the materials that emits blue light include bis[2-(4',6'- difluorophenyl)pyridinato-N,C$^{2'}$]iridium(III) tetrakis(1-pyrazolyl)borate (abbreviation: FIr$_6$), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), bis[2-(4',6'-difluorophenyl)pyridinato-N,C$^{2'}$]iridium(III)acetylacetonate (abbreviation: Fir(acac)), and the like. Examples of the materials that emits green light include tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$(acac)), bis(1,2-diphenyl-1H-benzimidazolato)iridium(III)acetylacetonate (abbreviation: Ir(pbi)$_2$(acac)), bis(benzo[h]quinolinato)iridium(III)acetylacetonate (abbreviation: Ir(bzq)$_2$(acac)), and the like. Examples of the materials that emits yellow light include bis(2,4-diphenyl-1,3-oxazolato-N,C$^{2'}$)iridium(III) acetylacetonate (abbreviation: Ir(dpo)$_2$(acac)), bis[2-(4'-(perfluorophenylphenyl)pyridinato]iridium(III)acetylacetonate (abbreviation: Ir(p-PF-ph)$_2$(acac)), bis(2-phenylbenzothiazolato-N,C$^{2'}$)iridium(III)acetylacetonate (abbreviation: Ir(bt)$_2$(acac)), and the like. Examples of the materials that emits orange light include tris(2-phenylquinolinato-N,C$^{2'}$)iridium(III) (abbreviation: Ir(pq)$_3$), bis(2-phenylquinolinato-N,C$^{2'}$)iridium(III)acetylacetonate (abbreviation: Ir(pq)$_2$(acac)), and the like. Examples of the materials that emits red light include organometallic complexes such as bis[2-(2'-benzo[4,5-α]thienyl)pyridinato-N,C$^{3'}$)iridium(III) acetylacetonate (abbreviation: Ir(btp)$_2$(acac)), bis(1-phenylisoquinolinato-N,C$^{2'}$)iridium(III)acetylacetonate (abbreviation: Ir(piq)$_2$(acac), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H, 23H-porphine platinum(II) (abbreviation: PtOEP). Furthermore, since light emission from a rare earth metal ion (electron transition between different multiplicities) can be obtained by rare earth metal complexes such as tris(acetylacetonato)(monophenanthroline)terbium(III) (abbreviation: Tb(acac)$_3$(Phen)), tris(1,3-diphenyl-1,3-propanedionato)(monophenanthroline)europium(III) (abbreviation: Eu(DBM)$_3$(Phen)), and tris[1-(2-thenyl)-3,3,3-trifluoroacetonato](monophenanthroline)europium(III) (abbreviation: Eu(TTA)$_3$(Phen)), such rare earth metal complexes can be used as a phosphorescent compound.

As the light-emitting substance, a high molecular compound can be used. Specifically, examples of the materials that emits blue light include poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), poly {(9,9-dioctylfluorene-2,7-diyl)-co-[N,N'-di-(p-butylphenyl)-1,4-diaminobenz ene]}(abbreviation: TAB-PFH), and the like. Further, examples of the materials that emits green light include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenefluorenylene)-alt-co-(2-methoxy-5-(2-ethylhexyl oxy)-1,4-phenylene)], and the like. Furthermore, examples of the materials that emits orange to red light include poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenylamino)-1,4-phenylene]}, poly{[2-methoxy-5-(2-ethylhexyloxy)-1,4-bis(1-cyanovinylenephenylene)]-alt-co[2,5-bis(N,N'-diphenylamino)-1,4-phenylene]} (abbreviation: CN-PPV-DPD), and the like.

The electron-transport layer 114 is a layer including a substance having a high electron-transport property. The heterocyclic compound of one embodiment of the present invention described in Embodiment 1 or 2 has an excellent electron-transport property and therefore can be preferably used for the electron-transport layer 114. When the heterocyclic compound of one embodiment of the present invention is used for the electron-transport layer 114, the host material of the light-emitting layer is not limited to the heterocyclic compound of one embodiment of the present invention and may be any other material.

As the substance having a high electron-transport property, any of the following substances can be used, for example: a metal complex having a quinoline skeleton or a benzoquinoline skeleton such as tris(8-quinolinolato)aluminum (abbreviation: Alq), tris(4-methyl-8-quinolinolato)aluminum (abbreviation: Almq$_3$), bis(10-hydroxybenzo[h]-quinolinato)beryllium (abbreviation: BeBq$_2$), or bis(2-methyl-8-quinolinolato)(4-phenylphenolato)aluminum (abbreviation: BAlq). Alternatively, a metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can be used. Other than the metal complex, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tent-butylphenyl)-1,2,4-triazole (abbreviation: TAZ), bathophenanthroline (abbreviation: BPhen), bathocuproine (abbreviation: BCP), or the like can be used. The substances described here are mainly materials having an electron mobility of 10$^{-6}$ cm$^2$/Vs or more. Further, the electron-transport layer is not limited to a single layer, and may be a stack of two or more layers containing any of the above substances are stacked.

The electron-injection layer 115 is a layer including a substance having a high electron-injection property. For the electron-injection layer 115, an alkali metal, an alkaline earth metal, or a compound thereof, such as lithium, cesium, calcium, lithium fluoride, cesium fluoride, calcium fluoride, or lithium oxide, can be used. Alternatively, a rare earth metal compound like erbium fluoride can be used. Alternatively, the above-mentioned substances for forming the electron-transport layer 114 can also be used.

Alternatively, a composite material in which an organic compound and an electron donor are mixed may be used for the electron-injection layer 115. Such a composite material is excellent in an electron-injection property and an electron-transport property because the electron donor causes generation of electrons. In this case, the organic compound is preferably a material excellent in transporting the generated electrons. Specifically, for example, the substances for forming the electron-transport layer 114 (e.g., a metal complex or a heteroaromatic compound), which are described above, can be used. As the electron donor, a substance showing an electron-donating property with respect to the organic compound may be used. Specifically, an alkali metal, an alkaline earth metal, and a rare earth metal are preferable, and lithium, cesium, magnesium, calcium, erbium, ytterbium, and the like can be given. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

The above-described hole-injection layer 111, hole-transport layer 112, light-emitting layer 113, electron-transport layer 114, and electron-injection layer 115 can each be formed by a method such as an evaporation method (which includes a vacuum evaporation method), an inkjet method, or a coating method.

When the second electrode 103 functions as a cathode, it can be formed using a metal, an alloy, an electrically-conductive compound, a mixture thereof, or the like having a low work function (preferably, a work function of 3.8 eV or less). Specifically, any of the following can be used: aluminum or silver; an element belonging to Group 1 or Group 2 of the periodic table, that is, an alkali metal such as lithium or cesium or an alkaline earth metal such as magnesium, calcium, or strontium; an alloy of the above metals (e.g., Mg—Ag or Al—Li); a rare earth metal such as europium or ytterbium; an alloy of the above metals; or the like.

Note that, in the case where in the EL layer 102, a layer formed in contact with the second electrode 103 is formed using a composite material in which the organic compound and the electron donor, which are described above, are mixed, a variety of conductive materials such as aluminum, silver, ITO, and indium tin oxide containing silicon or silicon oxide can be used regardless of the work function.

Note that the second electrode 103 can be formed by a vacuum evaporation method or a sputtering method. Alternatively, in the case of using a silver paste or the like, a coating method, an inkjet method, or the like can be used.

In the above-described light-emitting element of this embodiment, a current flows due to a potential difference generated between the first electrode 101 and the second electrode 103, and holes and electrons recombine in the EL layer 102, so that light is emitted. Then, this emitted light is extracted out through one or both of the first electrode 101 and the second electrode 103. One or both of the first electrode 101 and the second electrode 103 are thus have the property of transmitting visible light.

Further, a structure of the layer provided between the first electrode 101 and the second electrode 103 is not limited to the above described structure. A structure other than the above may alternatively be employed as long as a light-emitting region in which holes and electrons recombine is provided in a portion away from the first electrode 101 and the second electrode 103 in order to prevent quenching due to proximity of the light-emitting region to metal.

In other words, there is no particular limitation on a stack structure of the layers. A layer formed using a substance having a high electron-transport property, a substance having a high hole-transport property, a substance having a high electron-injection property, a substance having a high hole-injection property, a bipolar substance (a substance having a high electron-transport property and a high hole-transport property), a hole blocking material, or the like may freely be combined with a light-emitting layer including the heterocyclic compound of one embodiment of the present invention described in Embodiment 1 or 2 as a host material.

In a light-emitting element illustrated in FIG. 1B, the EL layer 102 is provided between the first electrode 101 and the second electrode 103 over the substrate 100. The EL layer 102 includes the hole-injection layer 111, the hole-transport layer 112, the light-emitting layer 113, the electron-transport layer 114, and the electron-injection layer 115. The light-emitting element in FIG. 1B includes: the second electrode 103 serving as a cathode over the substrate 100; the electron-injection layer 115, the electron-transport layer 114, the light-emitting layer 113, the hole-transport layer 112, and the hole-injection layer 111 which are stacked over the second electrode 103 in this order; and the first electrode 101 serving as an anode over the hole-injection layer 111.

A method of forming a light-emitting element will now be specifically described.

The light-emitting element of this embodiment has a structure in which an EL layer is interposed between a pair of electrodes. The EL layer has at least the light-emitting layer, and the light-emitting layer is formed using the heterocyclic compound of one embodiment of the present invention described in Embodiment 1 or 2 as a host material. Further, the EL layer may include a functional layer (e.g., a hole-injection layer, a hole-transport layer, an electron-transport layer, or an electron-injection layer) in addition to the light-emitting layer. Each electrode (the first electrode or the second electrode), the light-emitting layer, and each functional layer may be formed by any of the wet processes such as a droplet discharging method (an inkjet method), a spin coating method, and a printing method, or by a dry processes such as a vacuum evaporation method, a CVD method, and a sputtering method. A wet process allows formation at atmospheric pressure with a simple device and process, thereby having the effects of simplifying the process and improving the productivity. In contrast, a dry process does not need dissolution of a material to enable use of a material that has low solubility in a solution, thereby expanding the range of material choices.

All the thin films included in the light-emitting element may be formed by a wet method. In this case, the light-emitting element can be manufactured with only facilities needed for a wet process. Alternatively, formation of the stacked layers up to formation of the light-emitting layer may be performed by a wet process whereas the functional layer, the first electrode, and the like which are stacked over the light-emitting layer may be formed by a dry process. Further alternatively, the second electrode and the functional layer may be formed by a dry process before the formation of the light-emitting layer whereas the light-emitting layer, the functional layer stacked thereover, and the first electrode may be formed by a wet process. Needless to say, this embodiment is not limited to this, and the light-emitting element can be formed by appropriate selection from a wet method and a dry method depending on a material to be used, necessary film thickness, and the interface state.

In this embodiment, the light-emitting element is fabricated over a substrate made of glass, plastic or the like. By forming a plurality of such light-emitting elements over one substrate, a passive matrix light-emitting device can be manufactured. Alternatively, a thin film transistor (TFT), for instance, may be formed over a substrate made of glass, plastic, or the like, and a light-emitting element may be fabricated over an electrode electrically connected to the TFT; thus, an active matrix light-emitting device in which the TFT controls driving of the light-emitting element can be manufactured. Note that there is no particular limitation on the structure of the TFT. Either a staggered TFT or an inverted staggered TFT may be employed. In addition, there is no particular limitation on crystallinity of a semiconductor used for the TFT; an amorphous semiconductor or a crystalline semiconductor may be used. In addition, a driver circuit formed over a TFT substrate may be constructed from both or one of n-channel and p-channel TFTs.

The heterocyclic compound of one embodiment of the present invention described in Embodiment 1 or 2 has a high electron-transport property and a wide energy gap. Hence, by using the heterocyclic compound of one embodiment of the present invention described in Embodiment 1 or 2 for a light-emitting element, drive voltage of the light-emitting element can be low. In addition, current efficiency of the light-emitting element can be high. Furthermore, a light-emitting device (such as an image display device) using this light-emitting element of one embodiment of the present invention which is obtained as above can have low power consumption.

Note that by use of the light-emitting element described in this embodiment, a passive matrix light-emitting device or an active matrix light-emitting device in which a transistor controls driving of the light-emitting element can be manufactured.

This embodiment can be implemented in appropriate combination with any of the other embodiments.

Embodiment 4

In Embodiment 4, a mode of a light-emitting element having a structure in which a plurality of light-emitting units is stacked (hereinafter, referred to as a stacked-type element) will be described with reference to FIGS. 2A and 2B. This light-emitting element is a light-emitting element including a plurality of light-emitting units between a first electrode and a second electrode.

Figure 2A:
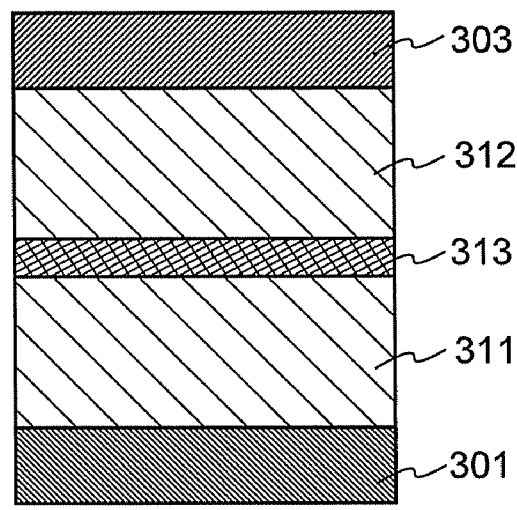
FIGS. 2A and 2B each illustrate a light-emitting element of one embodiment of the present invention.

In FIG. 2A, a first light-emitting unit 311 and a second light-emitting unit 312 are stacked between a first electrode 301 and a second electrode 303. In this embodiment, the first electrode 301 functions as an anode and the second electrode 303 functions as a cathode. The first electrode 301 and the second electrode 303 can be the same as those in Embodiment 3. Further, the first light-emitting unit 311 and the second light-emitting unit 312 may have the same or different structures. The first light-emitting unit 311 and the second light-emitting unit 312 may be the same as those in Embodiment 3, or either of the units may be the same as that in Embodiment 3.

Further, a charge generation layer 313 is provided between the first light-emitting unit 311 and the second light-emitting unit 312. The charge generation layer 313 functions so that electrons are injected into one light-emitting unit and holes are injected into the other light-emitting unit by application of a voltage between the first electrode 301 and the second electrode 303. In this embodiment, when a voltage is applied to the first electrode 301 so that the potential thereof is higher than that of the second electrode 303, the charge generation layer 313 injects electrons into the first light-emitting unit 311 and injects holes into the second light-emitting unit 312.

Note that the charge generation layer 313 preferably has the property of transmitting visible light in terms of light extraction efficiency. Further, the charge generation layer 313 functions even when it has lower conductivity than the first electrode 301 or the second electrode 303.

The charge generation layer 313 may have either a structure including an organic compound having a high hole-transport property and an electron acceptor or a structure including an organic compound having a high electron-transport property and an electron donor. Alternatively, both of these structures may be stacked.

In the case where the charge generation layer 313 contains an electron acceptor and an organic compound having a high hole-transport property, as the organic compound having a high hole-transport property, for example, the heterocyclic compound of one embodiment of the present invention, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances given here are mainly materials having a hole mobility of $10^{-6}$ cm$^2$/Vs or more. Note that a substance other than the above may be used as long as it is an organic compound having a hole-transport property higher than its electron-transport property.

Further, as the electron acceptor, 7,7,8,8-tetracyano-2,3,5,6-tetrafluoroquinodimethane (abbreviation: F$_4$-TCNQ), chloranil, and the like can be given. In addition, transition metal oxides can be given. Moreover, oxides of metals belonging to Groups 4 to 8 of the periodic table can be used. Specifically, vanadium oxide, niobium oxide, tantalum oxide, chromium oxide, molybdenum oxide, tungsten oxide, manganese oxide, and rhenium oxide are preferable because they have a high electron-accepting property. Among these metal oxides, molybdenum oxide, which is easy to handle, is preferred owing to its stability in air and low hygroscopic property.

On the other hand, in the case where the charge generation layer 313 includes an electron donor and an organic compound having a high hole-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Alternatively, in addition to such a metal complex, PBD, OXD-7, TAZ, BPhen, BCP, or the like can be used. The substances given here are mainly materials having an electron mobility of $10^{-6}$ cm$^2$/Vs or more. Note that a substance other than the above may be used as long as it is an organic compound having an electron-transport property higher than its hole-transport property.

Further, as the electron donor, an alkali metal, an alkaline earth metal, a rare earth metal, a metal belonging to Group 13 of the periodic table, or an oxide or carbonate thereof can be used. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

Note that by formation of the charge generation layer 313 using any of the above materials, it is possible to suppress an increase in drive voltage caused by stacking the EL layers.

Figure 2B:
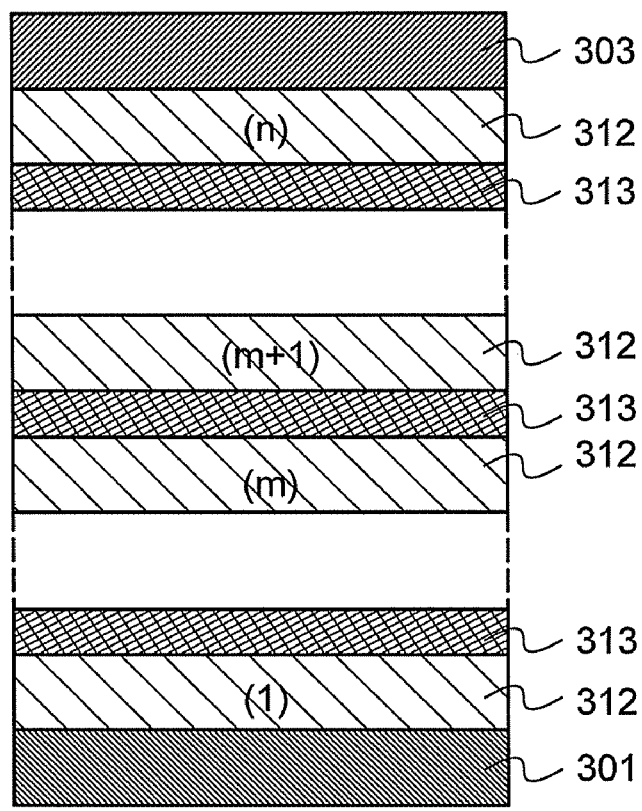

In this embodiment, the light-emitting element having two light-emitting units is described, and one embodiment of the present invention can be similarly applied to a light-emitting element having a stack of three or more light-emitting units as illustrated in FIG. 2B. A plurality of light-emitting units which are partitioned by the charge generation layer are arranged between a pair of electrodes, as in the light-emitting element of this embodiment, whereby the element can emit light in a high luminance region while current density is kept low. Since the current density can be kept low, the element can have a long lifetime.

With light-emitting units having emission colors different from each other, the light-emitting element as a whole can be made to emit light having a desired color. For example, in a light-emitting element having two light-emitting units, the emission colors of the first light-emitting unit and the second light-emitting unit are made complementary; thus, the light-emitting element which emits white light as a whole can be obtained. Note that the term "complementary" means color relationship in which an achromatic color is obtained when colors are mixed. That is, white light emission can be obtained by mixture of light obtained from substances emitting lights having complementary colors. The same can be applied to a light-emitting element which has three light-emitting units. For example, the light-emitting element as a whole can emit white light when the emission color of the first light-emitting unit is red, the emission color of the second light-emitting unit is green, and the emission color of the third light-emitting unit is blue.

Note that this embodiment can be combined with any other embodiment as appropriate.

Embodiment 5

Figure 3A:
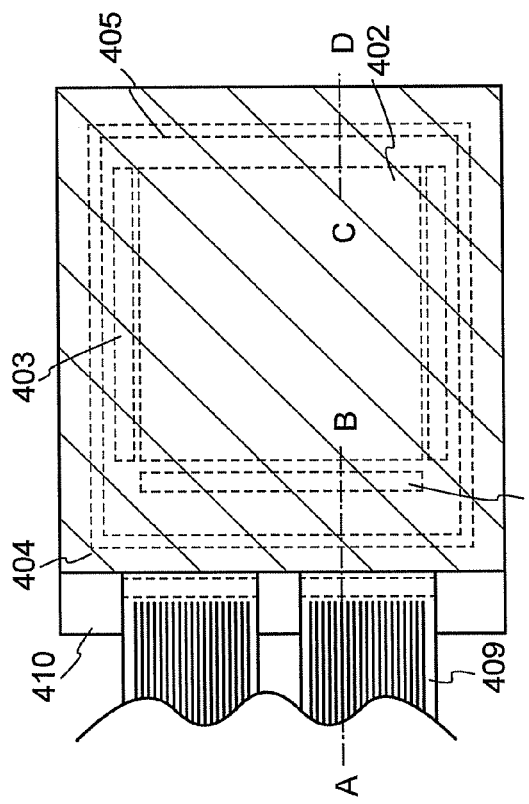
FIGS. 3A and 3B illustrate a light-emitting device of one embodiment of the present invention.
Figure 3B:
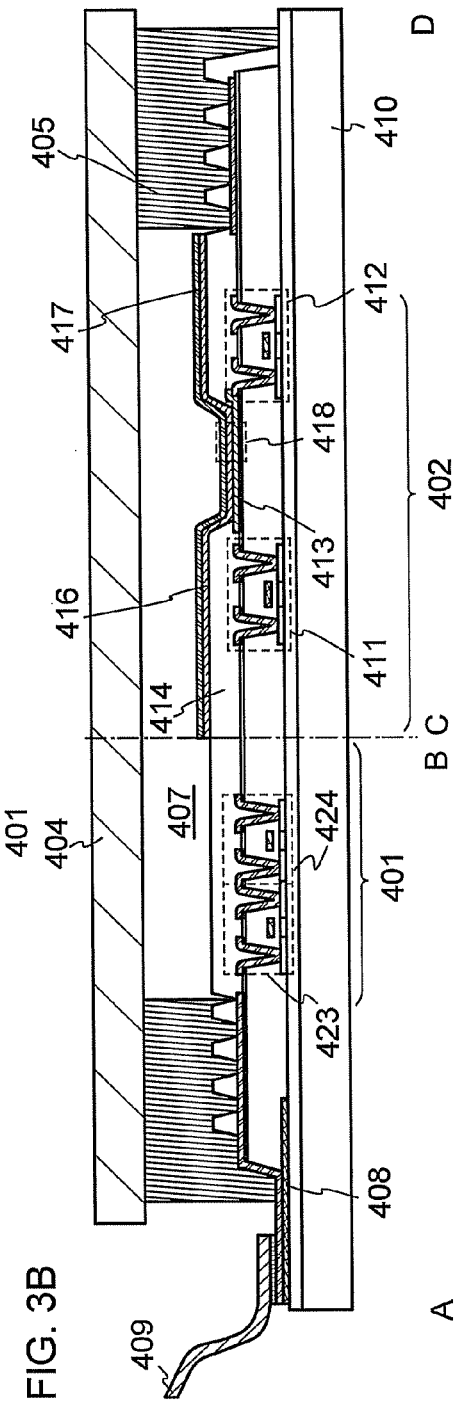

In Embodiment 5, a light-emitting device having a light-emitting element of one embodiment of the present invention will be described with reference to FIGS. 3A and 3B. FIG. 3A is a top view illustrating a light-emitting device, and FIG. 3B is a cross-sectional view taken along lines A-B and C-D of FIG. 3A.

In FIG. 3A, reference numeral 401 denotes a driver circuit portion (a source side driver circuit), reference numeral 402 denotes a pixel portion, and reference numeral 403 denotes a driver circuit portion (a gate side driver circuit), which are each indicated by dotted lines. Reference numeral 404 denotes a sealing substrate, reference numeral 405 denotes a sealant, and a portion enclosed by the sealant 405 is a space 407.

Note that a lead wiring 408 is a wiring for transmitting signals that are to be inputted to the source side driver circuit 401 and the gate side driver circuit 403, and receives a video signal, a clock signal, a start signal, a reset signal, and the like from a flexible printed circuit (FPC) 409 which serves as an external input terminal. Although only the FPC is illustrated here, a printed wiring board (PWB) may be attached to the FPC. The light-emitting device in this specification includes not only a light-emitting device itself but also a light-emitting device to which an FPC or a PWB is attached.

Next, a cross-sectional structure will be described with reference to FIG. 3B. The driver circuit portion and the pixel portion are formed over an element substrate 410. In this case, one pixel in the pixel portion 402 and the source side driver circuit 401 which is the driver circuit portion are illustrated.

A CMOS circuit which includes an n-channel TFT 423 and a p-channel TFT 424 is formed as the source side driver circuit 401. The driver circuit may be any of a variety of circuits formed using TFTs, such as a CMOS circuit, a PMOS circuit, or an NMOS circuit. Although a driver-integrated type in which a driver circuit is formed over the substrate is described in this embodiment, the present invention is not limited to this type, and the driver circuit can be formed outside the substrate.

The pixel portion 402 includes a plurality of pixels having a switching TFT 411, a current control TFT 412, and a first electrode 413 electrically connected to a drain of the current control TFT 412. Note that an insulator 414 is formed to cover an end portion of the first electrode 413. Here, the insulator 414 is formed by using a positive type photosensitive acrylic resin film.

In order to improve the coverage, the insulator 414 is provided such that either an upper end portion or a lower end portion of the insulator 414 has a curved surface with a curvature. For example, when positive photosensitive acrylic is used as a material for the insulator 414, only an upper end portion of the insulator 414 can have a curved surface with a radius of curvature (0.2 µm to 3 µm). Alternatively, for the insulator 414, either a negative type that becomes insoluble in an etchant by light irradiation or a positive type that becomes soluble in an etchant by light irradiation can be used.

A light-emitting layer 416 and a second electrode 417 are formed over the first electrode 413. Here, as a material for forming the first electrode 413 functioning as the anode, it is preferable to use a material having a high work function. For example, a single layer of an ITO film, an indium tin oxide film that includes silicon, an indium oxide film that includes 2 wt % to 20 wt % of zinc oxide, a titanium nitride film, a chromium film, a tungsten film, a Zn film, a Pt film, or the like, a stacked layer of a titanium nitride film and a film that mainly includes aluminum, a three-layer structure of a titanium nitride film, a film that mainly includes aluminum and a titanium nitride film, or the like can be used. Note that, when a stacked structure is employed, resistance of a wiring is low and a favorable ohmic contact is obtained.

In addition, the light-emitting layer 416 is formed by any of various methods such as an evaporation method using an evaporation mask, a droplet discharging method like an inkjet method, a printing method, and a spin coating method. The light-emitting layer 416 includes the heterocyclic compound described in Embodiment 1. Further, another material included in the light-emitting layer 416 may be a low molecular material, an oligomer, a dendrimer, a high molecular material, or the like.

As a material used for the second electrode 417 which is formed over the light-emitting layer 416 and serves as a cathode, it is preferable to use a material having a low work function (e.g., Al, Mg, Li, Ca, or an alloy or a compound thereof such as Mg—Ag, Mg—In, Al—Li, LiF, or $CaF_2$). In order that light generated in the light-emitting layer 416 be transmitted through the second electrode 417, the second electrode 417 may be formed of a stack of a metal thin film having a reduced thickness and a transparent conductive film (e.g., ITO, indium oxide containing 2 wt % to 20 wt % of zinc oxide, indium oxide-tin oxide that includes silicon or silicon oxide, or zinc oxide (ZnO)).

The sealing substrate 404 is attached to the element substrate 410 with the sealant 405; thus, a light-emitting element 418 is provided in the space 407 enclosed by the element substrate 410, the sealing substrate 404, and the sealant 405. Note that the space 407 is filled with filler such as an inert gas (e.g., nitrogen or argon) or the sealant 405.

Note that as the sealant 405, an epoxy-based resin is preferably used. Such a material used is desirably a material which does not transmit moisture or oxygen as possible. As a material for the sealing substrate 404, a glass substrate, a quartz substrate, or a plastic substrate including fiberglass-reinforced plastics (FRP), polyvinyl fluoride (PVF), polyester, acrylic, or the like can be used.

As described above, the active matrix light-emitting device having the light-emitting element of one embodiment of the present invention can be obtained.

Figure 4A:
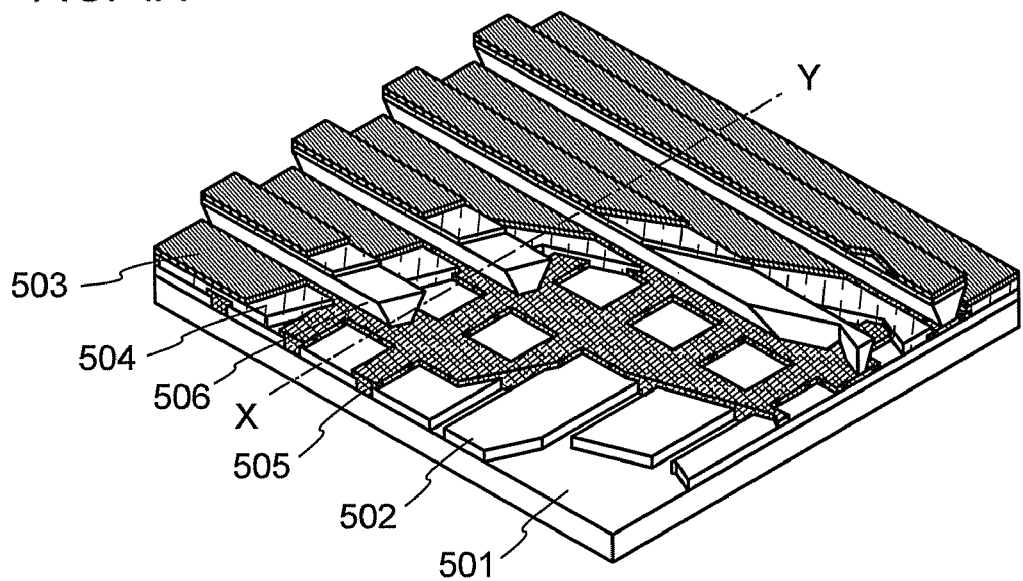
FIGS. 4A and 4B illustrate a light-emitting device of one embodiment of the present invention.
Figure 4B:
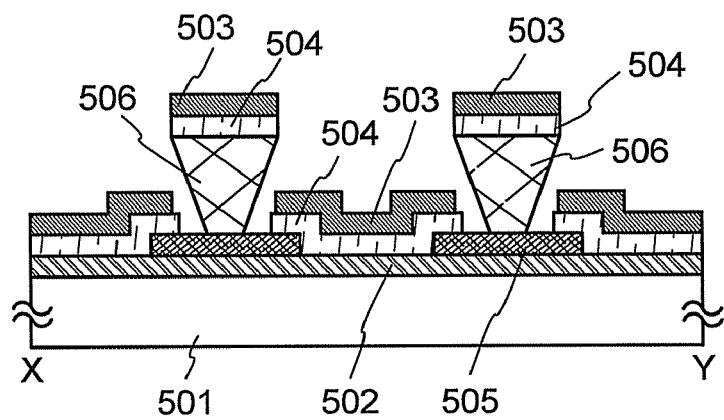

Further, the light-emitting element of the present invention can be used for a passive matrix light-emitting device as well as the above active matrix light-emitting device. FIGS. 4A and 4B illustrate a perspective view and a cross-sectional view of a passive matrix light-emitting device using the light-emitting element of the present invention. Note that FIG. 4A is a perspective view of the light-emitting device, and FIG. 4B is a cross-sectional view taken along line X-Y of FIG. 4A.

In FIGS. 4A and 4B, an EL layer 504 is provided between a first electrode 502 and a second electrode 503 over a substrate 501. An end portion of the first electrode 502 is covered with an insulating layer 505. In addition, a partition layer 506 is provided over the insulating layer 505. The sidewalls of the partition layer 506 are aslope so that a distance between both the sidewalls is gradually narrowed toward the surface of the substrate. In other words, a cross section taken along the direction of the short side of the partition layer 506 is trapezoidal, and the lower side (a side in contact with the insulating layer 505) is shorter than the upper side (a side not in contact with the insulating layer 505). By provision of the partition layer 506 in such a manner, a defect of the light-emitting element due to static electricity or the like can be prevented.

Thus, the passive matrix light-emitting device having the light-emitting element of one embodiment of the present invention can be obtained.

The light-emitting devices described in this embodiment (the active matrix light-emitting device and the passive matrix light-emitting device) are both formed using the light-emitting element of one embodiment of the present invention, thereby having low power consumption.

Note that this embodiment can be combined with any other embodiment as appropriate.

Embodiment 6

Embodiment 6 will give descriptions of electronic devices and lighting devices including the light-emitting device of one embodiment of the present invention described in Embodiment 5 as a part. Examples of the electronic devices include cameras such as video cameras and digital cameras, goggle type displays, navigation systems, audio reproducing devices (e.g., car audio systems and audio systems), computers, game machines, portable information terminals (e.g., mobile computers, cellular phones, portable game machines, and electronic books), image reproducing devices in which a recording medium is provided (specifically, devices that are capable of reproducing recording media such as digital versatile discs (DVDs) and provided with a display device that can display an image), and the like. Specific examples of these electronic devices are illustrated in FIGS. 5A to 5D.

Figure 5A:
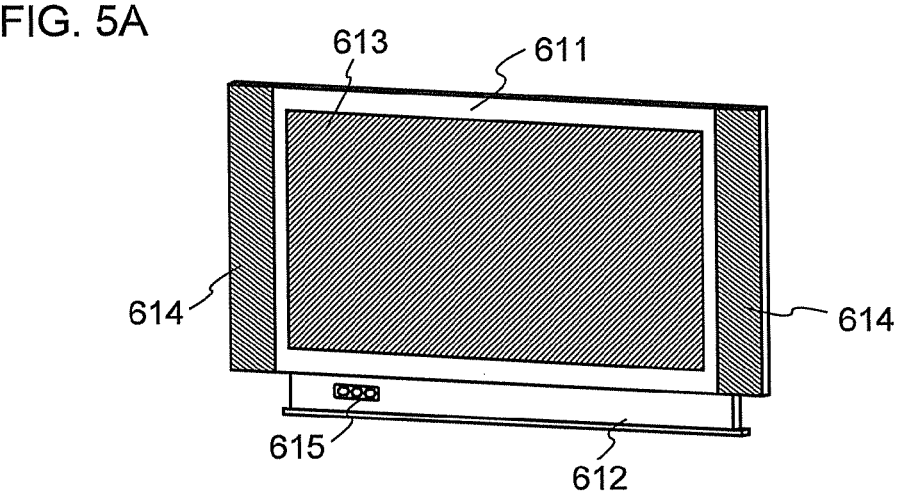
FIGS. 5A to 5D each illustrate an electronic device of one embodiment of the present invention.

FIG. 5A illustrates a television set according to one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention has high current efficiency, a television set having reduced power consumption can be obtained by application of the light-emitting device of one embodiment of the present invention.

Figure 5B:
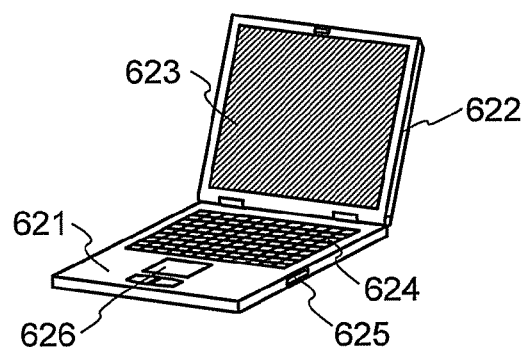

FIG. 5B illustrates a computer according to one embodiment of the present invention, which includes a main body 621, a housing 622, a display portion 623, a keyboard 624, an external connection port 625, a pointing device 626, and the like. In this computer, the light-emitting device of the present invention can be applied to the display portion 623. Since the light-emitting device of one embodiment of the present invention has high current efficiency, a computer having reduced power consumption can be obtained by application of the light-emitting device of one embodiment of the present invention.

Figure 5C:
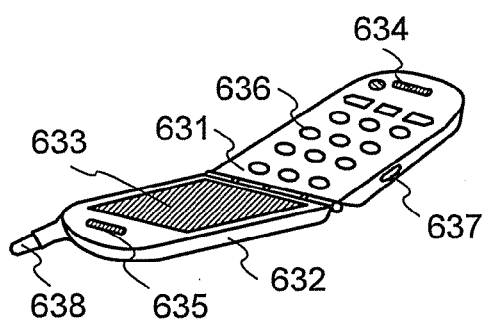

FIG. 5C illustrates a cellular phone of one embodiment of the present invention, which includes a main body 631, a housing 632, a display portion 633, an audio input portion 634, an audio output portion 635, operation keys 636, an external connection port 637, an antenna 638, and the like. In this cellular phone, the light-emitting device of the present invention can be applied to the display portion 633. Since the light-emitting device of one embodiment of the present invention has high current efficiency, a cellular phone having reduced power consumption can be obtained by application of the light-emitting device of one embodiment of the present invention.

Figure 5D:
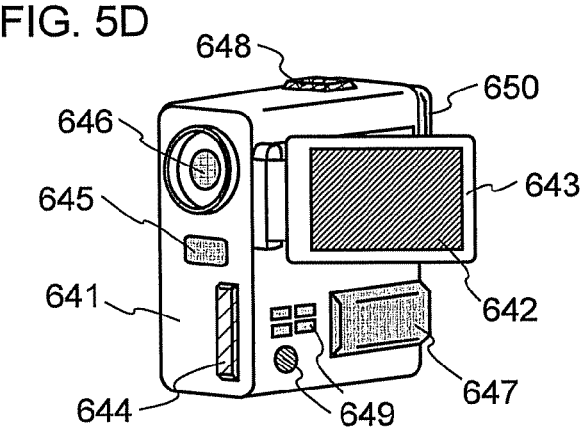

FIG. 5D illustrates a camera of one embodiment of the present invention, which includes a main body 641, a display portion 642, a housing 643, an external connection port 644, a portion 645 for receiving signals from a remote control, an image receiving portion 646, a battery 647, an audio input portion 648, operation keys 649, an eyepiece portion 650, and the like. In this camera, the light-emitting device of one embodiment of the present invention can be applied to the display portion 642. Since the light-emitting device of one embodiment of the present invention has high current efficiency, a camera having reduced power consumption can be obtained by application of the light-emitting device of one embodiment of the present invention.

As thus described, application range of the light-emitting device of one embodiment of the present invention is quite wide, and this light-emitting device can be applied to electronic devices of a variety of fields. With use of the light-emitting device of one embodiment of the present invention, an electronic device having reduced power consumption can be obtained.

Figure 6:
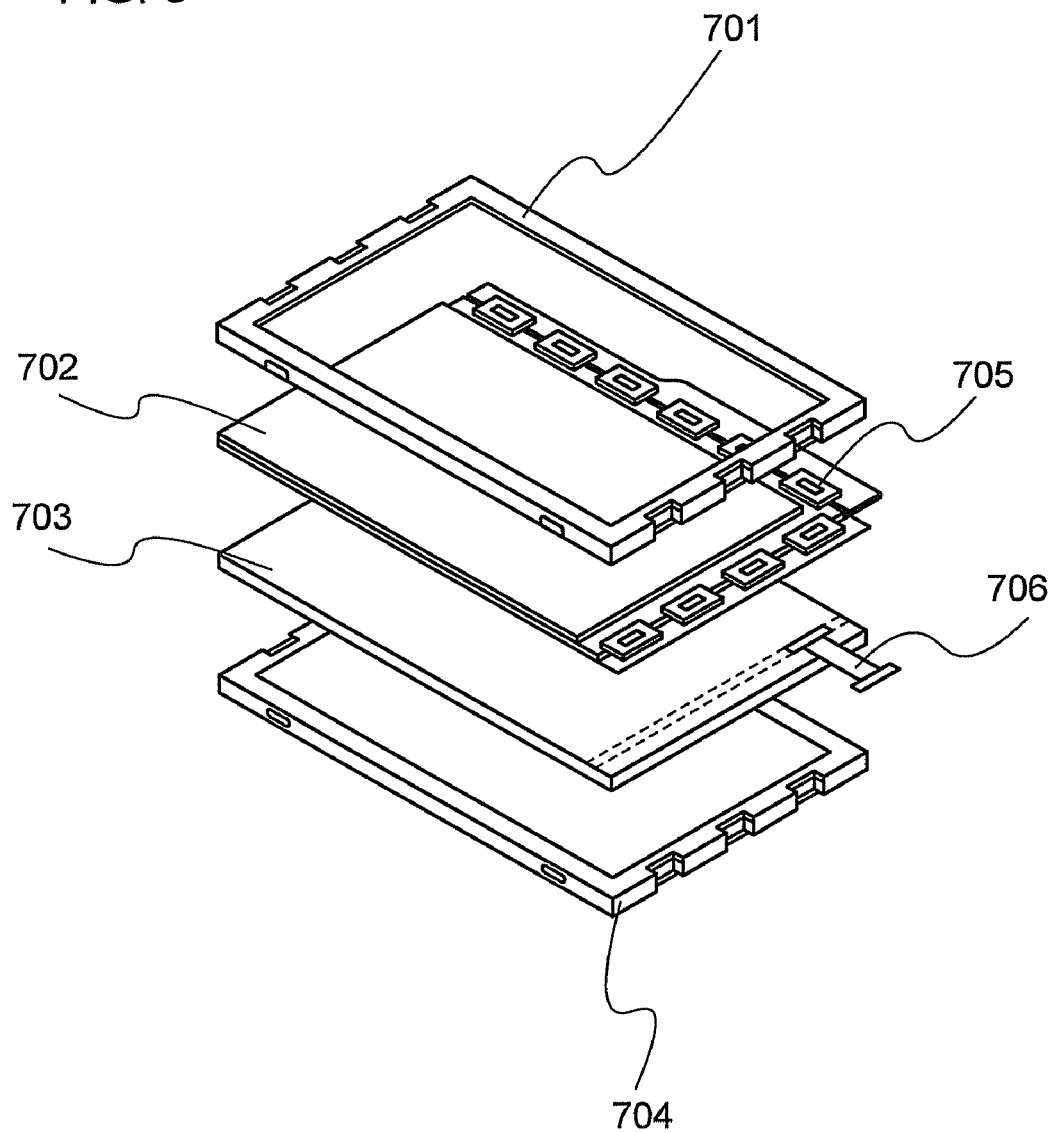
FIG. 6 illustrates a liquid crystal display device according to one embodiment of one embodiment of the present invention.

Moreover, the light-emitting device of one embodiment of the present invention can be used as a lighting device. FIG. 6 illustrates an example of a liquid crystal display device using the light-emitting device of one embodiment of the present invention as a backlight. The liquid crystal display device illustrated in FIG. 6 includes a housing 701, a liquid crystal layer 702, a backlight 703, and a housing 704. The liquid crystal layer is electrically connected to a driver IC 705. The light-emitting device of one embodiment of the present invention is used as the backlight 703, and a current is supplied to the backlight 703 through a terminal 706.

By using the light-emitting device of one embodiment of the present invention as a backlight of a liquid crystal display device as described above, a backlight having reduced power consumption can be obtained. Moreover, since the light-emitting device of one embodiment of the present invention is a lighting device for planar light emission and the enlargement of the light-emitting device is possible, the backlight can be made larger. Thus, a larger-area liquid crystal display device having reduced power consumption can be obtained.

Figure 7:
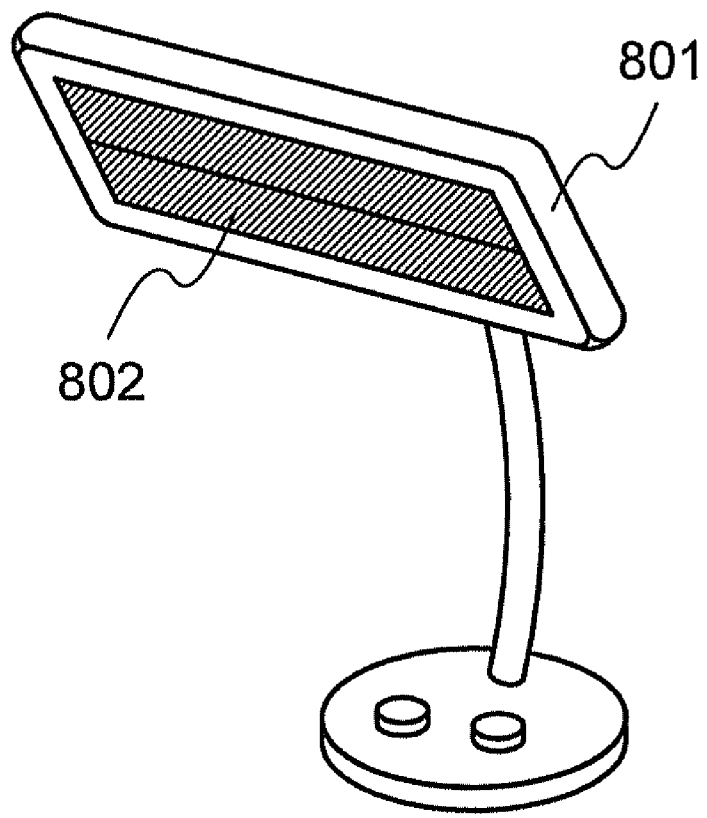
FIG. 7 illustrates a lighting device according to one embodiment of the present invention.

FIG. 7 illustrates an example in which the light-emitting device of one embodiment of the present invention is used for a desk lamp which is a lighting device. The desk lamp illustrated in FIG. 7 has a housing 801 and a light source 802, and the light-emitting device of one embodiment of the present invention is used as the light source 802. The light-emitting device of one embodiment of the present invention includes the light-emitting element having high current efficiency, whereby a desk lamp having reduced power consumption can be obtained.

Figure 8:
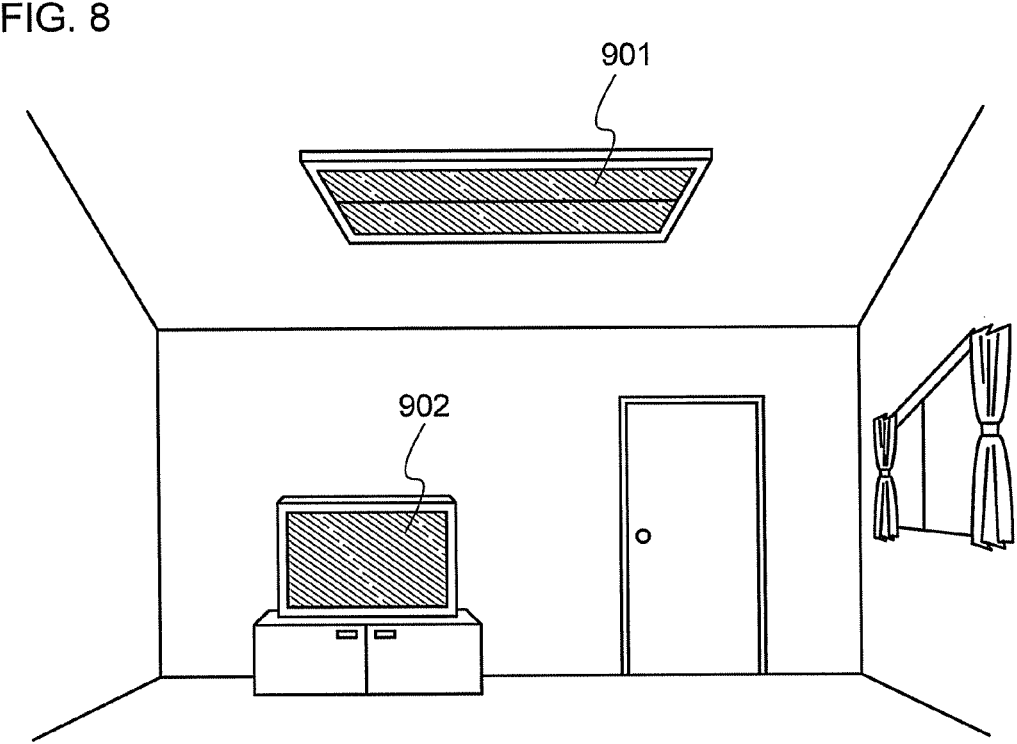
FIG. 8 illustrates a lighting device according to one embodiment of the present invention.

FIG. 8 illustrates an example in which the light-emitting device of one embodiment of the present invention is used for an indoor lighting device 901. Since the light-emitting device of one embodiment of the present invention can have a larger area, the light-emitting device of one embodiment of the present invention can be used as a lighting device having a large area. Further, the light-emitting device of one embodiment of the present invention includes the light-emitting element having high current efficiency, whereby a lighting device having reduced power consumption can be obtained. In a room where the light-emitting device of one embodiment of the present invention is used as the indoor lighting device 901 as above, a television set 902 of one embodiment of the present invention as described referring to FIG. 5A can be installed so that pubic broadcasting and movies can be watched.

Note that this embodiment can be combined with any other embodiment as appropriate.

Example 1

This example will give descriptions of a method of synthesizing 2-[4-(dibenzothiophen-4-yl)phenyl]-1-phenyl-1H- benzimidazole (abbreviation: DBTBIm-II) represented by the following Structural formula (108).

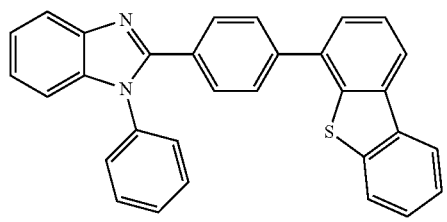

(108)

Synthesis of 2-[4-(dibenzothiophen-4-yl)phenyl]-1-phenyl-1H-benzimidazole (abbreviation: DBTBIm-II)

The synthesis scheme of 2-[4-(dibenzothiophen-4-yl)phenyl]-1-phenyl-1H-benzimidazole (abbreviation: DBTBIm-II) is illustrated in (B-1).

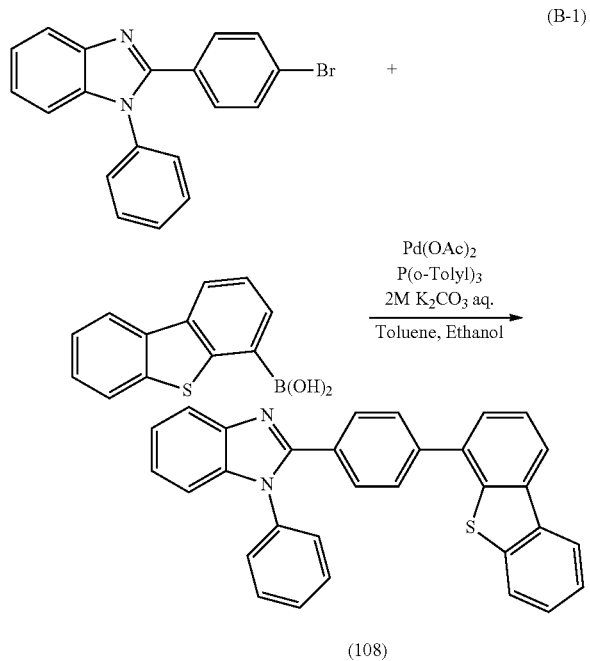

(B-1)

(108)

In a 500-mL three-neck flask were put 5.1 g (15 mmol) of 2-(4-bromophenyl)-1-phenyl-1H-benzimidazole, 3.7 g (16 mmol) of dibenzothiophen-4-boronic acid, and 0.2 g (0.7 mmol) of tri(ortho-tolyl)phosphine. The air in the flask was replaced with nitrogen. To this mixture were added 16 mL of a 2.0 mmol/L aqueous solution of potassium carbonate, 55 mL of toluene, and 18 mL of ethanol. Under reduced pressure, this mixture was stirred to be degassed. Then, 33 mg (0.2 mmol) of palladium(II) acetate was added to this mixture, and the mixture was stirred at 80° C. for 6 hours under a nitrogen stream.

After a predetermined time, water was added to the obtained mixture, and the aqueous layer was extracted with chloroform. The extracted solution and the organic layer were combined and washed with saturated brine, followed by drying with magnesium sulfate. This mixture was gravity filtered. The resulting filtrate was concentrated to give an oily substance. This oily substance was purified by silica gel column chromatography. The silica gel column chromatography was carried out using toluene as a developing solvent. The obtained fractions were concentrated to give a solid. Hexane was added to this solid, followed by irradiation with ultrasonic waves. Suction filtration was carried out, whereby 5.8 g of a white powder was obtained in 88% yield, which was the substance to be produced.

By a train sublimation method, 2.8 g of the obtained white powder was purified. In the purification, the white powder was heated at 235° C. under a pressure of 2.4 Pa with a flow rate of argon gas of 5 mL/min. After the purification, 2.2 g of a pale yellow glassy solid was obtained in a yield of 79%, which was the substance to be produced.

A nuclear magnetic resonance (NMR) method identified this compound as 2-[4-(dibenzothiophen-4-yl)phenyl]-1-phenyl-1H-benzimidazole (abbreviation: DBTBIm-II), which was the substance to be produced.

$^1$H NMR data of the obtained substance are as follows: $^1$H NMR (CDCl$_3$, 300 MHz): δ (ppm)=7.27-7.30 (m, 2H), 7.32-7.60 (m, 10H), 7.67-7.75 (m, 4H), 7.82-7.85 (m, 1H), 7.83 (dd, J=8.4 Hz, 1.5 Hz, 1H), 8.13-8.19 (m, 2H).

Figure 9A:
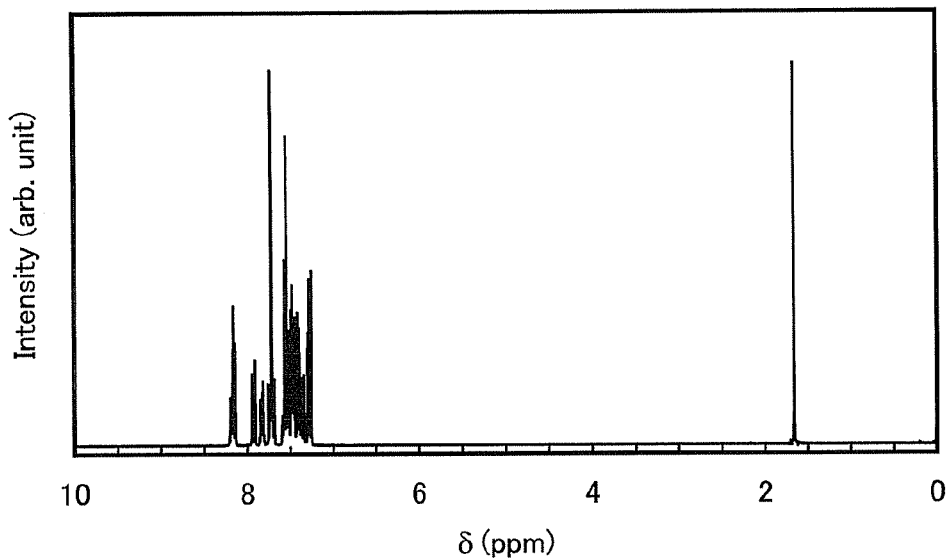
FIGS. 9A and 9B illustrate $^1$H NMR charts of 2-[4-(dibenzothiophen-4-yl)phenyl]-1-phenyl-1H-benzimidazole.
Figure 9B:
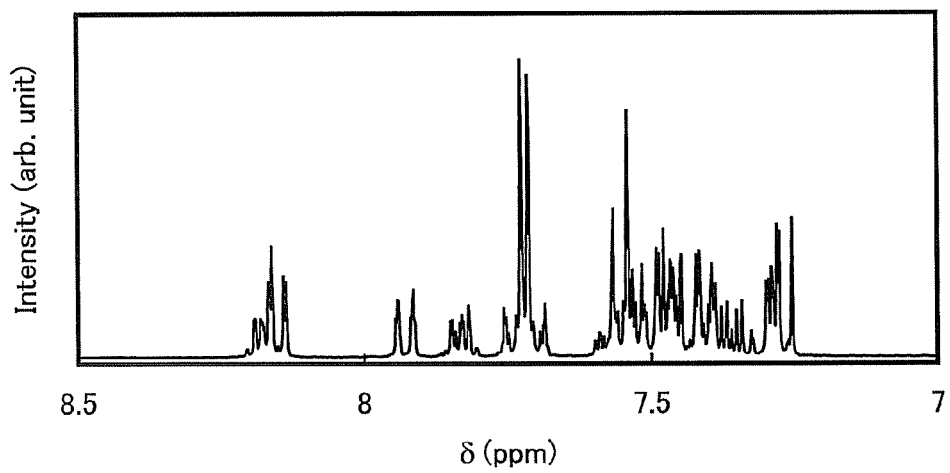

FIGS. 9A and 9B illustrate the $^1$H NMR charts. Note that FIG. 9B is a chart showing an enlarged part of FIG. 9A in the range of 7.0 ppm to 8.5 ppm.

Figure 10A:
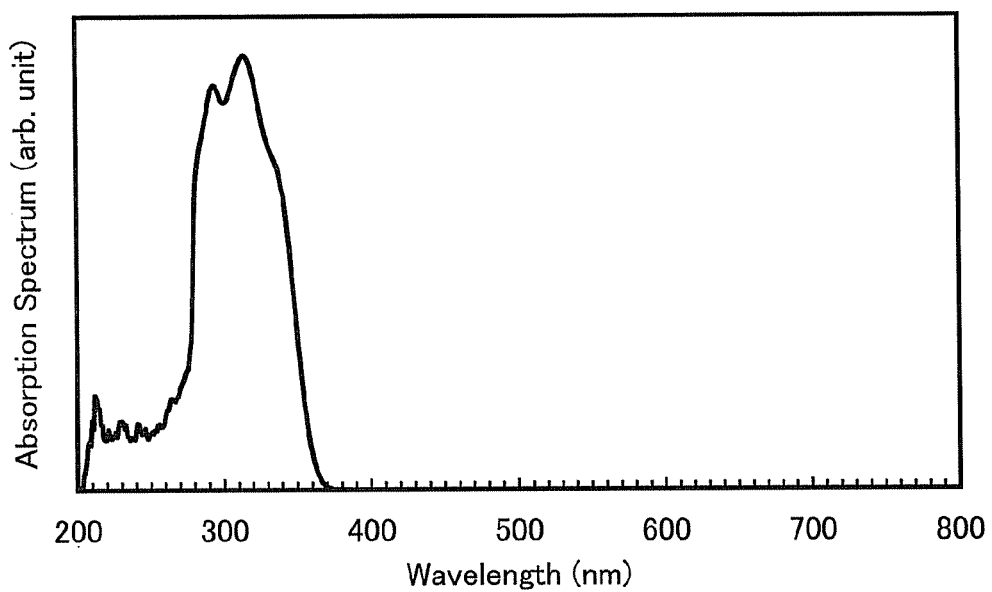
FIGS. 10A and 10B illustrate respectively an absorption spectrum and an emission spectrum of a toluene solution of 2-[4-(dibenzothiophen-4-yl)phenyl]-1-phenyl-1H-benzimidazole.
Figure 10B:
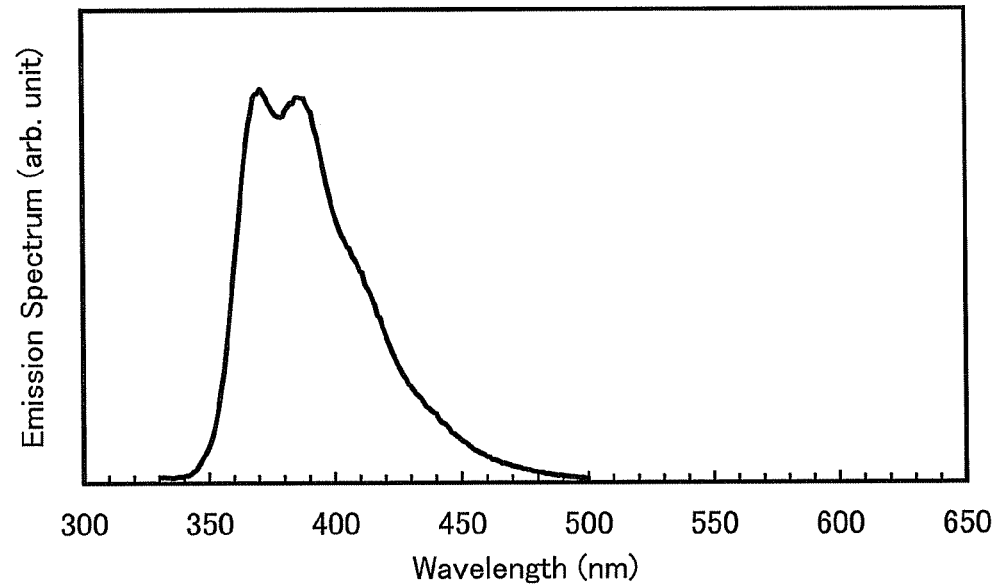
Figure 11A:
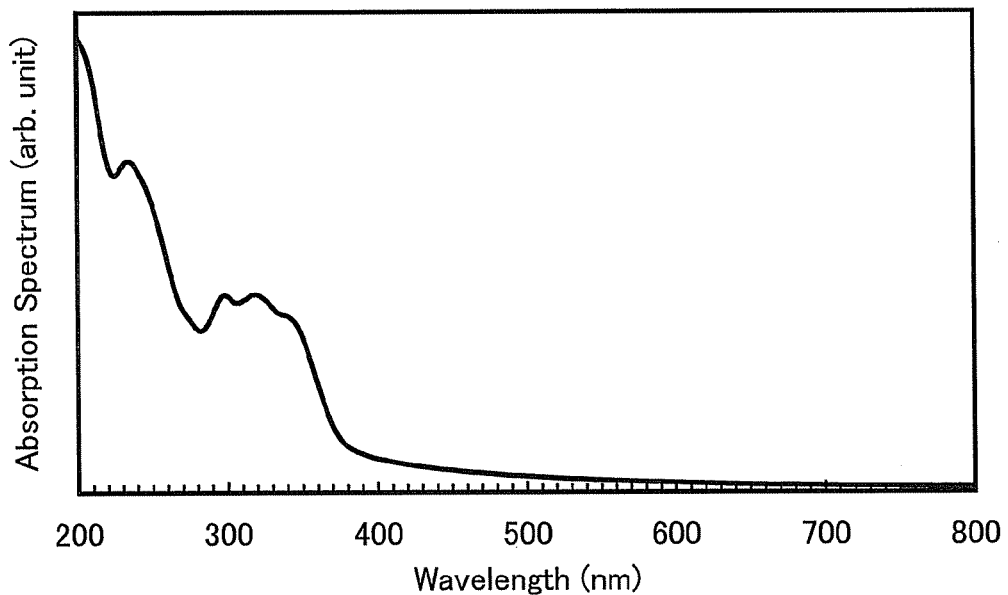
FIGS. 11A and 11B illustrate respectively an absorption spectrum and an emission spectrum of a thin film of 2-[4-(dibenzothiophen-4-yl)phenyl]-1-phenyl-1H-benzimidazole.
Figure 11B:
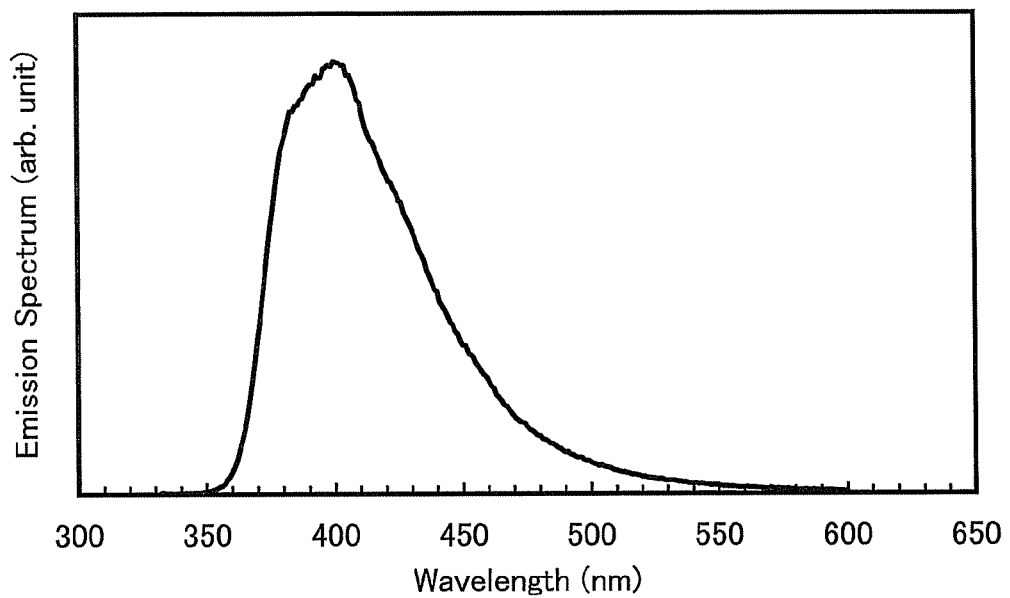

Further, FIG. 10A shows an absorption spectrum of a toluene solution of DBTBIm-II, and FIG. 10B shows an emission spectrum thereof. FIG. 11A shows an absorption spectrum of a thin film of DBTBIm-II, and FIG. 11B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 10A and 10B and FIGS. 11A and 11B, the horizontal axis represents wavelength (nm) and the vertical axis represents intensity (arbitrary unit). In the case of the toluene solution, absorption peaks were observed at around 294 nm, 315 nm, and 337 nm, and emission wavelength peaks were 371 nm and 386 nm (excitation wavelength: 315 nm). In the case of the thin film, absorption peaks were observed at around 234 μm, 298 nm, 319 nm, and 338 nm, and an emission wavelength peak was 401 nm (excitation wavelength: 316 nm).

Example 2

This example will give descriptions of a method of synthesizing 2-[3-(dibenzothiophen-4-yl)phenyl]-1-phenyl-1H-benzimidazole (abbreviation: mDBTBIm-II) represented by the following Structural formula (224).

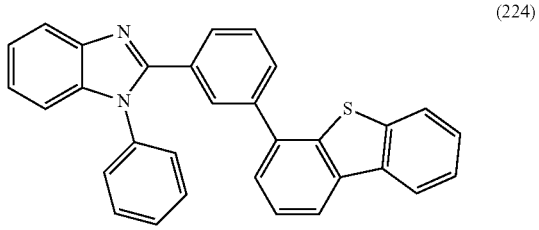 [SMILES: c1ccc(-n2c(-c3cccc(-c4cccc5c4sc4ccccc45)c3)nc3ccccc32)cc1]

(224)

Synthesis of 2-[3-(dibenzothiophen-4-yl)phenyl]-1-phenyl-1H-benzimidazole (abbreviation: mDBT-BIm-II)

The synthesis scheme of 2-[3-(dibenzothiophen-4-yl)phenyl]-1-phenyl-1H-benzimidazole (abbreviation: mDBTBIm-II) is illustrated in (B-2).

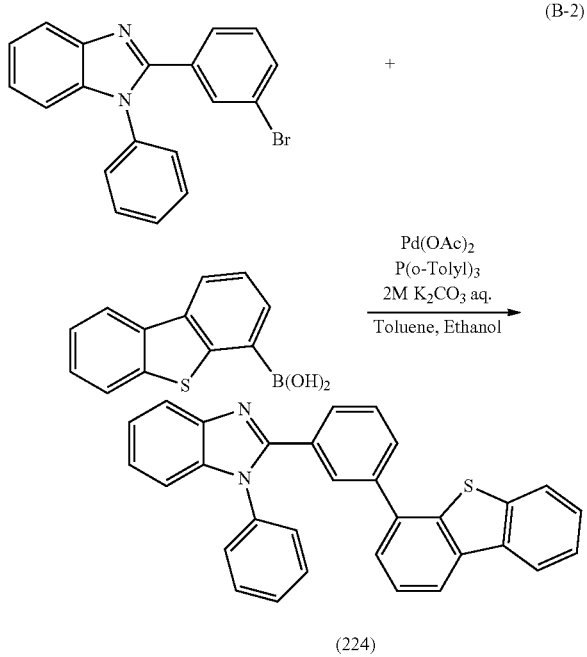

(B-2)

(224)

In a 50-mL three-neck flask were put 1.2 g (3.3 mmol) of 2-(3-bromophenyl)-1-phenyl-1H-benzimidazole, 0.8 g (3.3 mmol) of dibenzothiophen-4-boronic acid, and 50 mg (0.2 mmol) of tri(ortho-tolyl)phosphine. The air in the flask was replaced with nitrogen. To this mixture were added 3.3 mL of a 2.0 mmol/L aqueous solution of potassium carbonate, 12 mL of toluene, and 4 mL of ethanol. Under reduced pressure, this mixture was stirred to be degassed. Then, 7.4 mg (33 μmol) of palladium(II) acetate was added to this mixture, and the mixture was stirred at 80° C. for 6 hours under a nitrogen stream.

After a predetermined time, the aqueous layer of the obtained mixture was extracted with toluene. The extracted solution and the organic layer were combined and washed with saturated brine, followed by drying with magnesium sulfate. This mixture was separated by gravity filtration, and the filtrate was concentrated to give an oily substance. This oily substance was purified by silica gel column chromatography. The silica gel column chromatography was carried out using toluene as a developing solvent. The obtained fractions were concentrated to give an oily substance. This oily substance was purified by high performance liquid chromatography. The high performance liquid chromatography was performed using chloroform as a developing solvent. The obtained fractions were concentrated to give an oily substance. Recrystallization of this oily substance from a mixed solvent of toluene and hexane gave 0.8 g of a pale yellow powder in 51% yield, which was the substance to be produced.

By a train sublimation method, 0.8 g of the obtained pale yellow powder was purified. In the purification, the pale yellow powder was heated at 215° C. under a pressure of 3.0 Pa with a flow rate of argon gas of 5 mL/min. After the purification, 0.6 g of a white powder was obtained in a yield of 82%, which was the substance to be produced.

A nuclear magnetic resonance (NMR) method identified this compound as 2-[3-(dibenzothiophen-4-yl)phenyl]-1-phenyl-1H-benzimidazole (abbreviation: mDBTBIm-II), which was the substance to be produced.

$^1$H NMR data of the obtained compound are as follows: $^1$H NMR (CDCl$_3$, 300 MHz): δ (ppm)=7.23-7.60 (m, 13H), 7.71-7.82 (m, 3H), 7.90-7.92 (m, 2H), 8.10-8.17 (m, 2H).

Figure 12A:
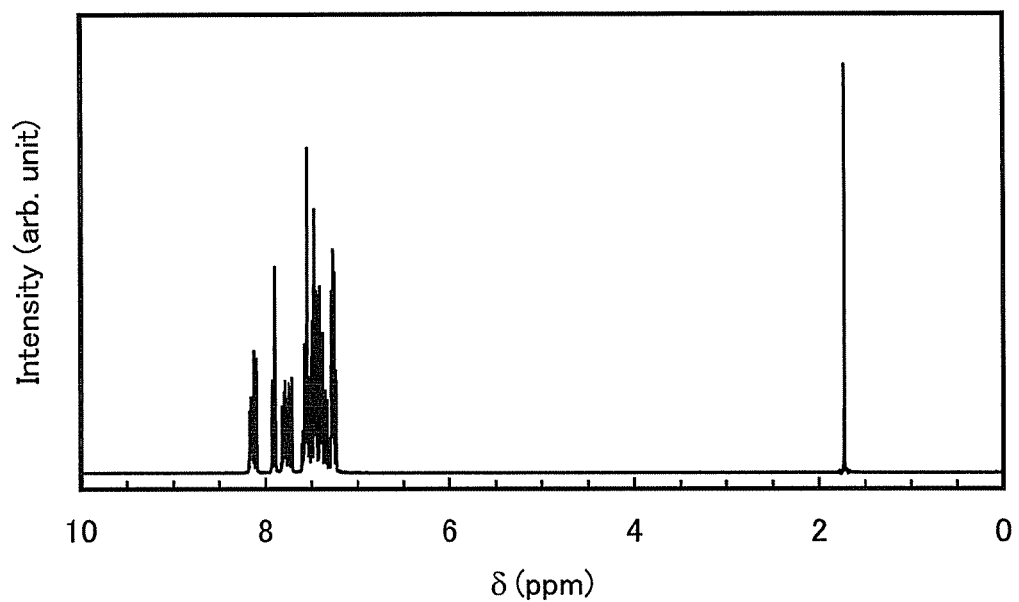
FIGS. 12A and 12B illustrate $^1$H NMR charts of 2-[3-(dibenzothiophen-4-yl)phenyl]-1-phenyl-1H-benzimidazole.
Figure 12B:
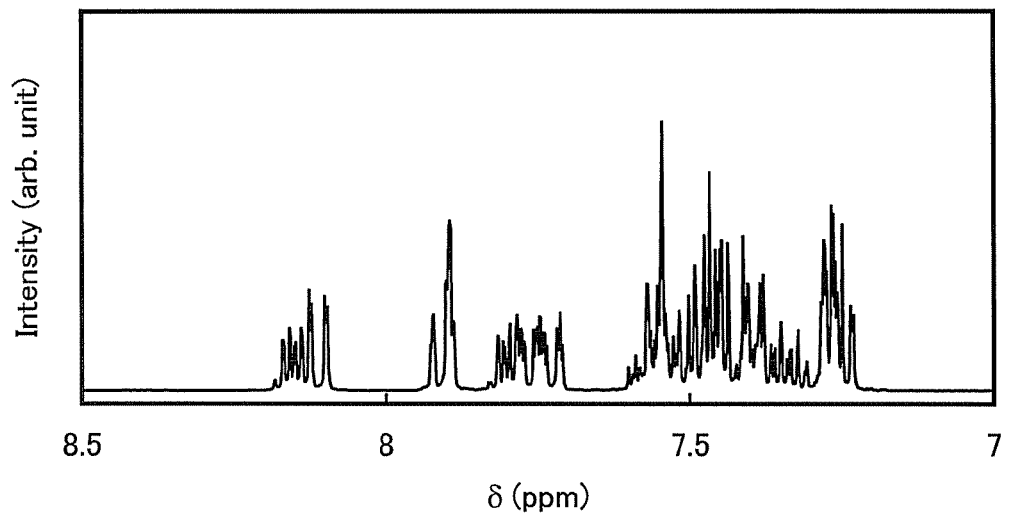

FIGS. 12A and 12B illustrate the $^1$H NMR charts. Note that FIG. 12B is a chart showing an enlarged part of FIG. 12A in the range of 7.0 ppm to 8.5 ppm.

Figure 13A:
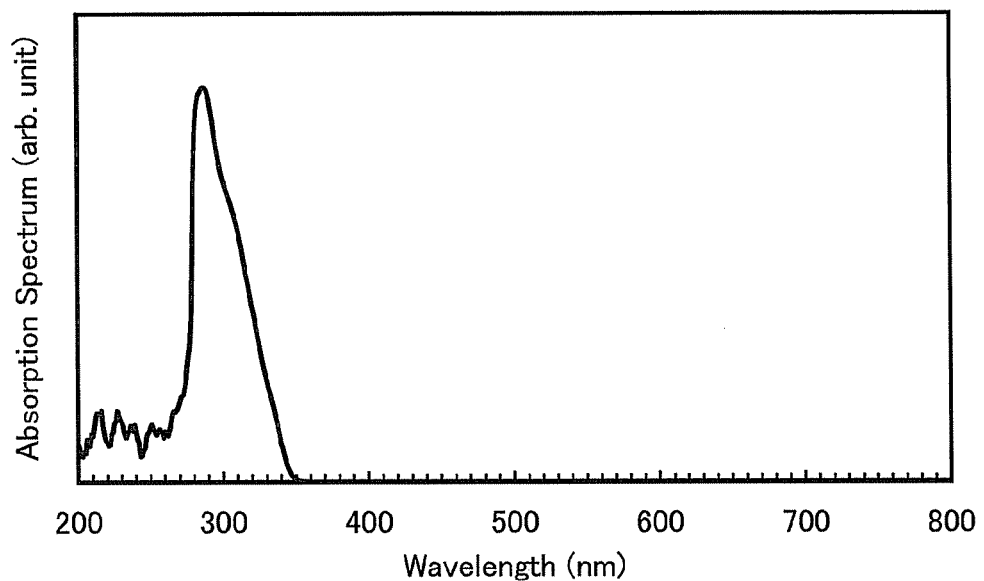
FIGS. 13A and 13B illustrate respectively an absorption spectrum and an emission spectrum of a toluene solution of 2-[3-(dibenzothiophen-4-yl)phenyl]-1-phenyl-1H-benzimidazole.
Figure 13B:
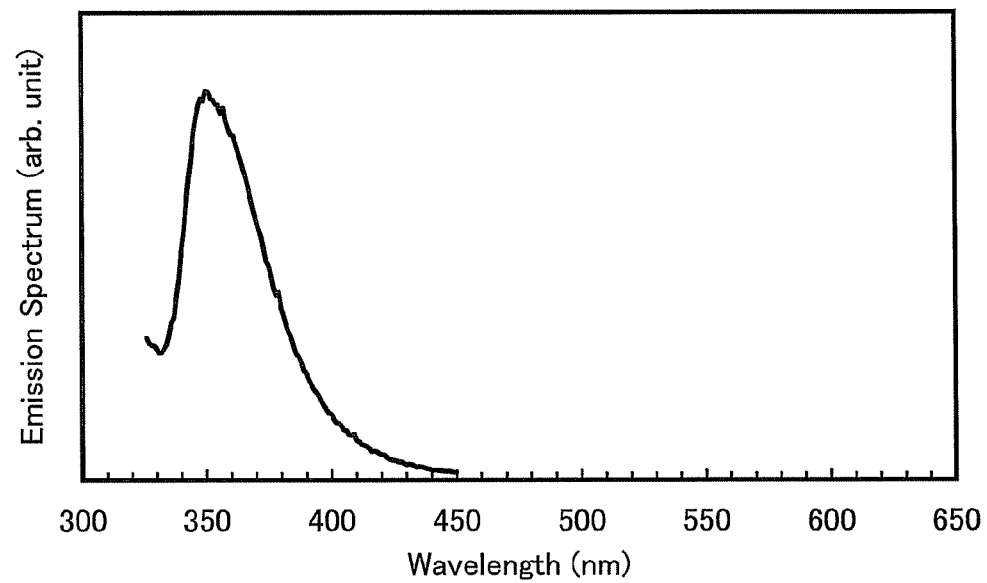
Figure 14A:
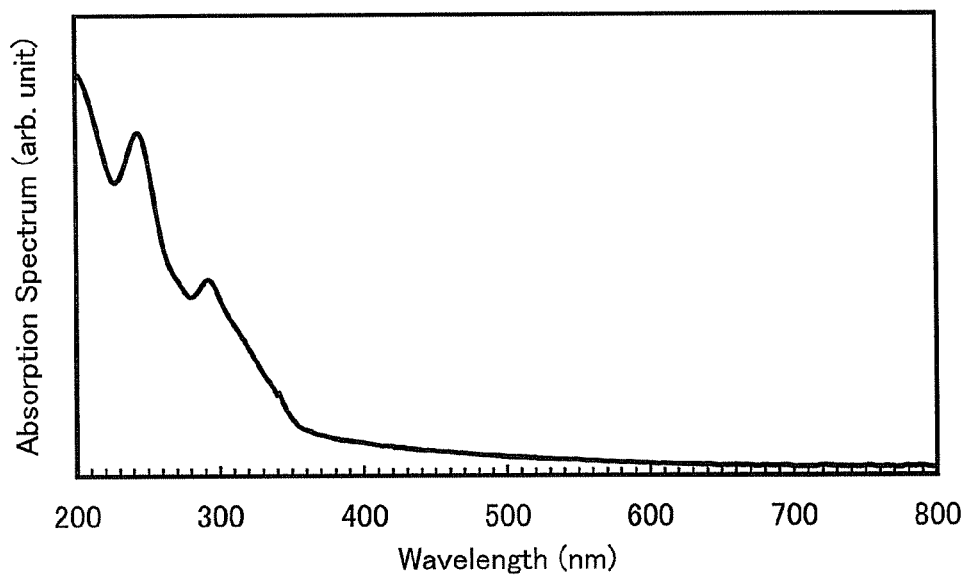
FIGS. 14A and 14B illustrate respectively an absorption spectrum and an emission spectrum of a thin film of 2-[3-(dibenzothiophen-4-yl)phenyl]-1-phenyl-1H-benzimidazole.
Figure 14B:
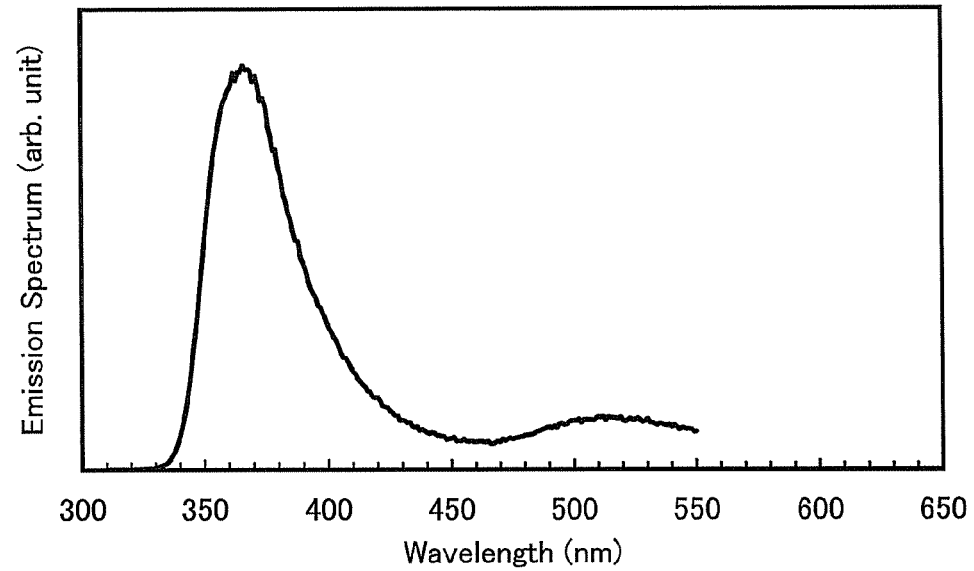

Further, FIG. 13A shows an absorption spectrum of a toluene solution of mDBTBIm-II, and FIG. 13B shows an emission spectrum thereof. FIG. 14A shows an absorption spectrum of a thin film of mDBTBIm-II, and FIG. 14B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 13A and 13B and FIGS. 14A and 14B, the horizontal axis represents wavelength (nm) and the vertical axis represents intensity (arbitrary unit). In the case of the toluene solution, absorption peaks were observed at around 287 nm and 302 nm, and an emission wavelength peak was 353 nm (excitation wavelength: 287 nm). In the case of the thin film, absorption peaks were observed at around 243 nm and 292 nm, and an emission wavelength peak was 367 nm (excitation wavelength: 292 nm).

Example 3

This example will give descriptions of a method of synthesizing 2-[4-(2,8-diphenyldibenzothiophen-4-yl)phenyl]-1-phenyl-1H-benzimidazole (abbreviation: DBTBIm-III) represented by the following Structural formula (189).

(189)

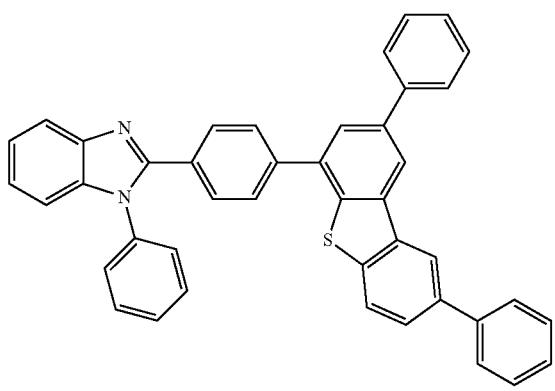

Synthesis of 2-[4-(2,8-diphenyldibenzothiophen-4-yl)phenyl]-1-phenyl-1H-benzimidazole (abbreviation: DBTBIm-III)

The synthesis scheme of 2-[4-(2,8-diphenyldibenzothiophen-4-yl)phenyl]-1-phenyl-1H-benzimidazole (abbreviation: DBTBIm-III) is illustrated in (B-3).

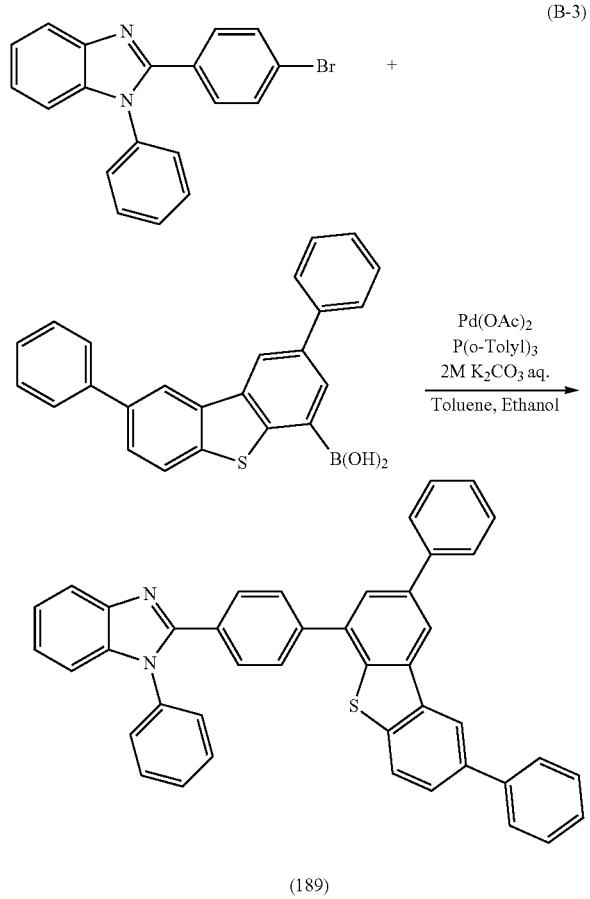

(B-3)

(189)

In a 50-mL three-neck flask were put 1.8 g (5.0 mmol) of 2-(4-bromophenyl)-1-phenyl-1H-benzimidazole, 2.2 g (5.8 mmol) of 2,8-diphenyldibenzothiophen-4-boronic acid, and 76 mg (0.2 mmol) of tri(ortho-tolyl)phosphine. The air in the flask was replaced with nitrogen. To this mixture were added 5.8 mL of a 2.0 mmol/L aqueous solution of potassium carbonate, 19 mL of toluene, and 6 mL of ethanol. Under reduced pressure, this mixture was stirred to be degassed. Then, 11 mg (50 μmol) of palladium(II) acetate was added to this mixture, and the mixture was stirred at 80° C. for 4 hours under a nitrogen stream.

After a predetermined time, the aqueous layer of the obtained mixture was extracted with chloroform. The extracted solution and the organic layer were combined and washed with saturated brine, followed by drying with magnesium sulfate. This mixture was separated by gravity filtration, and the filtrate was concentrated to give an oily substance. This oily substance was purified by silica gel column chromatography. The chromatography was carried out using toluene as a developing solvent. The obtained fractions were concentrated to give an oily substance. Recrystallization of this oily substance from a mixed solvent of toluene and hexane gave 1.9 g of a pale yellow powder in 63% yield, which was the substance to be produced.

By a train sublimation method, 1.9 g of the obtained yellow powder was purified. In the purification, the yellow powder was heated at 310° C. under a pressure of 2.0 Pa with a flow rate of argon gas of 5 mL/min. After the purification, 1.5 g of a white glassy solid was obtained in a yield of 80%, which was the substance to be produced.

The nuclear magnetic resonance (NMR) measurement identified this compound as 2-[4-(2,8-diphenyldibenzothiophen-4-yl)phenyl]-1-phenyl-1H-benzimidazole (abbreviation: DBTBIm-III).

$^1$H NMR data of the obtained compound are as follows: $^1$H NMR (CDCl$_3$, 300 MHz): δ (ppm)=7.27-7.31 (m, 2H), 7.33-7.61 (m, 12H), 7.70-7.77 (m, 10H), 7.88-7.95 (m, 2H), 8.42 (dd, J=6.6 Hz, 1.5 Hz, 2H).

Figure 15A:
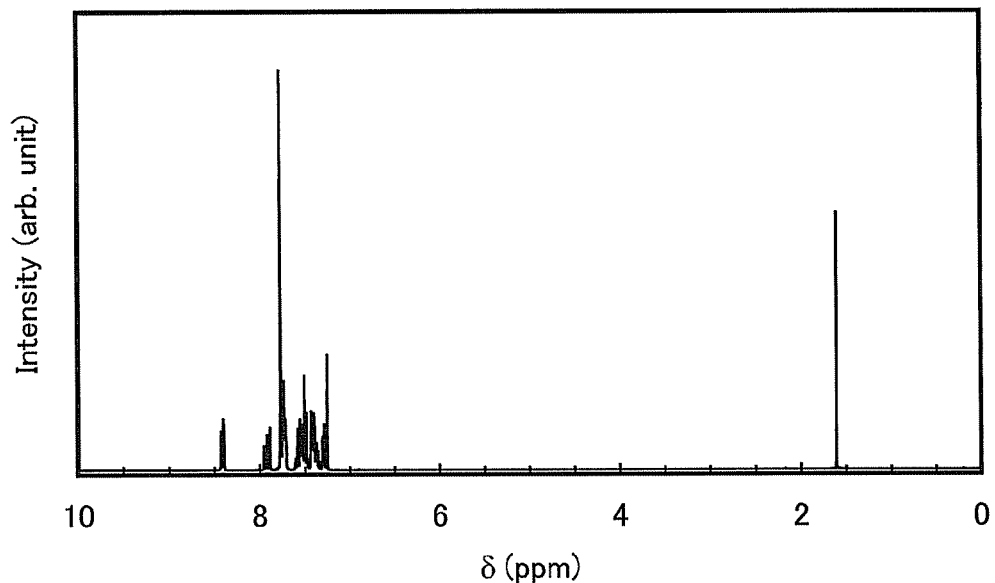
FIGS. 15A and 15B illustrate $^1$H NMR charts of 2-[4-(2,8-diphenyldibenzothiophen-4-yl)phenyl]-1-phenyl-1H-benzimidazole.
Figure 15B:
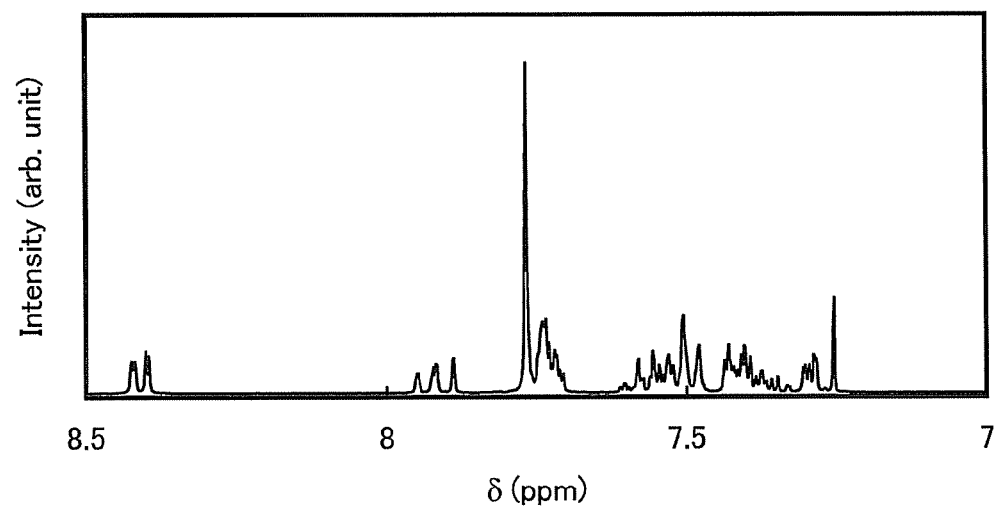

FIGS. 15A and 15B illustrate the $^1$H NMR charts. Note that FIG. 15B is a chart showing an enlarged part of FIG. 15A in the range of 7.0 ppm to 8.5 ppm.

Figure 16A:
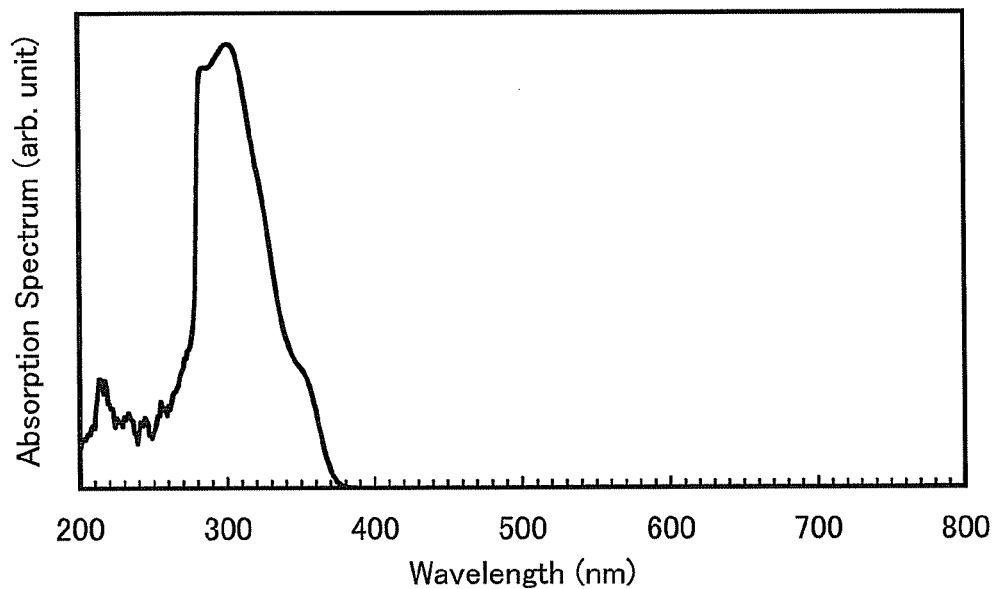
FIGS. 16A and 16B illustrate respectively an absorption spectrum and an emission spectrum of a toluene solution of 2-[4-(2,8-diphenyldibenzothiophen-4-yl)phenyl]-1-phenyl-1H-benzimidazole.
Figure 16B:
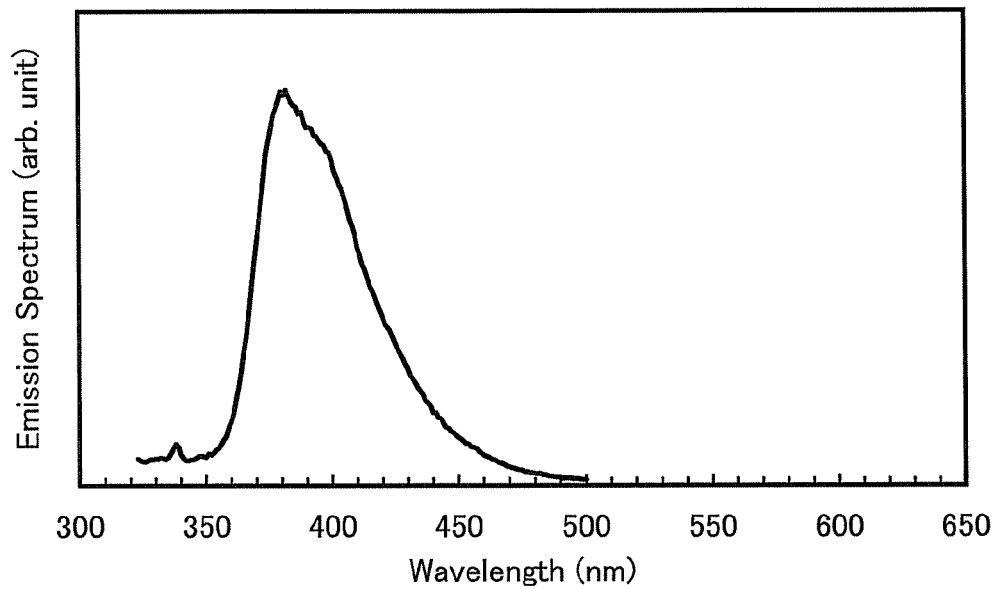
Figure 17A:
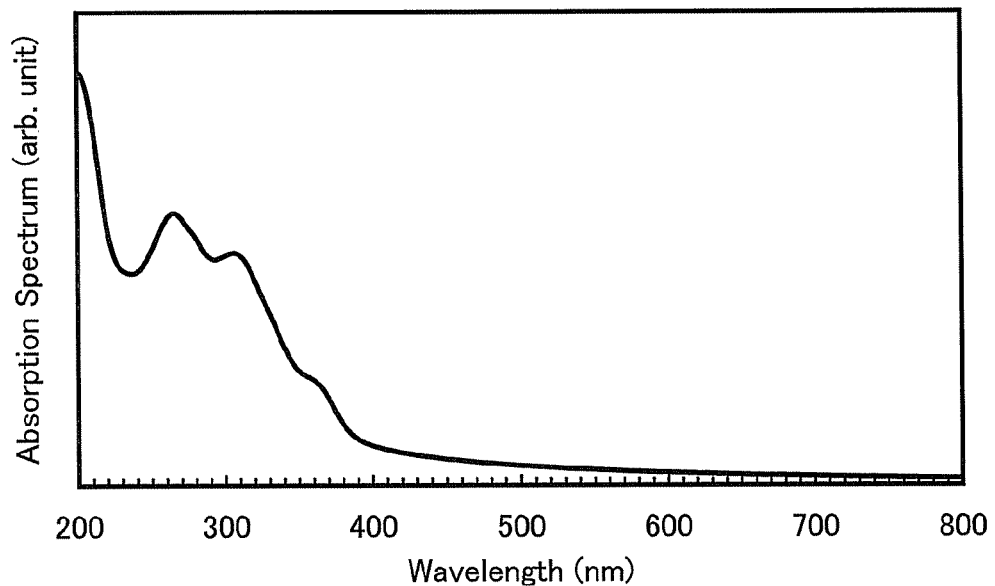
FIGS. 17A and 17B illustrate respectively an absorption spectrum and an emission spectrum of a thin film of 2-[4-(2,8-diphenyldibenzothiophen-4-yl)phenyl]-1-phenyl-1H-benzimidazole.
Figure 17B:
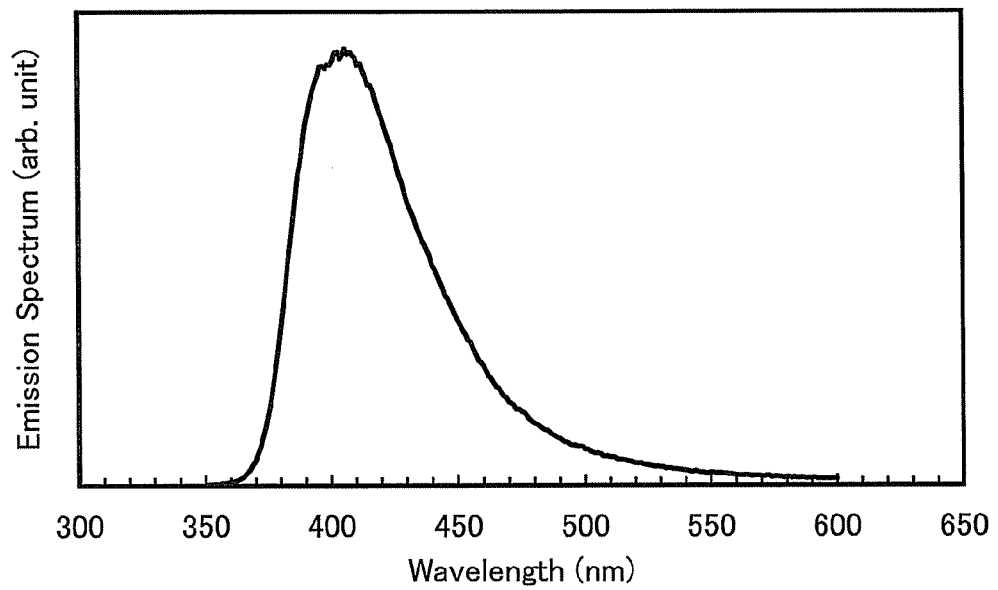

Further, FIG. 16A shows an absorption spectrum of a toluene solution of DBTBIm-III, and FIG. 16B shows an emission spectrum thereof. FIG. 17A shows an absorption spectrum of a thin film of DBTBIm-III, and FIG. 17B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 16A and 16B and FIGS. 17A and 17B, the horizontal axis represents wavelength (nm) and the vertical axis represents intensity (arbitrary unit). In the case of the toluene solution, absorption peaks were observed at around 284 nm, 301 nm, and 351 nm, and an emission wavelength peak was 381 nm (excitation wavelength: 307 nm). In the case of the thin film, absorption peaks were observed at around 265 nm, 306 nm, and 357 nm, and an emission wavelength peak was 407 nm (excitation wavelength: 335 nm).

Further, the glass transition temperature of DBTBIm-III was examined with a differential scanning calorimeter (DSC). The measurement results show that the glass transition temperature of DBTBIm-III is 136° C. Thus, DBTBIm-III has a high glass transition temperature and good heat resistance. In addition, a peak indicating crystallization was not observed; thus, it is found that DBTBIm-III is a substance which is difficult to crystallize.

Example 4

This example will give descriptions of a method of synthesizing 2-[4-(6-phenyldibenzothiophen-4-yl)phenyl]-1-phenyl-1H-benzimidazole (abbreviation: DBTBIm-IV) represented by the following Structural formula (188).

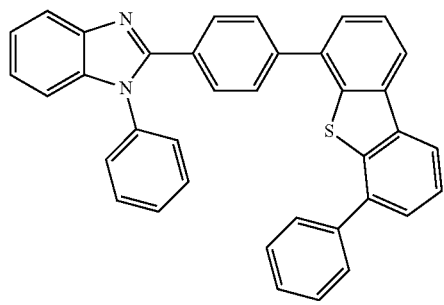

(188)

Synthesis of 2-[4-(6-phenyldibenzothiophen-4-yl)phenyl]-1-phenyl-1H-benzimidazole (abbreviation: DBTBIm-IV)

The synthesis scheme of 2-[4-(6-phenyldibenzothiophen-4-yl)phenyl]-1-phenyl-1H-benzimidazole (abbreviation: DBTBIm-IV) is illustrated in (B-4).

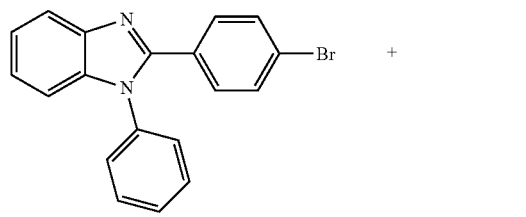

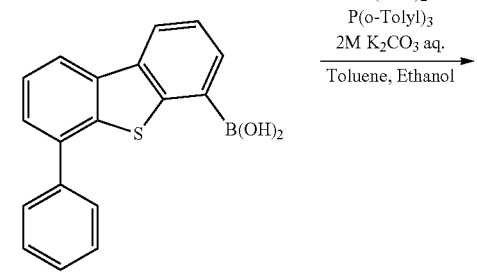

(B-4)

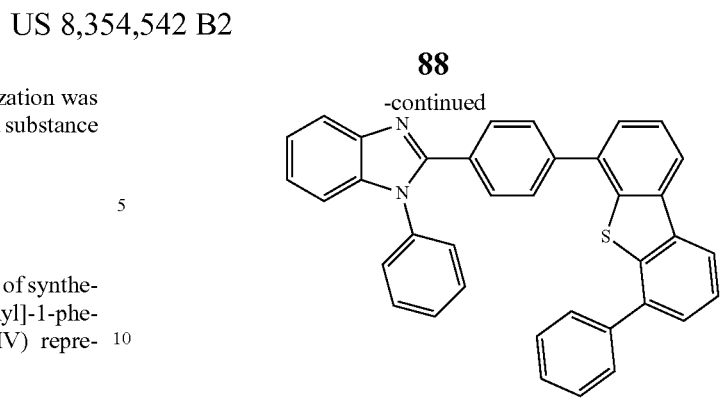

(188)

In a 100-mL three-neck flask, a mixture of 1.7 g (5.0 mmol) of 2-(4-bromophenyl)-1-phenyl-1H-benzimidazole, 1.5 g (5.0 mmol) of 6-phenyldibenzothiophen-4-boronic acid, 22 mg (0.1 mmol) of palladium(II) acetate, 60 mg (0.2 mmol) of tri(ortho-tolyl)phosphine, 20 mL of toluene, 2 mL of ethanol, and 7.5 mL of a 2 mol/L aqueous solution of potassium carbonate was stirred to be degassed under reduced pressure. Then, the mixture was heated and stirred at 90° C. for 2.5 hours under a nitrogen stream.

After a predetermined time, 150 mL of toluene was added to this mixture solution, and the organic layer of the resulting suspension was suction filtered through Celite (produced by Wako Pure Chemical Industries, Ltd., Catalog No. 531-16855). The resulting filtrate was concentrated, followed by purification using silica gel column chromatography. The silica gel column chromatography was carried out using a mixed solvent of toluene and ethyl acetate in a ratio of 19 to 1 as a developing solvent. The obtained fractions were concentrated, and acetone and methanol were added to the mixture, followed by irradiation with ultrasonic waves. The precipitated solid was collected by suction filtration. Thus, 2.2 g of a white powder was obtained in 83% yield, which was the substance to be produced.

The Rf values of the produced substance and 2-(4-bromophenyl)-1-phenyl-1H-benzimidazole were respectively 0.21 and 0.36, which were found by silica gel thin layer chromatography (TLC) (with a developing solvent containing ethyl acetate and hexane in a ratio of 1 to 5).

The nuclear magnetic resonance (NMR) measurement identified this compound as 2-[4-(6-phenyldibenzothiophen-4-yl)phenyl]-1-phenyl-1H-benzimidazole (abbreviation: DBTBIm-IV).

$^1$H NMR data of the obtained compound are as follows: $^1$H NMR (CDCl$_3$, 300 MHz): δ (ppm)=7.26-7.59 (m, 15H), 7.64-7.71 (m, 6H), 7.90-7.93 (d, J=7.8 Hz, 1H), 8.15-8.19 (m, 2H).

Figure 18A:
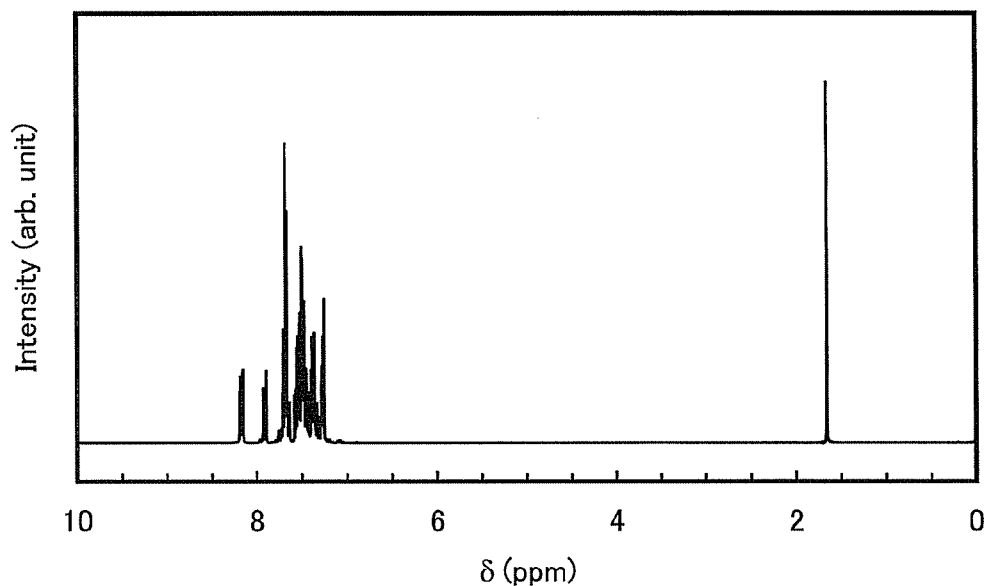
FIGS. 18A and 18B illustrate $^1$H NMR charts of 2-[4-(6-phenyldibenzothiophen-4-yl)phenyl]-1-phenyl-1H-benzimidazole.
Figure 18B:
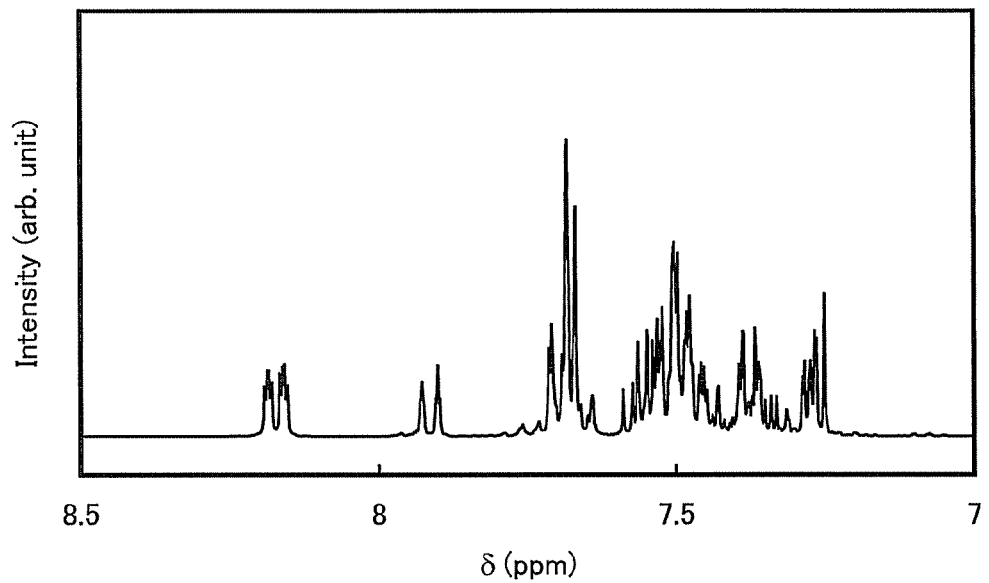

FIGS. 18A and 18B illustrate the $^1$H NMR charts. Note that FIG. 18B is a chart showing an enlarged part of FIG. 18A in the range of 7.0 ppm to 8.5 ppm.

Figure 19A:
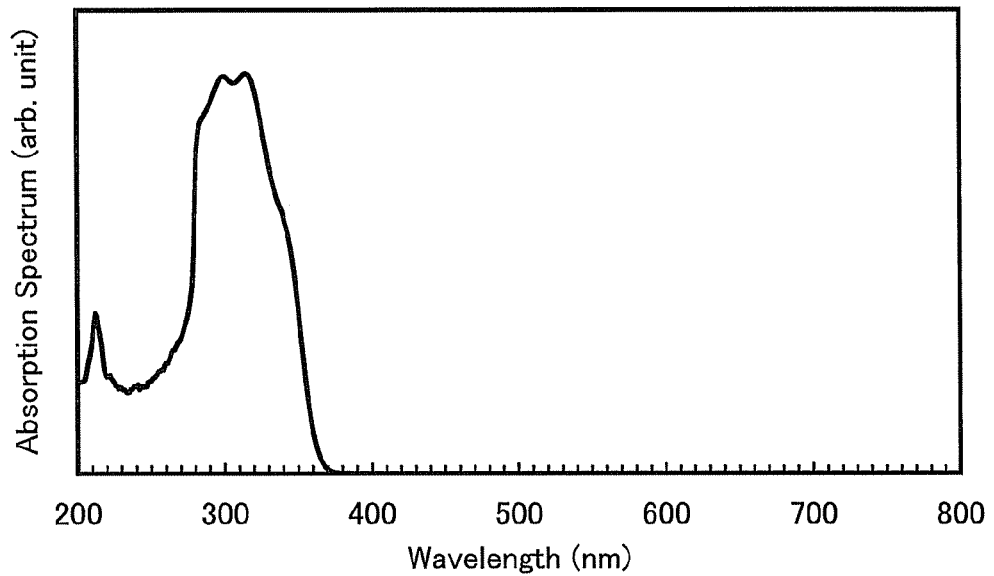
FIGS. 19A and 19B illustrate respectively an absorption spectrum and an emission spectrum of a toluene solution of 2-[4-(6-phenyldibenzothiophen-4-yl)phenyl]-1-phenyl-1H-benzimidazole.
Figure 19B:
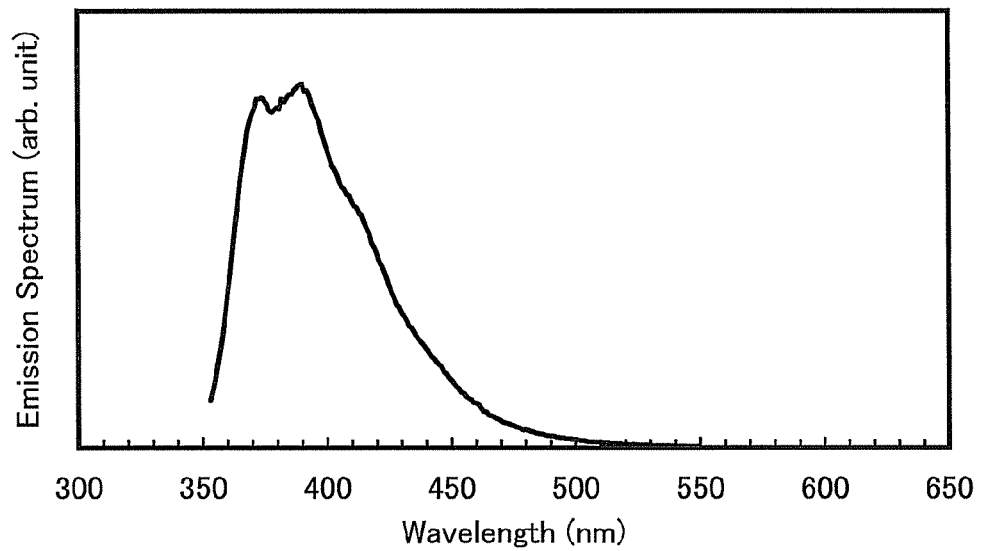
Figure 20A:
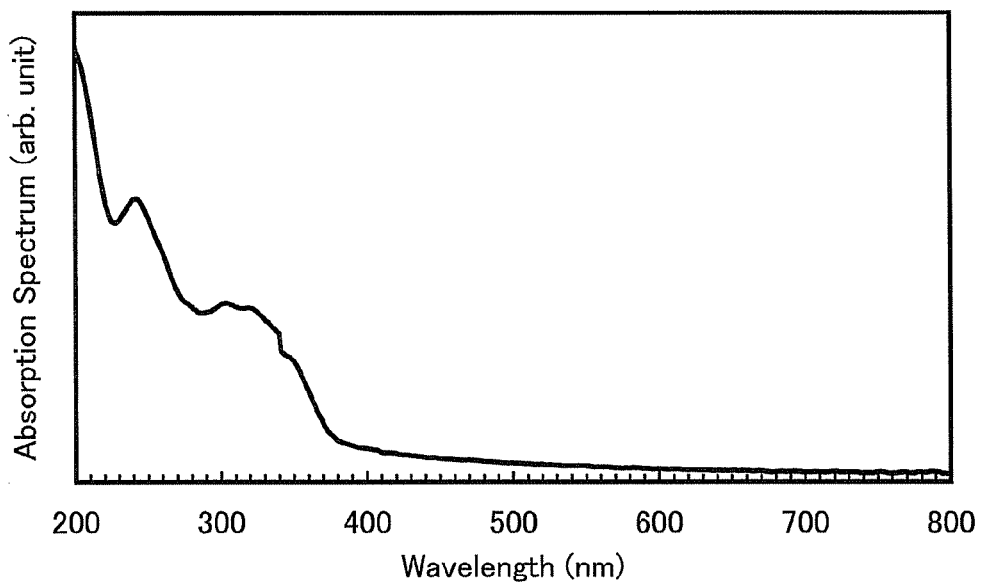
FIGS. 20A and 20B illustrate respectively an absorption spectrum and an emission spectrum of a thin film of 2-[4-(6-phenyldibenzothiophen-4-yl)phenyl]-1-phenyl-1H-benzimidazole.
Figure 20B:
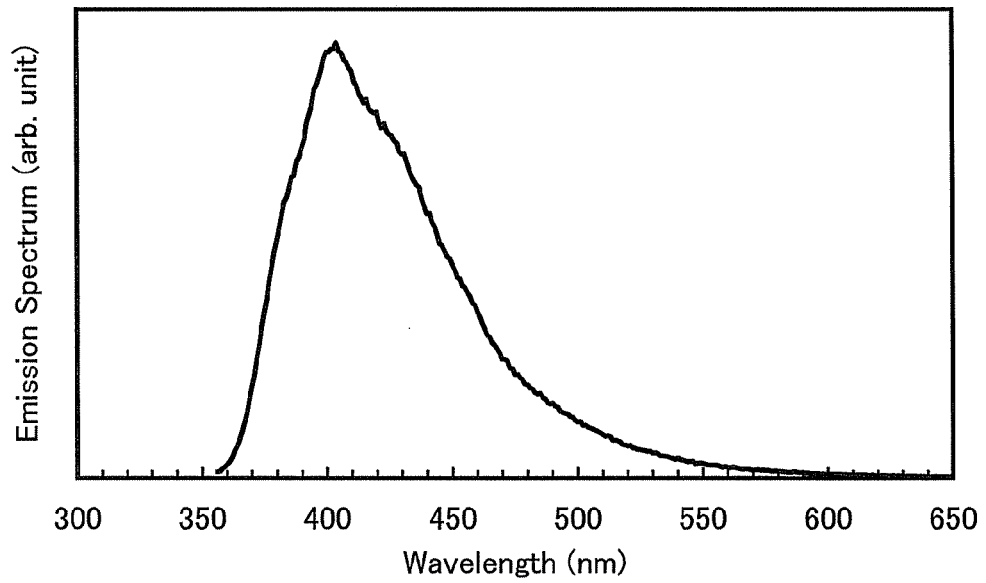

Further, FIG. 19A shows an absorption spectrum of a toluene solution of DBTBIm-IV, and FIG. 19B shows an emission spectrum thereof. FIG. 20A shows an absorption spectrum of a thin film of DBTBIm-IV, and FIG. 20B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 19A and 19B and FIGS. 20A and 20B, the horizontal axis represents wavelength (nm) and the vertical axis represents intensity (arbitrary unit). In the case of the toluene solution, an absorption peak was observed at around 316 nm and emission wavelength peaks were 371 nm and 387 nm (excitation wavelength: 320 nm). In the case of the thin film, absorption peaks were observed at around 242 nm, 304 nm, and 319 nm, and an emission wavelength peak was 402 nm (excitation wavelength: 349 nm).

Example 5

This example will give descriptions of a method of synthesizing 2-[4-(dibenzofuran-4-yl)phenyl]-1-phenyl-1H-benzimidazole (abbreviation: DBFBIm-II) represented by the following Structural formula (130).

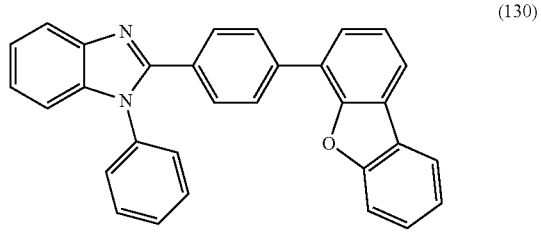 [SMILES: c1ccc(-n2c(-c3ccc(-c4cccc5c4oc4ccccc45)cc3)nc3ccccc32)cc1]

(130)

Synthesis of 2-[4-(dibenzofuran-4-yl)phenyl]-1-phenyl-1H-benzimidazole (abbreviation: DBFBIm-II)

The synthesis scheme of 2-[4-(dibenzofuran-4-yl)phenyl]-1-phenyl-1H-benzimidazole (abbreviation: DBFBIm-II) is illustrated in (B-5).

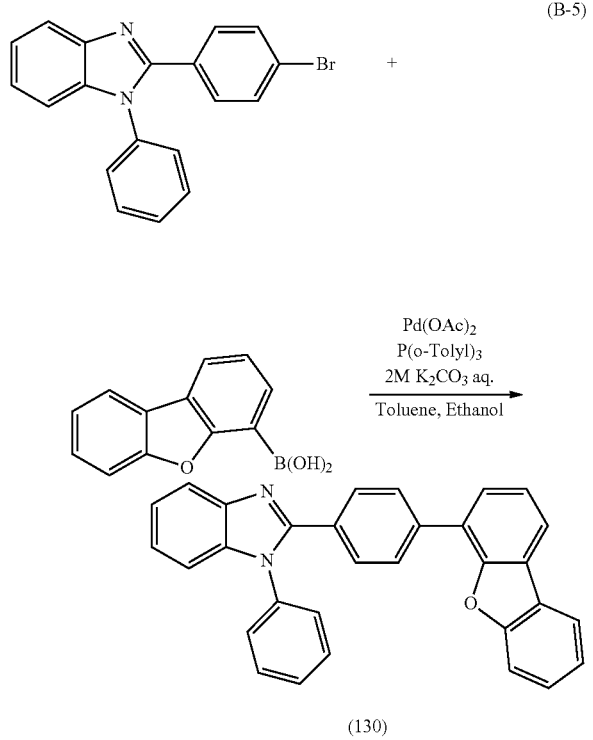

In a 100-mL three-neck flask, a mixture of 1.7 g (5.0 mmol) of 2-(4-bromophenyl)-1-phenyl-1H-benzimidazole, 1.0 g (5.0 mmol) of dibenzofuran-4-boronic acid, 22 mg (0.1 mmol) of palladium(II) acetate, 60 mg (0.2 mmol) of tri (ortho-tolyl)phosphine, 30 mL of toluene, 3 mL of ethanol, and 7.5 mL of a 2 mol/L aqueous solution of potassium carbonate was stirred to be degassed under reduced pressure. Then, the mixture was heated and stirred at 90° C. for 4.5 hours under a nitrogen stream.

After a predetermined time, 50 mL of toluene was added to this mixture solution, and the organic layer of the resulting suspension was suction filtered through Celite (produced by Wako Pure Chemical Industries, Ltd., Catalog No. 531-16855). The resulting filtrate was concentrated, followed by purification using silica gel column chromatography. The chromatography was carried out using a mixed solvent of toluene and ethyl acetate in a ratio of 19 to 1 as a developing solvent. The obtained fractions were concentrated, and hexane was added to the mixture, followed by irradiation with ultrasonic waves. The precipitated solid was collected by suction filtration. Thus, 2.0 g of a white powder was obtained in 92% yield, which was the substance to be produced.

The Rf values of the produced substance and 2-(4-bromophenyl)-1-phenyl-1H-benzimidazole were respectively 0.10 and 0.22, which were found by silica gel thin layer chromatography (TLC) (with a developing solvent containing ethyl acetate to hexane in a ratio of 1 to 10).

A nuclear magnetic resonance (NMR) method identified this compound as 2-[4-(dibenzofuran-4-yl)phenyl]-1-phenyl-1H-benzimidazole (abbreviation: DBFBIm-II), which was the substance to be produced.

$^1$H NMR data of the obtained substance are as follows: $^1$H NMR (CDCl$_3$, 300 MHz): δ (ppm)=7.27-7.63 (m, 13H), 7.74-7.78 (m, 2H), 7.89-8.00 (m, 5H).

Figure 21A:
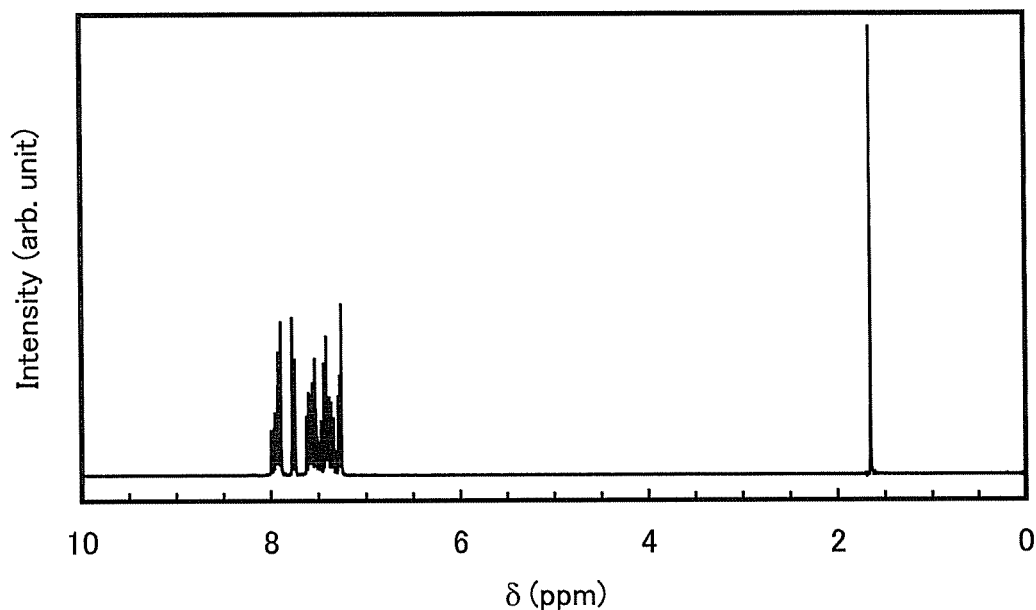
FIGS. 21A and 21B illustrate $^1$H NMR charts of 2-[4-(dibenzofuran-4-yl)phenyl]-1-phenyl-1H-benzimidazole.
Figure 21B:
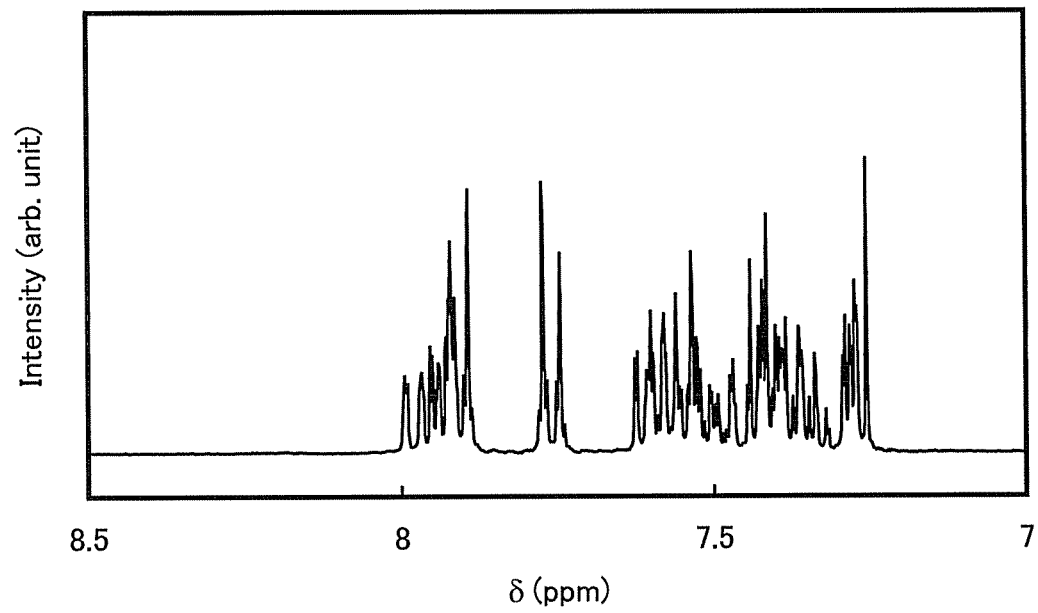

FIGS. 21A and 21B illustrate the $^1$H NMR charts. Note that FIG. 21B is a chart showing an enlarged part of FIG. 21A in the range of 7.0 ppm to 8.5 ppm.

Figure 22A:
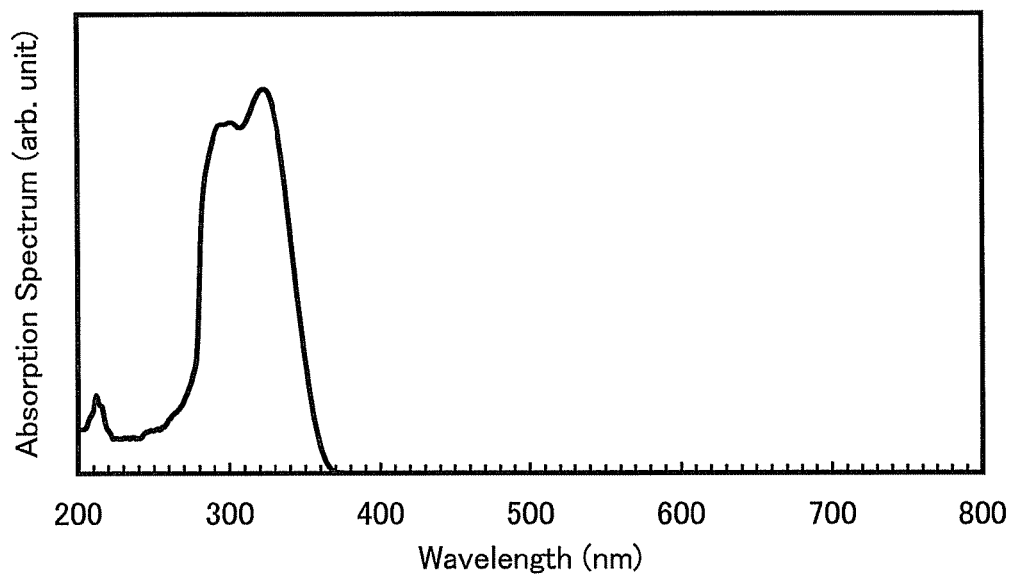
FIGS. 22A and 22B illustrate respectively an absorption spectrum and an emission spectrum of a toluene solution of 2-[4-(dibenzofuran-4-yl)phenyl]-1-phenyl-1H-benzimidazole.
Figure 22B:
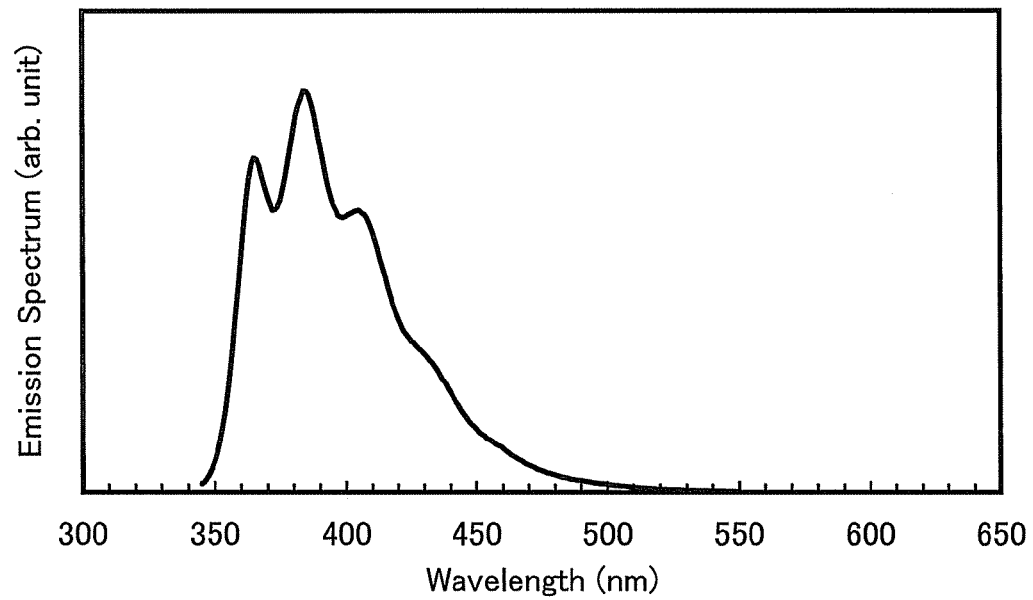
Figure 23A:
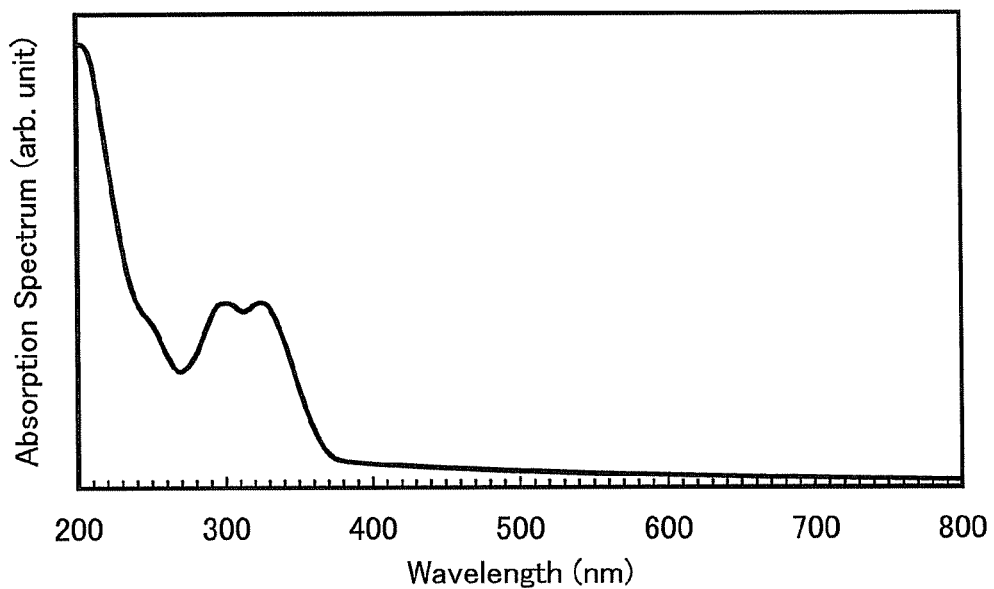
FIGS. 23A and 23B illustrate respectively an absorption spectrum and an emission spectrum of a thin film of 2-[4-(dibenzofuran-4-yl)phenyl]-1-phenyl-1H-benzimidazole.
Figure 23B:
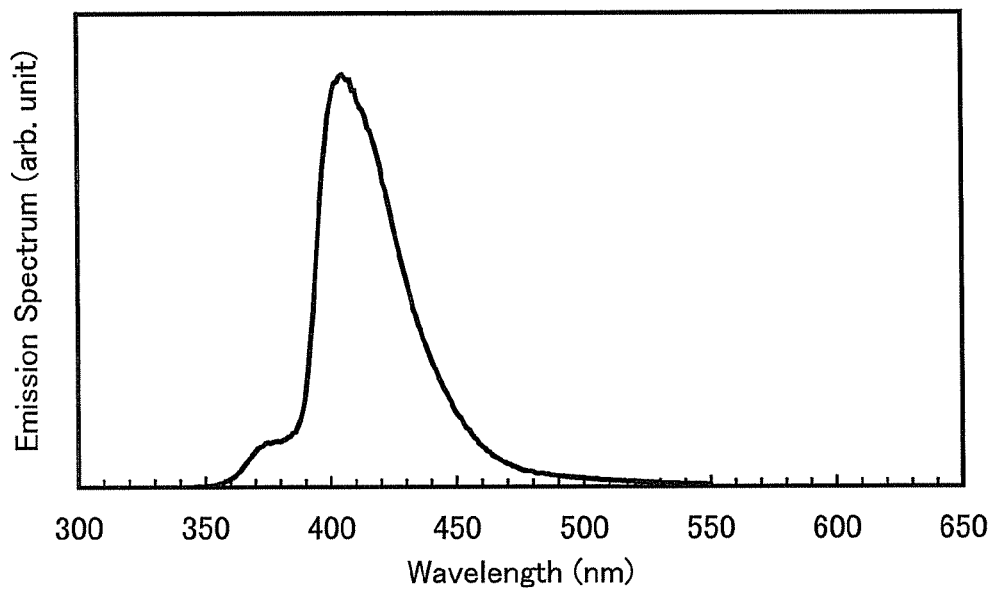

Further, FIG. 22A shows an absorption spectrum of a toluene solution of DBFBIm-II, and FIG. 22B shows an emission spectrum thereof. FIG. 23A shows an absorption spectrum of a thin film of DBFBIm-II, and FIG. 23B shows an emission spectrum thereof. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. In FIGS. 22A and 22B and FIGS. 23A and 23B, the horizontal axis represents wavelength (nm) and the vertical axis represents intensity (arbitrary unit). In the case of the toluene solution, an absorption peak was observed at around 323 nm, and emission wavelength peaks were 365 nm, 385 nm and 405 nm (excitation wavelength: 329 nm). In the case of the thin film, absorption peaks were observed at around 300 nm and 324 nm, and an emission wavelength peak was 405 nm (excitation wavelength: 330 nm).

Example 6

Figure 41:
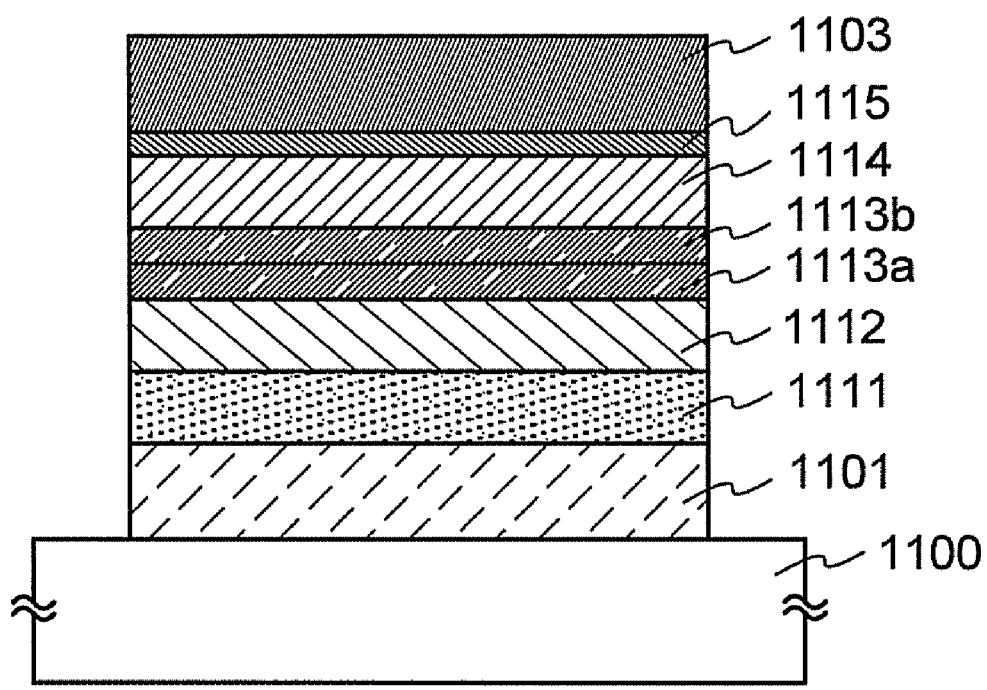
FIG. 41 illustrates a light-emitting element of Examples.

In this example, a light-emitting element of one embodiment of the present invention will be described referring to FIG. 41. The chemical formulae of materials used in this example are illustrated below.

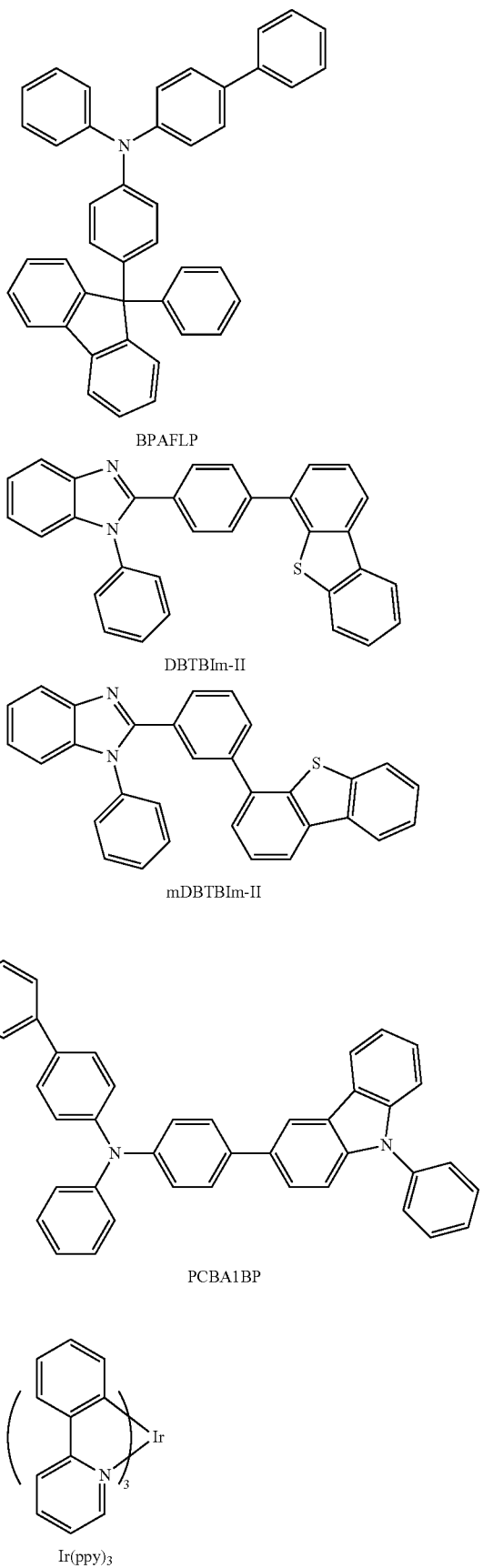

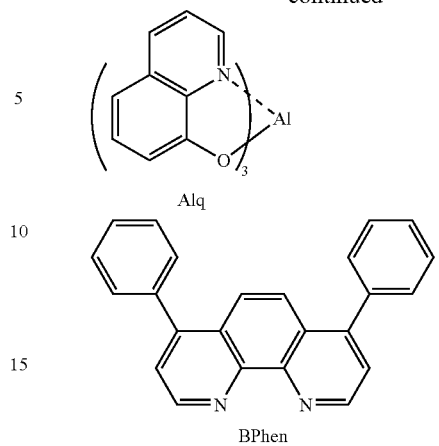

Methods of fabricating Light-emitting Element 1 and Light-emitting Element 2 of this example will now be described.

(Light-Emitting Element 1)

First, indium tin oxide containing silicon oxide (ITSO) was deposited by a sputtering method on a glass substrate 1100, whereby a first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^4$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, 4-phenyl-4'-(9-phenylfluoren-9-yl)triphenylamine (abbreviation: BPAFLP) and molybdenum(VI) oxide were co-evaporated to form a hole-injection layer (HIL) 1111 over the first electrode 1101. The thickness of the hole-injection layer 1111 was 50 nm, and the weight ratio of BPAFLP to molybdenum(VI) oxide was controlled to be 4:2 (=BPAFLP:molybdenum(VI) oxide). Note that the co-evaporation method refers to an evaporation method in which evaporation is carried out from a plurality of evaporation sources at the same time in one treatment chamber.

Next, BPAFLP was deposited to a thickness of 10 nm over the hole-injection layer 1111, whereby a hole-transport layer (HTL) 1112 was formed.

Further, 2-[4-(dibenzothiophen-4-yl)phenyl]-1-phenyl-1H-benzimidazole (abbreviation: DBTBIm-II) synthesized in Example 1, 4-phenyl-4'-(9-phenyl-9H-carbazol-3-yl)triphenylamine (abbreviation: PCBA1BP), and tris(2-phenylpyridinato-N,C$^{2'}$)iridium (abbreviation: Ir(ppy)$_3$) were co-evaporated, whereby a first light-emitting layer 1113a was formed over the hole-transport layer 1112. The weight ratio of DBTBIm-II to PCBA1BP and Ir(ppy)$_3$ was adjusted to 1:0.2:

0.08 (=DBTBIm-II:PCBA1BP:Ir(ppy)$_3$). The thickness of the first light-emitting layer 1113a was set to 20 nm.

Furthermore, DBTBIm-II and Ir(ppy)$_3$ were co-evaporated, whereby a second light-emitting layer (EmL) 1113b was formed over the first light-emitting layer 1113a. The weight ratio of DBTBIm-II to Ir(ppy)$_3$ was adjusted to 1:0.08 (=DBTBIm-II:Ir(ppy)$_3$). The thickness of the second light-emitting layer (EmL) 1113b was set to 20 nm.

Then, over the second light-emitting layer 1113b, a 15-nm-thick layer of tris(8-quinolinolato)aluminum (abbreviation: Alq) and, a 15-nm-thick layer of bathophenanthroline (abbreviation: BPhen) were deposited on the Alq layer, whereby an electron-transport layer (ETL) 1114 including Alq and BPhen was formed.

Further, a 1-nm-thick film of lithium fluoride (LiF) was formed over the electron-transport layer 1114 by evaporation, whereby an electron-injection layer (EIL) 1115 was formed.

Lastly, a 200-nm-thick film of aluminum was formed by evaporation to form a second electrode 1103 functioning as a cathode. Thus, Light-emitting Element 1 of this example was fabricated.

Note that, in the above evaporation process, evaporation was all performed by a resistance heating method.
(Light-Emitting Element 2)

The first light-emitting layer 1113a of Light-emitting Element 2 was formed by co-evaporation of 2-[3-(dibenzothiophen-4-yl)phenyl]-1-phenyl-1H-benzimidazole (abbreviation: mDBTBIm-II) synthesized in Example 2, PCBA1BP, and Ir(ppy)$_3$, instead of the materials used for Light-emitting Element 1. The weight ratio of mDBTBIm-II to PCBA1BP and Ir(ppy)$_3$ was adjusted to 1:0.2:0.08 (=mDBTBIm-II:PCBA1BP:Ir(ppy)$_3$). The thickness of the first light-emitting layer 1113a was set to 20 nm.

Further, the second light-emitting layer 1113b of Light-emitting Element 2 was formed by co-evaporation of mDBTBIm-II and Ir(ppy)$_3$, instead of the materials used for Light-emitting Element 1. The weight ratio of mDBTBIm-II to Ir(ppy)$_3$ was adjusted to 1:0.08 (=mDBTBIm-II:Ir(ppy)$_3$). The thickness of the second light-emitting layer 1113b was set to 20 nm. The structure other than the first light-emitting layer 1113a and the second light-emitting layer 1113b was formed in the same manner as that of Light-emitting Element 1.

Figure 26:
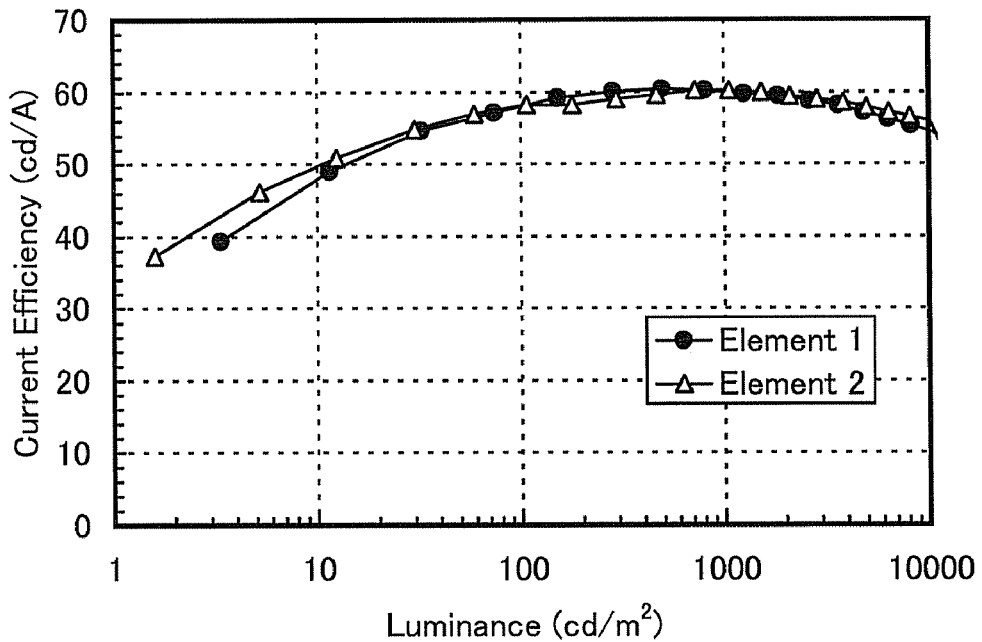
FIG. 26 illustrates luminance vs. current efficiency characteristics of Light-emitting Elements 1 and 2.
Figure 27:
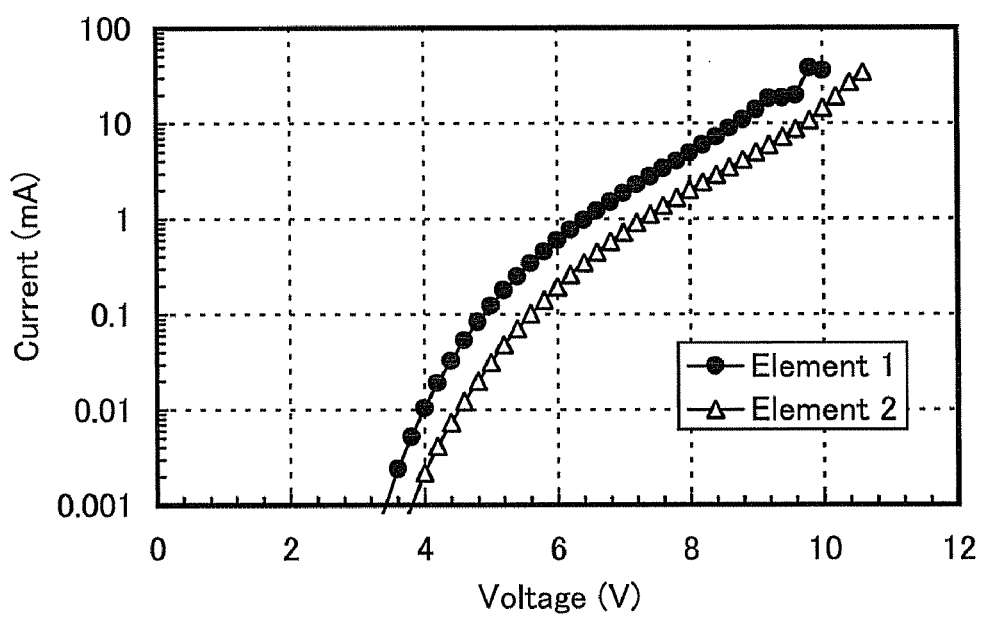
FIG. 27 illustrates voltage vs. current characteristics of Light-emitting Elements 1 and 2.

Table 1 shows element structures of Light-emitting Elements 1 and 2 formed as described above.

zontal axis represents applied voltage (V) and the vertical axis represents luminance (cd/m$^2$). FIG. 26 shows the luminance vs. current efficiency characteristics. In FIG. 26, the horizontal axis represents luminance (cd/m$^2$) and the vertical axis represents current efficiency (cd/A). FIG. 27 shows the voltage vs. current characteristics. In FIG. 27, the horizontal axis represents voltage (V) and the vertical axis represents current (mA).

The CIE chromaticity coordinates of Light-emitting Element 1 at a luminance of 806 cd/m$^2$ were as follows: (x, y)=(0.33, 0.61), and those of Light-emitting Element 2 at a luminance of 1060 cd/m$^2$ were as follows: (x, y)=(0.33, 0.62). Thus, Light-emitting Elements 1 and 2 are found to emit light from Ir(ppy)$_3$.

FIG. 26 demonstrates that both Light-emitting Elements 1 and 2, which were fabricated, have high current efficiency.

Figure 25:
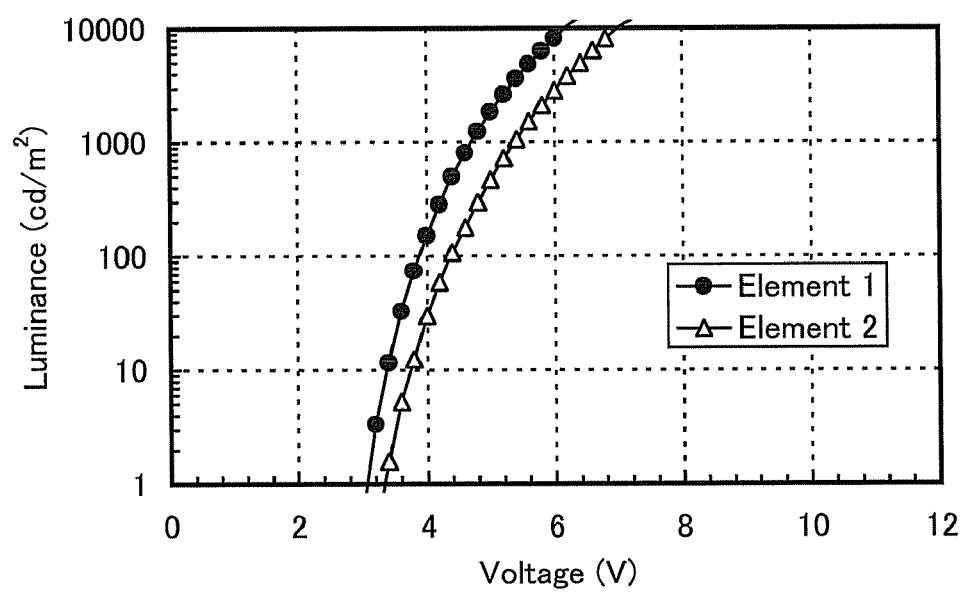
FIG. 25 illustrates voltage vs. luminance characteristics of Light-emitting Elements 1 and 2.

As seen from FIG. 25 and FIG. 27, Light-emitting Element 1 shows higher luminance than Light-emitting Element 2 at the same voltage. This is because Light-emitting Element 1 can obtain a larger amount of current than Light-emitting Element 2 at the same voltage.

A structural difference between the heterocyclic compounds of embodiments of the present invention used for Light-emitting Elements 1 and 2, in each of which the heterocyclic compound is used as the host material of the light-emitting layer, is that the 2-position of the benzimidazole skeleton and the 4-position of the dibenzothiophene skeleton which are included in the heterocyclic compound of one embodiment of the present invention are bonded through a meta-phenylene group in Light-emitting Element 2 while they are bonded through a para-phenylene group in Light-emitting Element 1. Whether the 2-position of the benzimidazole skeleton and the 4-position of the dibenzothiophene skeleton are bonded through the meta-phenylene group or the para-phenylene group makes a difference in voltage vs. luminance characteristics between Light-emitting Elements 1 and 2. This reveals that, by having the 2-position of the benzimidazole skeleton and the 4-position of the dibenzothiophene skeleton which are bonded through the para-phenylene group, the heterocyclic compound of one embodiment of the present invention is effective in enhancing voltage vs. luminance characteristics.

As described above, by using DBTBIm-II produced in Example 1 and mDBTBIm-II produced in Example 2 as the

TABLE 1

| | 1st electrode | HIL | HTL | 1st EmL | 2nd EmL | | ETL | EIL | 2nd electrode |
|---|---|---|---|---|---|---|---|---|---|
| Light-emitting Element 1 | ITSO 110 nm | BPAFLP:MoOx (=4:2) 50 nm | BPAFLP 10 nm | DBTBIm-II:PCBA1BP:Ir(ppy)$_3$ (=1:0.2:0.08) 20 nm | DBTBIm-II:Ir(ppy)$_3$ (=1:0.08) 20 nm | Alq 15 nm | BPhen 15 nm | LiF 1 nm | Al 200 nm |
| Light-emitting Element 2 | ITSO 110 nm | BPAFLP:MoOx (=4:2) 50 nm | BPAFLP 10 nm | mDBTBIm-II:PCBA1BP:Ir(ppy)$_3$ (=1:0.2:0.08) 20 nm | mDBTBIm-II:Ir(ppy)$_3$ (=1:0.08) 20 nm | Alq 15 nm | BPhen 15 nm | LiF 1 nm | Al 200 nm |

Light-emitting Elements 1 and 2 were sealed in a glove box containing a nitrogen atmosphere so as not to be exposed to air. Then, operation characteristics of these elements were measured. Note that the measurement was carried out at room temperature (in the atmosphere kept at 25° C.).

Figure 24:
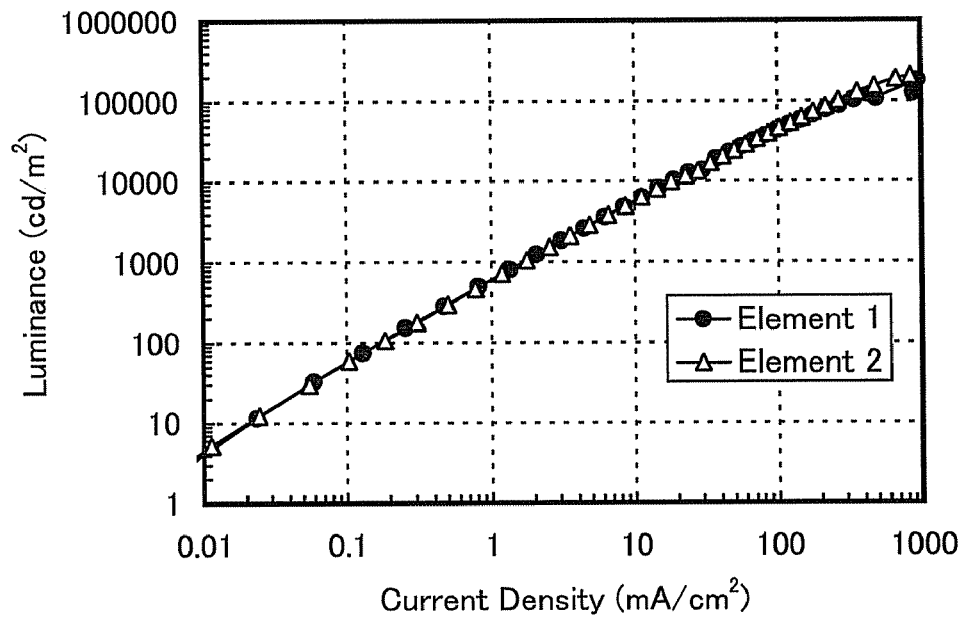
FIG. 24 illustrates current density vs. luminance characteristics of Light-emitting Elements 1 and 2.

FIG. 24 shows the current density vs. luminance characteristics of Light-emitting Elements 1 and 2. In FIG. 24, the horizontal axis represents current density (mA/cm$^2$) and the vertical axis represents luminance (cd/m$^2$). FIG. 25 shows the voltage vs. luminance characteristics. In FIG. 25, the horihost materials of the light-emitting layers, the light-emitting elements were each able to have high current efficiency.

Example 7

In this example, a light-emitting element of one embodiment of the present invention will be described referring to FIG. 41.

Methods of fabricating Light-emitting Element 3 and Light-emitting Element 4 of this example will now be described. Materials used in the present example are the same as those used in Example 6, and their chemical formulae are omitted here.

(Light-Emitting Element 3)

The structure other than the electron-transport layer 1114 was formed in the same manner as that of Light-emitting Element 1 described in Example 6. Specifically, a 15-nm-thick layer of 2-[4-(dibenzothiophen-4-yl)phenyl]-1-phenyl-1H-benzimidazole (abbreviation: DBTBIm-II) synthesized in Example 1 and, a 15-nm-thick layer of BPhen were deposited on the DBTBIm-II layer, whereby the electron-transport layer 1114 including DBTBIm-II and BPhen was formed.

(Light-Emitting Element 4)

The structure other than the electron-transport layer 1114 was formed in the same manner as that of Light-emitting Element 2 described in Example 6. Specifically, a 15-nm-thick layer of 2-[3-(dibenzothiophen-4-yl)phenyl]-1-phenyl-1H-benzimidazole (abbreviation: mDBTBIm-II) synthesized in Example 2 and, a 15-nm-thick layer of BPhen were deposited on the mDBTBIm-II layer, whereby the electron-transport layer 1114 including mDBTBIm-II and BPhen was formed.

Table 2 shows element structures of Light-emitting Elements 3 and 4 formed as described above.

Light-emitting Elements 3 and 4, in each of which the heterocyclic compound is used as the host material of the light-emitting layer and as the material of the electron-transport layer, is that the 2-position of the benzimidazole skeleton and the 4-position of the dibenzothiophene skeleton which are included in the heterocyclic compound of one embodiment of the present invention are bonded through a meta-phenylene group in Light-emitting Element 4 while they are bonded through a para-phenylene group in Light-emitting Element 3. Whether the 2-position of the benzimidazole skeleton and the 4-position of the dibenzothiophene skeleton are bonded through the meta-phenylene group or the para-phenylene group makes a difference in voltage vs. luminance characteristics between Light-emitting Elements 3 and 4. This reveals that, by having the 2-position of the benzimidazole skeleton and the 4-position of the dibenzothiophene skeleton which are bonded through the para-phenylene group, the heterocyclic compound of one embodiment of the present invention is effective in enhancing voltage vs. luminance characteristics.

As described above, by using DBTBIm-II produced in Example 1 and mDBTBIm-II produced in Example 2 as the host materials of the light-emitting layers and also as the materials of the electron-transport layers, the light-emitting elements were each able to have high current efficiency.

TABLE 2

| | 1st electrode | HIL | HTL | 1st EmL | 2nd EmL | ETL | EIL | 2nd electrode |
|---|---|---|---|---|---|---|---|---|
| Light-emitting Element 3 | ITSO 110 nm | BPAFLP:MoOx (=4:2) 50 nm | BPAFLP 10 nm | DBTBIm-II:PCBA1BP:Ir(ppy)$_3$ (=1:0.2:0.08) 20 nm | DBTBIm-II:Ir(ppy)$_3$ (=1:0.08) 20 nm | DBTBIm-II 15 nm | BPhen 15 nm | LiF 1 nm | Al 200 nm |
| Light-emitting Element 4 | ITSO 110 nm | BPAFLP:MoOx (=4:2) 50 nm | BPAFLP 10 nm | mDBTBIm-II:PCBA1BP:Ir(ppy)$_3$ (=1:0.2:0.08) 20 nm | mDBTBIm-II:Ir(ppy)$_3$ (=1:0.08) 20 nm | mDBTBIm-II 15 nm | BPhen 15 nm | LiF 1 nm | Al 200 nm |

Light-emitting Elements 3 and 4 were sealed in a glove box containing a nitrogen atmosphere so as not to be exposed to air. Then, operation characteristics of these elements were measured. Note that the measurement was carried out at room temperature (in the atmosphere kept at 25° C.).

Figure 28:
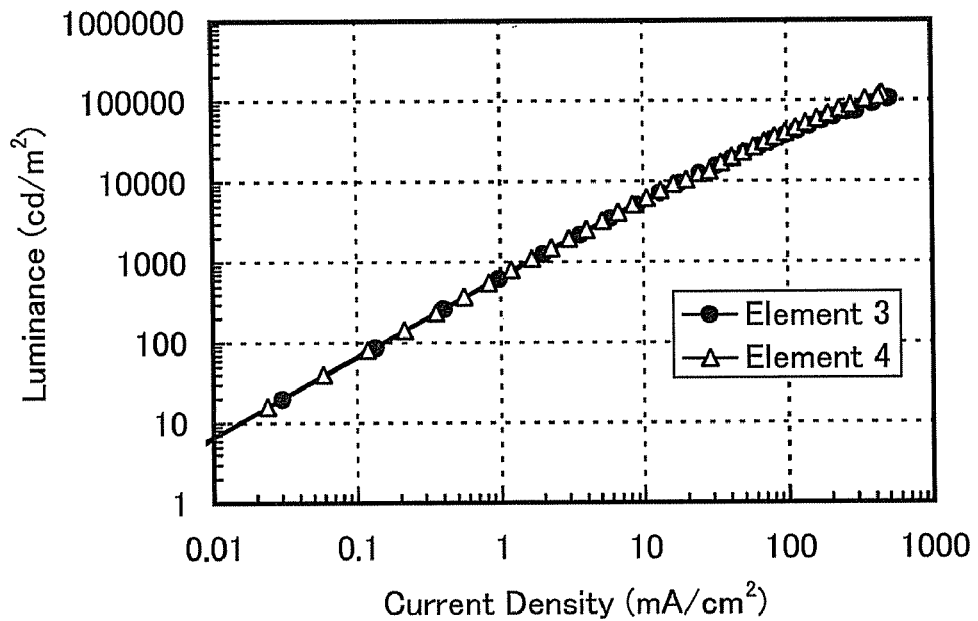
FIG. 28 illustrates current density vs. luminance characteristics of Light-emitting Elements 3 and 4.
Figure 29:
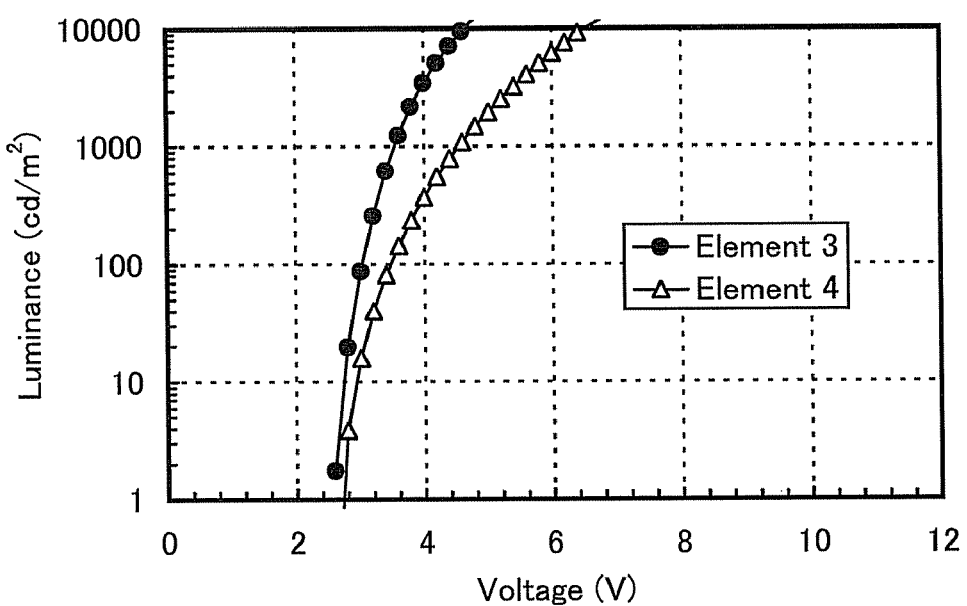
FIG. 29 illustrates voltage vs. luminance characteristics of Light-emitting Elements 3 and 4.
Figure 30:
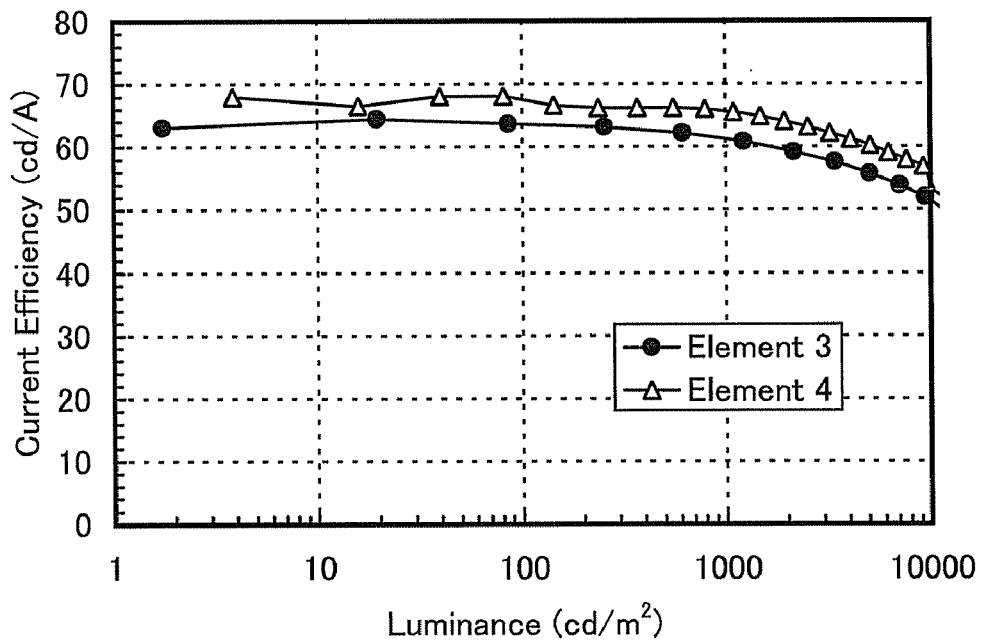
FIG. 30 illustrates luminance vs. current efficiency characteristics of Light-emitting Elements 3 and 4.
Figure 31:
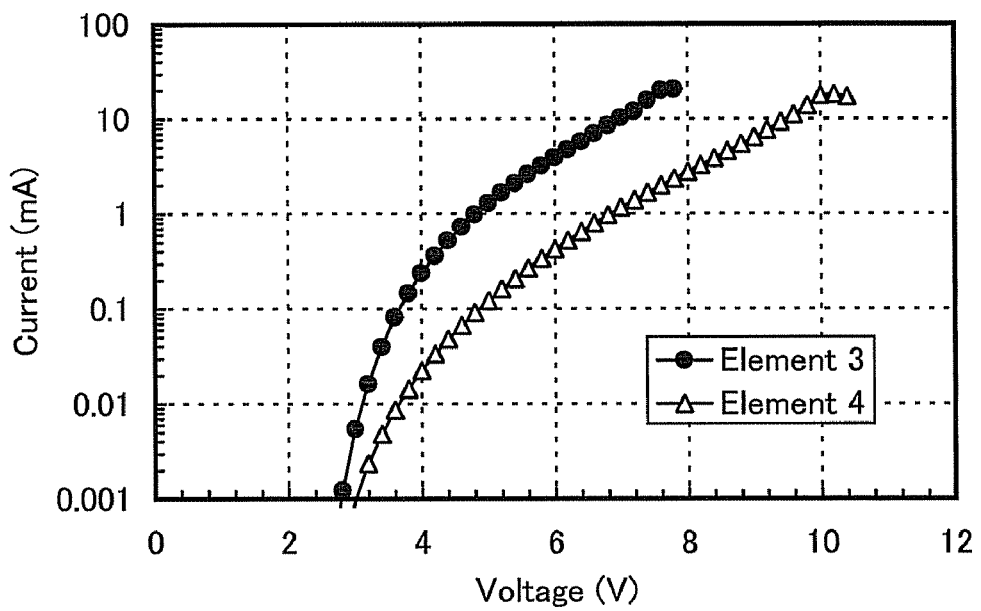
FIG. 31 illustrates voltage vs. current characteristics of Light-emitting Elements 3 and 4.

FIG. 28 shows the current density vs. luminance characteristics of Light-emitting Elements 3 and 4. In FIG. 28, the horizontal axis represents current density (mA/cm$^2$) and the vertical axis represents luminance (cd/m$^2$). FIG. 29 shows the voltage vs. luminance characteristics. In FIG. 29, the horizontal axis represents applied voltage (V) and the vertical axis represents luminance (cd/m$^2$). FIG. 30 shows the luminance vs. current efficiency characteristics. In FIG. 30, the horizontal axis represents luminance (cd/m$^2$) and the vertical axis represents current efficiency (cd/A). FIG. 31 shows the voltage vs. current characteristics. In FIG. 31, the horizontal axis represents voltage (V) and the vertical axis represents current (mA).

The CIE chromaticity coordinates of Light-emitting Element 3 at a luminance of 1227 cd/m$^2$ were as follows: (x, y)=(0.34, 0.61), and those of Light-emitting Element 4 at a luminance of 1095 cd/m$^2$ were as follows: (x, y)=(0.33, 0.61). Thus, Light-emitting Elements 3 and 4 are found to emit light from Ir(ppy)$_3$.

FIG. 30 demonstrates that both Light-emitting Elements 3 and 4, which were fabricated, have high current efficiency.

As seen from FIG. 29 and FIG. 31, Light-emitting Element 3 shows higher luminance than Light-emitting Element 4 at the same voltage. This is because Light-emitting Element 3 can obtain a larger amount of current than Light-emitting Element 4.

A structural difference between the heterocyclic compounds of embodiments of the present invention used for Example 8

In this example, a light-emitting element of one embodiment of the present invention will be described referring to FIG. 41. The chemical formulae of materials used in this example are illustrated below. Note that the materials the chemical formulae of which are described above will be omitted.

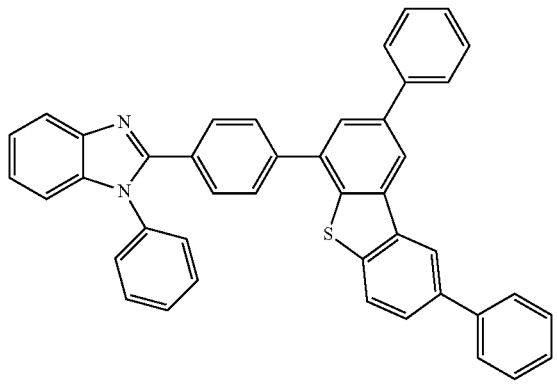

DBTBIm-III (Light-Emitting Element 5)

First, ITSO was deposited by a sputtering method on the glass substrate 1100, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, BPAFLP and molybdenum(VI) oxide were co-evaporated to form the hole-injection layer 1111 over the first electrode 1101. The thickness of the hole-injection layer 1111 was 50 nm, and the weight ratio of BPAFLP to molybdenum(VI) oxide was controlled to be 4:2 (=BPAFLP:molybdenum(VI) oxide). Note that the co-evaporation method refers to an evaporation method in which evaporation is carried out from a plurality of evaporation sources at the same time in one treatment chamber.

Next, BPAFLP was deposited to a thickness of 10 nm over the hole-injection layer 1111, whereby the hole-transport layer 1112 was formed.

(Light-Emitting Element 6)
First, the first electrode 1101, the hole-injection layer 1111, and the hole-transport layer 1112 were formed over the glass substrate 1100 in the same manner as those of Light-emitting Element 5.

Next, 2-[4-(dibenzothiophen-4-yl)phenyl]-1-phenyl-1H-benzimidazole (abbreviation: DBTBIm-II) synthesized in Example 1, PCBA1BP, and Ir(ppy)$_3$ were co-evaporated, whereby the first light-emitting layer 1113a was formed over the hole-transport layer 1112. The weight ratio of DBTBIm-II to PCBA1BP and Ir(ppy)$_3$ was adjusted to 1:0.25:0.08 (=DBTBIm-II:PCBA1BP:Ir(ppy)$_3$). The thickness of the first light-emitting layer 1113a was set to 20 nm.

Furthermore, DBTBIm-II and Ir(ppy)$_3$ were co-evaporated, whereby the second light-emitting layer 1113b was formed over the first light-emitting layer 1113a. The weight ratio of DBTBIm-II to Ir(ppy)$_3$ was adjusted to 1:0.08 (=DBTBIm-II:Ir(ppy)$_3$). The thickness of the second light-emitting layer 1113b was set to 20 nm.

Then, over the second light-emitting layer 1113b, a 15-nm-thick layer of DBTBIm-II and, a 15-nm-thick layer of BPhen were deposited on the DBTBIm-II layer, whereby the electron-transport layer 1114 including DBTBIm-II and BPhen was formed.

The electron-injection layer 1115 and the second electrode 1103 were formed over the electron-transport layer 1114 in the same manner as those of Light-emitting Element 5.

Table 3 shows element structures of Light-emitting Elements 5 and 6 formed as described above.

TABLE 3

| | 1st electrode | HIL | HTL | 1st EmL | 2nd EmL | ETL | EIL | 2nd electrode |
|---|---|---|---|---|---|---|---|---|
| Light-emitting Element 5 | ITSO 110 nm | BPAFLP:MoOx (=4:2) 50 nm | BPAFLP 10 nm | DBTBIm-III:PCBA1BP:Ir(ppy)$_3$ (=1:0.25:0.08) 20 nm | DBTBIm-III:Ir(ppy)$_3$ (=1:0.08) 20 nm | DBTBIm-III 15 nm | BPhen 15 nm | LiF 1 nm | Al 200 nm |
| Light-emitting Element 6 | ITSO 110 nm | BPAFLP:MoOx (=4:2) 50 nm | BPAFLP 10 nm | DBTBIm-II:PCBA1BP:Ir(ppy)$_3$ (=1:0.25:0.08) 20 nm | DBTBIm-II:Ir(ppy)$_3$ (=1:0.08) 20 nm | DBTBIm-II 15 nm | BPhen 15 nm | LiF 1 nm | Al 200 nm |

Further, 2-[4-(2,8-diphenyldibenzothiophen-4-yl)phenyl]-1-phenyl-1H-benzimidazole (abbreviation: DBTBIm-III) synthesized in Example 3, PCBA1BP, and Ir(ppy)$_3$ were co-evaporated, whereby the first light-emitting layer 1113a was formed over the hole-transport layer 1112. The weight ratio of DBTBIm-III to PCBA1BP and Ir(ppy)$_3$ was adjusted to 1:0.25:0.08 (=DBTBIm-III:PCBA1BP:Ir(ppy)$_3$). The thickness of the first light-emitting layer 1113a was set to 20 nm.

Furthermore, DBTBIm-III and Ir(ppy)$_3$ were co-evaporated, whereby the second light-emitting layer 1113b was formed over the first light-emitting layer 1113a. The weight ratio of DBTBIm-III to Ir(ppy)$_3$ was adjusted to 1:0.08 (=DBTBIm-III:Ir(ppy)$_3$). The thickness of the second light-emitting layer 1113b was set to 20 nm.

Then, over the second light-emitting layer 1113b, a 15-nm-thick layer of DBTBIm-III and, a 15-nm-thick layer of BPhen were deposited on the DBTBIm-III layer, whereby the electron-transport layer 1114 including DBTBIm-III and BPhen was formed.

Further, a 1-nm-thick film of lithium fluoride (LiF) was formed over the electron-transport layer 1114 by evaporation, whereby the electron-injection layer 1115 was formed.

Lastly, a 200-nm-thick film of aluminum was formed by evaporation to form the second electrode 1103 functioning as a cathode. Thus, Light-emitting Element 5 of this example was fabricated.

Note that, in the above evaporation process, evaporation was all performed by a resistance heating method.

Light-emitting Elements 5 and 6 were sealed in a glove box containing a nitrogen atmosphere so as not to be exposed to air. Then, operation characteristics of these elements were measured. Note that the measurement was carried out at room temperature (in the atmosphere kept at 25° C.).

Figure 32:
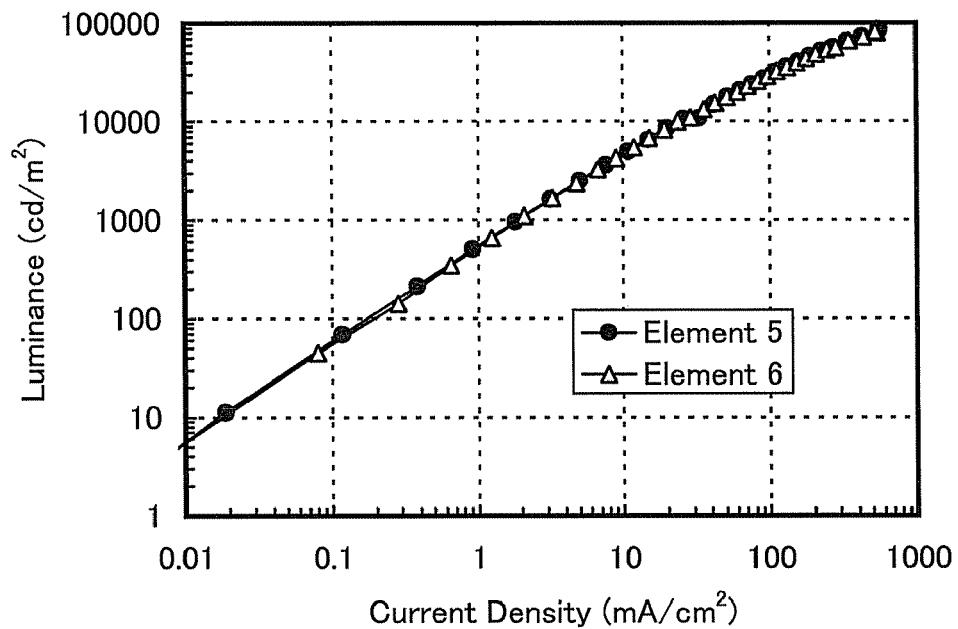
FIG. 32 illustrates current density vs. luminance characteristics of Light-emitting Elements 5 and 6.
Figure 33:
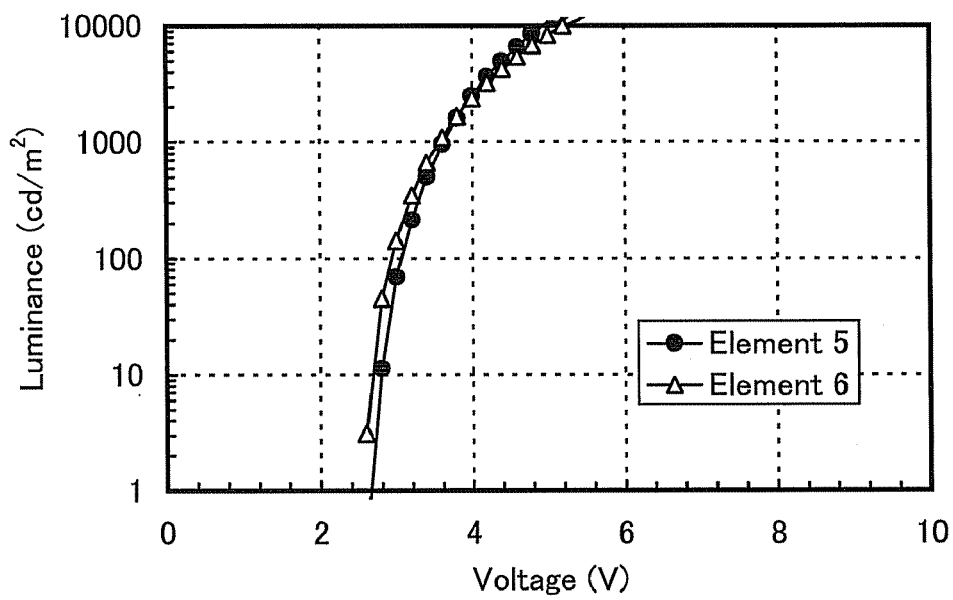
FIG. 33 illustrates voltage vs. luminance characteristics of Light-emitting Elements 5 and 6.
Figure 34:
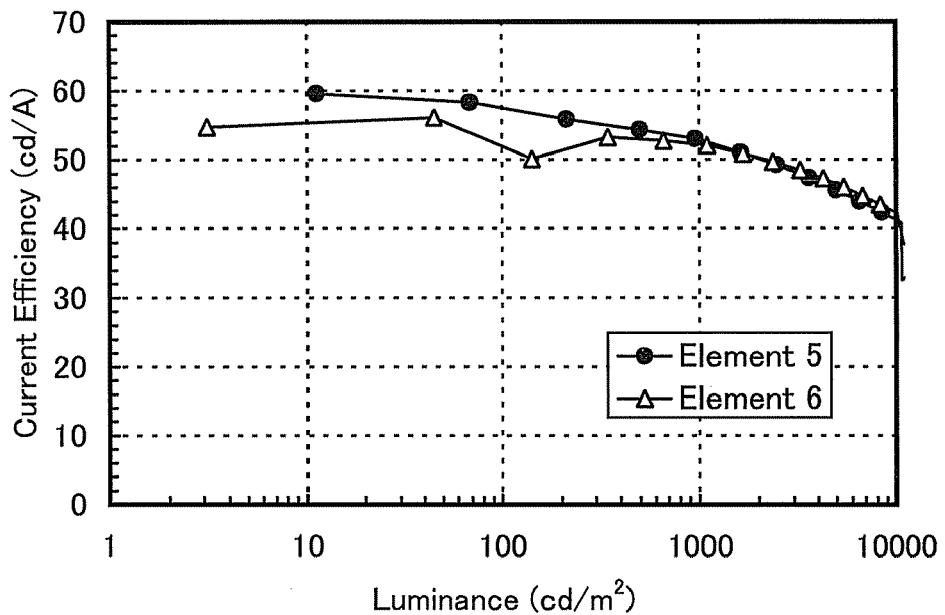
FIG. 34 illustrates luminance vs. current efficiency characteristics of Light-emitting Elements 5 and 6.
Figure 35:
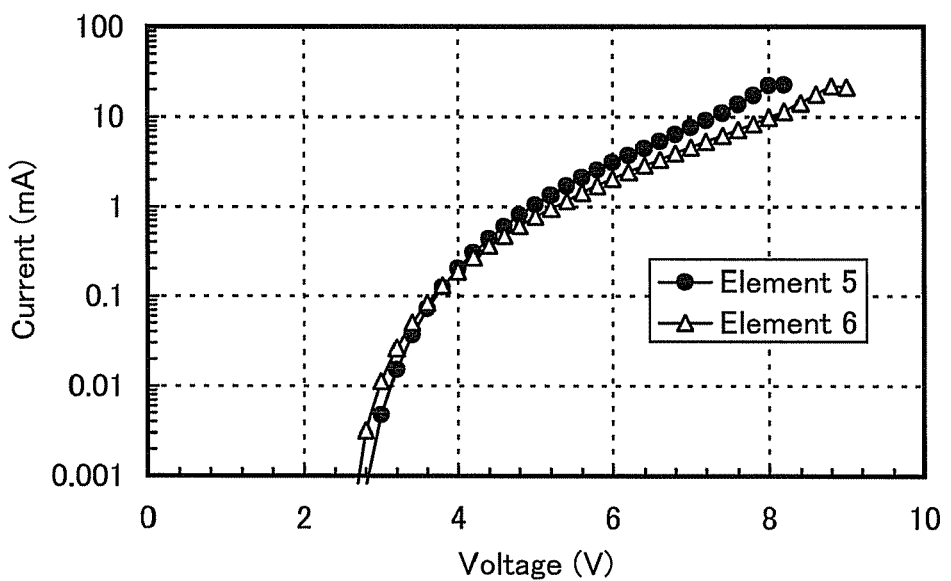
FIG. 35 illustrates voltage vs. current characteristics of Light-emitting Elements 5 and 6.

FIG. 32 shows the current density vs. luminance characteristics of Light-emitting Elements 5 and 6. In FIG. 32, the horizontal axis represents current density (mA/cm$^2$) and the vertical axis represents luminance (cd/m$^2$). FIG. 33 shows the voltage vs. luminance characteristics. In FIG. 33, the horizontal axis represents applied voltage (V) and the vertical axis represents luminance (cd/m$^2$). FIG. 34 shows the luminance vs. current efficiency characteristics. In FIG. 34, the horizontal axis represents luminance (cd/m$^2$) and the vertical axis represents current efficiency (cd/A). FIG. 35 shows the voltage vs. current characteristics. In FIG. 35, the horizontal axis represents voltage (V) and the vertical axis represents current (mA).

The CIE chromaticity coordinates of Light-emitting Element 5 at a luminance of 961 cd/m$^2$ were as follows: (x, y)=(0.33, 0.61), and those of Light-emitting Element 6 at a luminance of 1095 cd/m$^2$ were as follows: (x, y)=(0.34, 0.61). Thus, Light-emitting Elements 5 and 6 are found to emit light from Ir(ppy)$_3$.

FIG. 34 demonstrates that both Light-emitting Elements 5 and 6, which were fabricated, have current efficiency.

As seen from FIG. 33 and FIG. 35, luminance of each of Light-emitting Elements 5 and 6 is high at low voltage. This is because Light-emitting Elements 5 and 6 can obtain a large amount of current at low voltage.

As described above, by using DBTBIm-II produced in Example 1 and DBTBIm-III produced in Example 3 as the host materials of the light-emitting layers and also as materials of the electron-transport layers, the light-emitting elements were each able to have high current efficiency.

Figure 36:
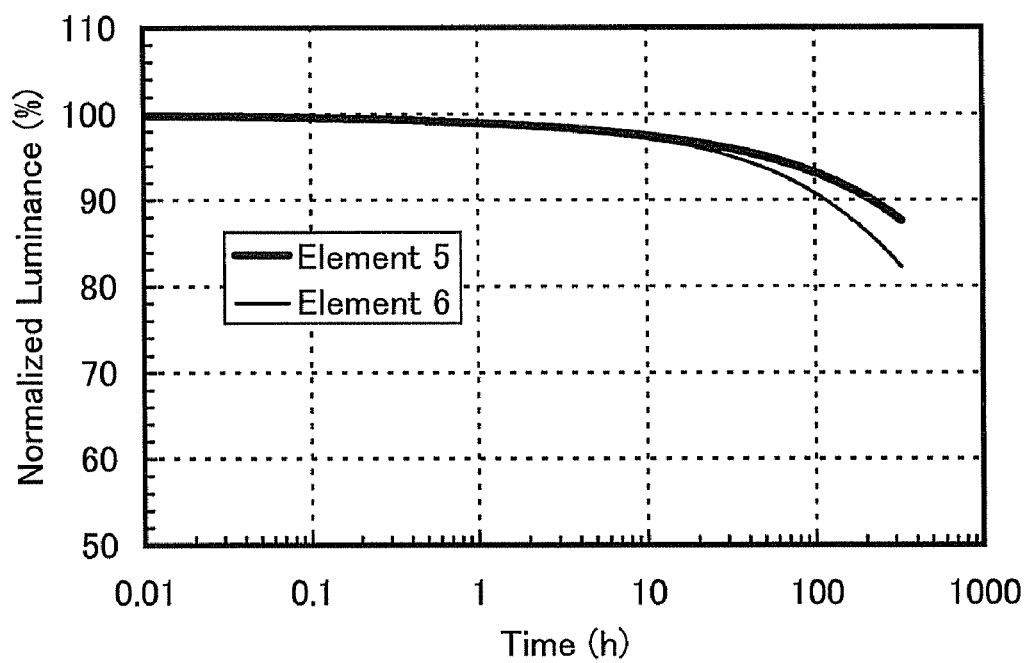
FIG. 36 illustrates results of reliability tests of Light-emitting Elements 5 and 6.

Next, Light-emitting Elements 5 and 6 were subjected to reliability tests. Results of the reliability tests are shown in FIG. 36. In FIG. 36, the vertical axis represents normalized luminance (%) with an initial luminance of 100%, and the horizontal axis represents driving time (h) of the elements. In the reliability tests, Light-emitting Elements 5 and 6 of this example were driven under the conditions where the current density was constant and the initial luminance was 1000 cd/m². FIG. 36 shows that Light-emitting Element 5 kept 88% of the initial luminance after the driving for 330 hours and Light-emitting Element 6 kept 82% of the initial luminance after the driving for 330 hours. These results of the reliability tests show the long lifetime of the light-emitting element to which one embodiment of the present invention is applied.

In particular, Light-emitting Element 5 is found to have higher reliability than Light-emitting Element 6. A structural difference between the heterocyclic compounds of embodiments of the present invention used for Light-emitting Elements 5 and 6, in each of which the heterocyclic compound is used as the host material of the light-emitting layer and as the material of the electron-transport layer, is that a phenyl group which is a kind of aryl group is bonded to each of the 2- and 8-positions of the dibenzothiophene skeleton included in the heterocyclic compound of one embodiment of the present invention in Light-emitting Element 5. The introduction of a phenyl group in the dibenzothiophene skeleton makes a difference in the results of the reliability tests between Light-emitting Elements 5 and 6. It is therefore found that a more reliable light-emitting element can be effectively realized by the introduction of a phenyl group at the 2- and 8-positions of the dibenzothiophene skeleton in the heterocyclic compound of one embodiment of the present invention. Thus, it is thought that the introduction of a bulky aryl group at the 2- and 8-positions of the dibenzothiophene skeleton improves the film stability and leads to extension of lifetime.

Example 9

In this example, a light-emitting element of one embodiment of the present invention will be described referring to FIG. 41. The chemical formulae of materials used in this example are illustrated below. Note that the materials the chemical formulae of which are described above will be omitted.

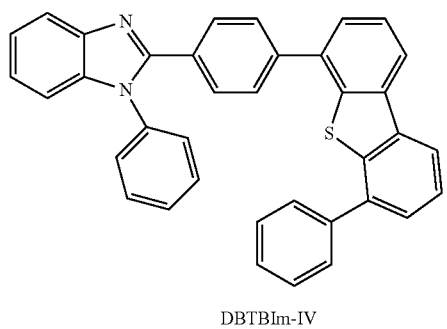 [SMILES: c1ccc(-c2cccc3c2sc2c(-c4ccc(-c5nc6ccccc6n5-c5ccccc5)cc4)cccc23)cc1]

DBTBIm-IV (Light-Emitting Element 7)

First, ITSO was deposited by a sputtering method on the glass substrate 1100, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately $10^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about $10^{-4}$ Pa. Then, by an evaporation method using resistance heating, BPAFLP and molybdenum(VI) oxide were co-evaporated to form the hole-injection layer 1111 over the first electrode 1101. The thickness of the hole-injection layer 1111 was 50 nm, and the weight ratio of BPAFLP to molybdenum(VI) oxide was controlled to be 4:2 (=BPAFLP:molybdenum(VI) oxide). Note that the co-evaporation method refers to an evaporation method in which evaporation is carried out from a plurality of evaporation sources at the same time in one treatment chamber.

Next, BPAFLP was deposited to a thickness of 10 nm over the hole-injection layer 1111, whereby the hole-transport layer 1112 was formed.

Further, 2-[4-(6-phenyldibenzothiophen-4-yl)phenyl]-1-phenyl-1H-benzimidazole (abbreviation: DBTBIm-IV) synthesized in Example 4, PCBA1BP, and Ir(ppy)₃ were co-evaporated, whereby the first light-emitting layer 1113a was formed over the hole-transport layer 1112. The weight ratio of DBTBIm-IV to PCBA1BP and Ir(ppy)₃ was adjusted to 1:0.20:0.08 (=DBTBIm-IV:PCBA1BP:Ir(ppy)₃). The thickness of the first light-emitting layer 1113a was set to 20 nm.

Furthermore, DBTBIm-IV and Ir(ppy)₃ were co-evaporated, whereby the second light-emitting layer 1113b was formed over the first light-emitting layer 1113a. The weight ratio of DBTBIm-IV to Ir(ppy)₃ was adjusted to 1:0.08 (=DBTBIm-IV:Ir(ppy)₃). The thickness of the second light-emitting layer 1113b was set to 20 nm.

Then, over the second light-emitting layer 1113b, a 15-nm-thick layer of DBTBIm-IV and, a 15-nm-thick layer of BPhen were deposited on the DBTBIm-IV layer, whereby the electron-transport layer 1114 including DBTBIm-IV and BPhen was formed.

Further, a 1-nm-thick film of lithium fluoride (LiF) was formed over the electron-transport layer 1114 by evaporation, whereby the electron-injection layer 1115 was formed.

Lastly, a 200-nm-thick film of aluminum was formed by evaporation to form the second electrode 1103 functioning as a cathode. Thus, Light-emitting Element 7 of this example was fabricated.

Note that, in the above evaporation process, evaporation was all performed by a resistance heating method.

Table 4 shows an element structure of Light-emitting Element 7 formed as described above.

TABLE 4

| | 1st electrode | HIL | HTL | 1st EmL | 2nd EmL | ETL | EIL | 2ndd electrode |
|---|---|---|---|---|---|---|---|---|
| Light-emitting Element 7 | ITSO 110 nm | BPAFLP:MoOx (=4:2) 50 nm | BPAFLP 10 nm | DBTBIm-IV:PCBA1BP:Ir(ppy)$_3$ (=1:0.20:0.08) 20 nm | DBTBIm-IV:Ir(ppy)$_3$ (=1:0.08) 20 nm | DBTBIm-IV 15 nm | BPhen 15 nm | LiF 1 nm | Al 200 nm |

Light-emitting Element 7 was sealed in a glove box containing a nitrogen atmosphere so as not to be exposed to air. Then, operation characteristics of the element were measured. Note that the measurement was carried out at room temperature (in the atmosphere kept at 25° C.).

Figure 37:
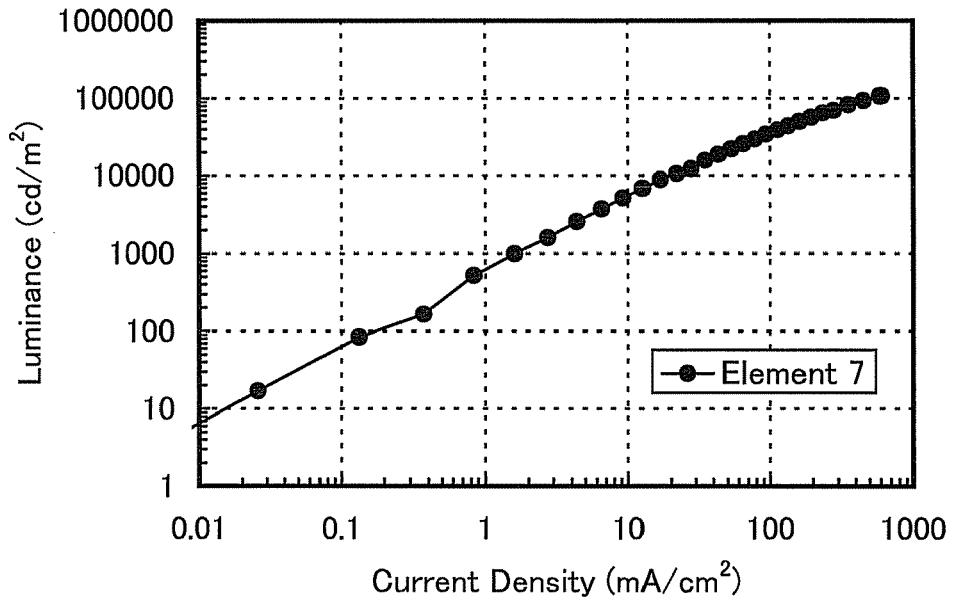
FIG. 37 illustrates current density vs. luminance characteristics of Light-emitting Element 7.
Figure 38:
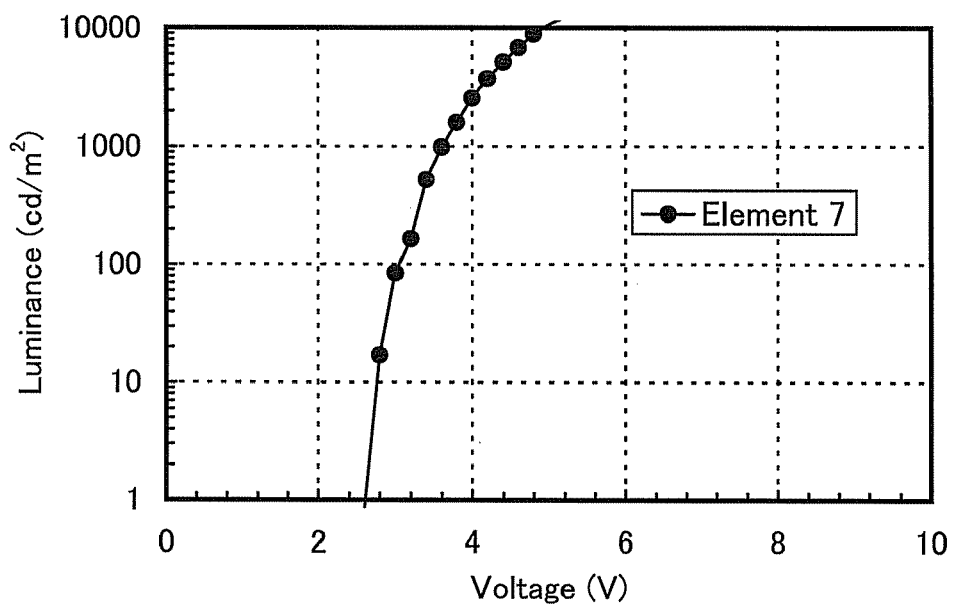
FIG. 38 illustrates voltage vs. luminance characteristics of Light-emitting Element 7.
Figure 39:
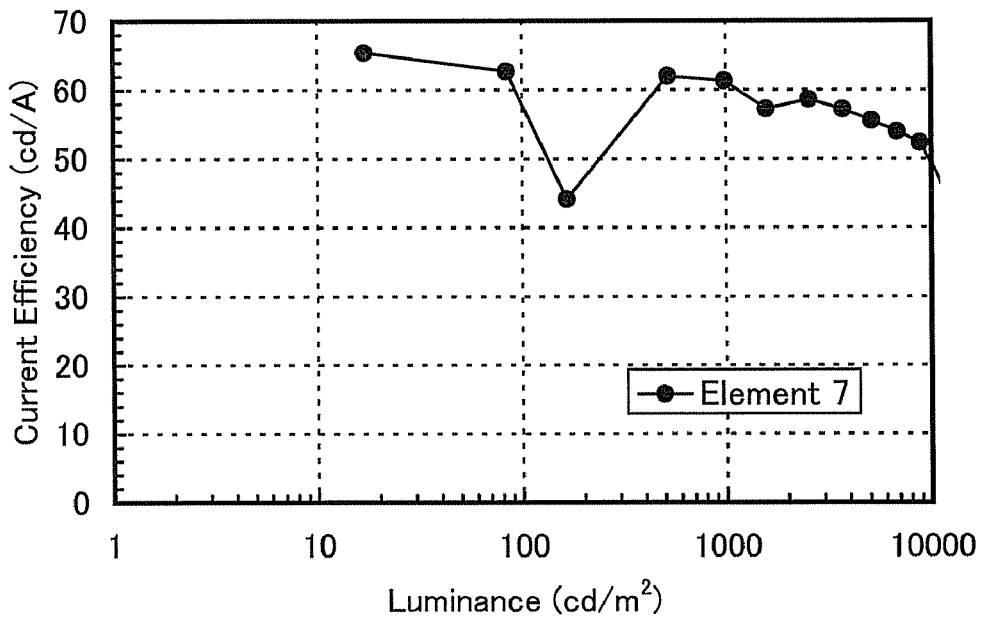
FIG. 39 illustrates luminance vs. current efficiency characteristics of Light-emitting Element 7.
Figure 40:
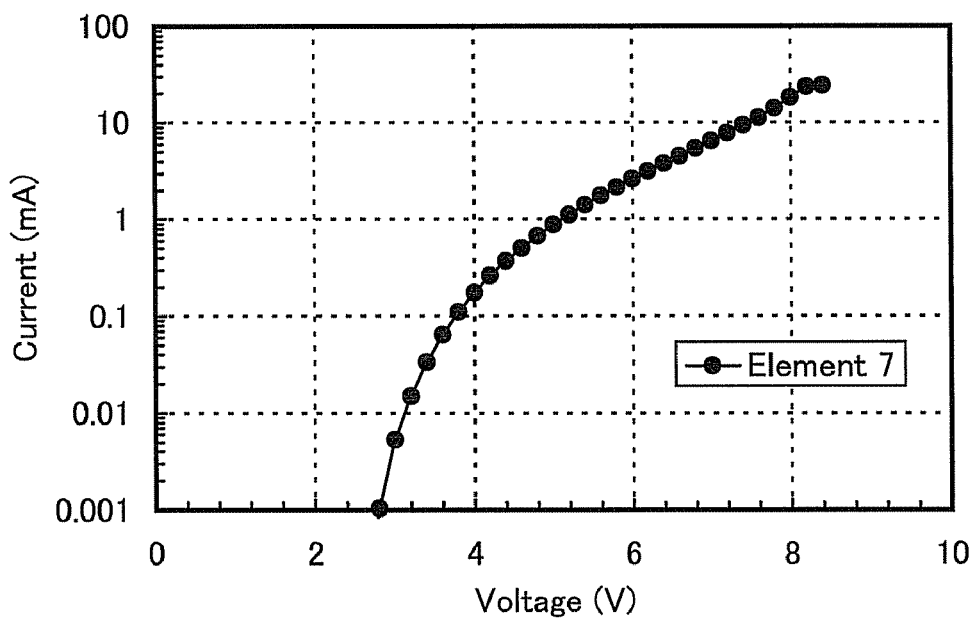
FIG. 40 illustrates voltage vs. current characteristics of Light-emitting Element 7.

FIG. 37 shows the current density vs. luminance characteristics of Light-emitting Element 7. In FIG. 37, the horizontal axis represents current density (mA/cm$^2$) and the vertical axis represents luminance (cd/m$^2$). FIG. 38 shows the voltage vs. luminance characteristics. In FIG. 38, the horizontal axis represents applied voltage (V) and the vertical axis represents luminance (cd/m$^2$). FIG. 39 shows the luminance vs. current efficiency characteristics. In FIG. 39, the horizontal axis represents luminance (cd/m$^2$) and the vertical axis represents current efficiency (cd/A). FIG. 40 shows the voltage vs. current characteristics. In FIG. 40, the horizontal axis represents voltage (V) and the vertical axis represents current (mA).

The CIE chromaticity coordinates of Light-emitting Element 7 at a luminance of 983 cd/m$^2$ were as follows: (x, y)=(0.34, 0.61). Thus, Light-emitting Element 7 is found to emit light from Ir(ppy)$_3$.

As seen from FIG. 38 and FIG. 40, Light-emitting Element 7 which was fabricated achieves high luminance at low voltage. This is because Light-emitting Element 7 can obtain a large amount of current at low voltage. Further, FIG. 39 demonstrates that Light-emitting Element 7 has high current efficiency.

As described above, by using DBTBIm-IV produced in Example 4 as the host material of the light-emitting layer and the material for the electron-transport layer, the light-emitting element was able to have high current efficiency.

Example 10

This example will give descriptions of a method of synthesizing 2-[3-(dibenzofuran-4-yl)phenyl]-1-phenyl-1H-benzimidazole (abbreviation: mDBFBIm-II) represented by the following Structural formula (262).

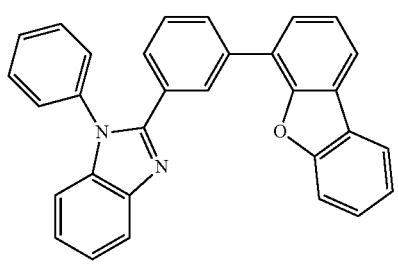

(262)

The synthesis scheme of mDBFBIm-II is illustrated in (B-6).

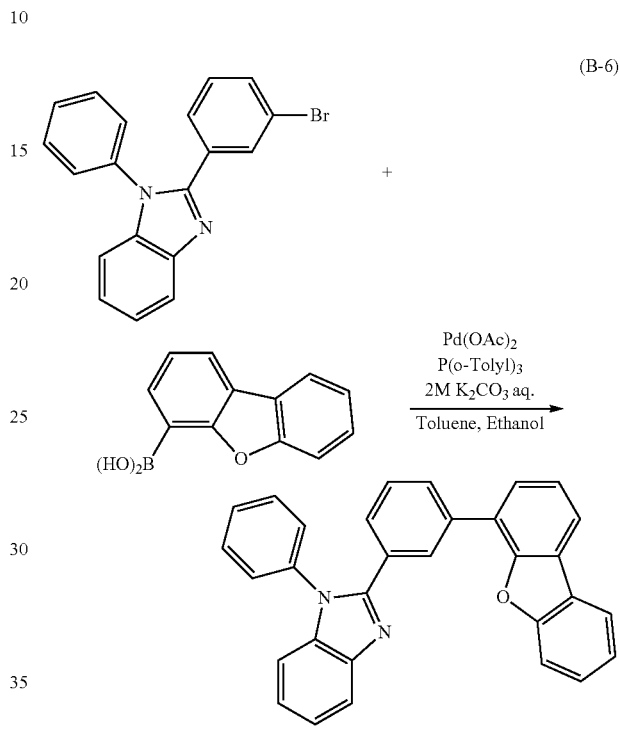

(B-6)

In a 100-mL three-neck flask, a mixture of 1.7 g (5.0 mmol) of 2-(3-bromophenyl)-1-phenyl-1H-benzimidazole, 1.0 g (5.0 mmol) of dibenzofuran-4-boronic acid, 11 mg (0.1 mmol) of palladium(II) acetate, 15 mg (0.1 mmol) of tri(ortho-tolyl)phosphine, 5 mL of toluene, 1 mL of ethanol, and 5 mL of a 2 mol/L aqueous solution of potassium carbonate was stirred to be degassed under reduced pressure. Then, the mixture was heated and stirred at 90° C. for 4.5 hours under a nitrogen stream.

After that, 50 mL, of toluene was added to this mixture solution, and the organic layer of the resulting suspension was suction filtered through Celite (produced by Wako Pure Chemical Industries, Ltd., Catalog No. 531-16855). The resulting filtrate was concentrated, followed by purification using silica gel column chromatography (the developing solvent was toluene). The obtained fractions were concentrated, and hexane was added to the mixture, followed by irradiation with ultrasonic waves. A solid was collected by suction filtration, whereby 1.5 g of a white powder was obtained in 69% yield, which was the substance to be produced.

The Rf values of the produced substance and 2-(3-bromophenyl)-1-phenyl-1H-benzimidazole were respectively 0.15 and 0.28, which were found by silica gel thin layer chromatography (TLC) (with a developing solvent containing ethyl acetate to hexane in a ratio of 1 to 10).

A nuclear magnetic resonance (NMR) method identified this produced compound as 2-[3-(dibenzofuran-4-yl)phenyl]-1-phenyl-1H-benzimidazole (abbreviation: mDBFBIm-II).

$^1$H NMR data of the obtained substance are as follows: $^1$H NMR (CDCl$_3$, 300 MHz): δ (ppm)=7.28 (d, J=4.8, 2H), 7.32-7.64 (m, 13H), 7.89-7.97 (m, 3H), 8.02 (d, J=7.8, 1H), 8.08 (s, 1H).

Figure 42A:
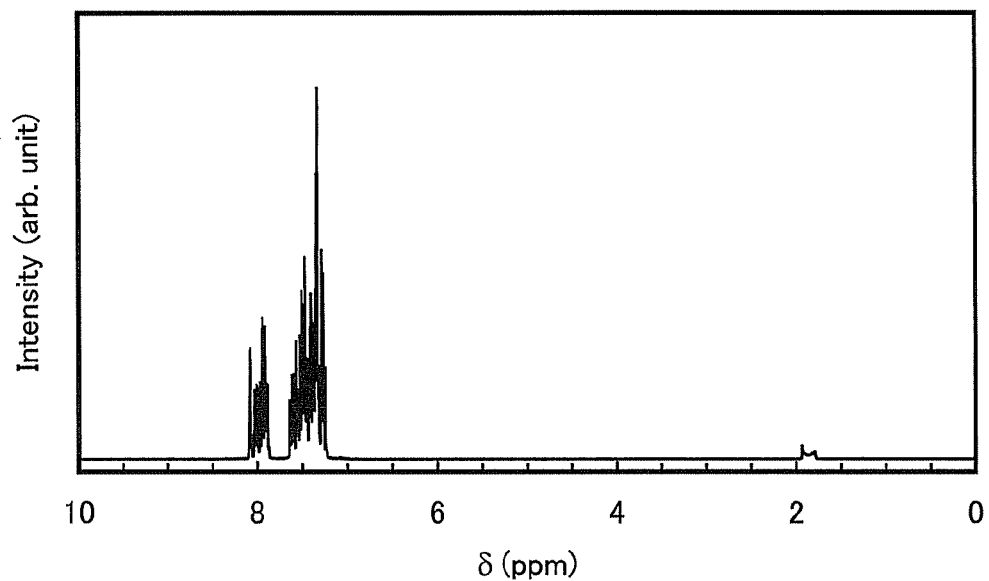
FIGS. 42A and 42B illustrate $^1$H NMR charts of 2-[3-(dibenzofuran-4-yl)phenyl]-1-phenyl-1H-benzimidazole.
Figure 42B:
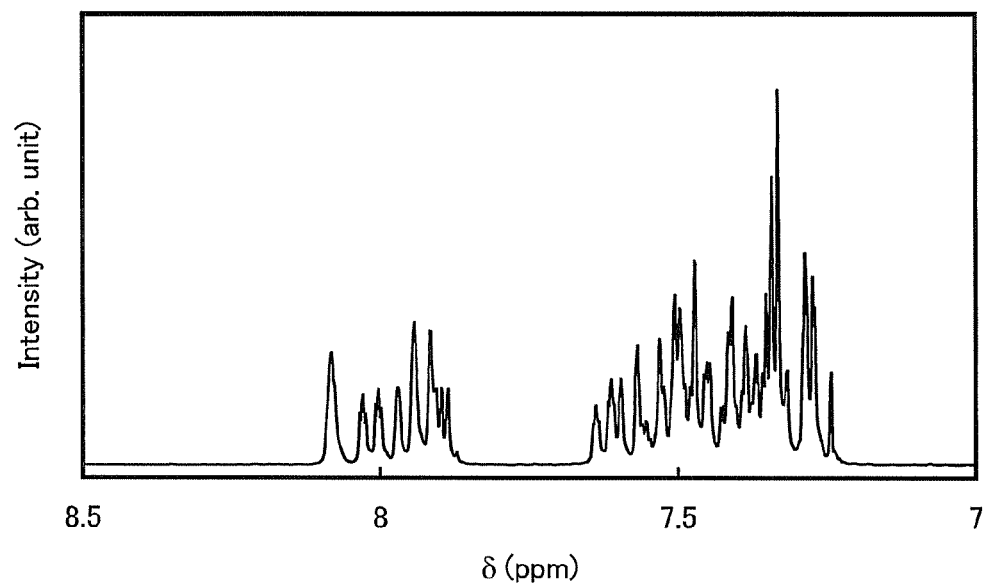

FIGS. 42A and 42B illustrate the $^1$H NMR charts. Note that FIG. 42B is a chart showing an enlarged part of FIG. 42A in the range of 7.0 ppm to 8.5 ppm.

Further, the absorption spectrum and the emission spectrum were measured each for a toluene solution and a thin film of mDBFBIm-II. The absorption spectrum was measured using an ultraviolet-visible spectrophotometer (V-550, produced by JASCO Corporation). The measurements were performed with samples prepared in such a manner that the solution was put in a quartz cell while the thin film was obtained by evaporation onto a quartz substrate. The absorption spectrum of the solution was obtained by subtracting the absorption spectra of quartz and toluene from those of quartz and the solution, and the absorption spectrum of the thin film was obtained by subtracting the absorption spectrum of a quartz substrate from those of the quartz substrate and the thin film. With the toluene solution, an absorption peak was observed at around 292 nm, and an emission wavelength peak was 350 nm (excitation wavelength: 295 nm). In the case of the thin film, an absorption peak was observed at around 294 nm, and an emission wavelength peak was 364 nm (excitation wavelength: 303 nm).

Example 11

In this example, a light-emitting element of one embodiment of the present invention will be described referring to FIG. 41. The chemical formulae of materials used in this example are illustrated below.

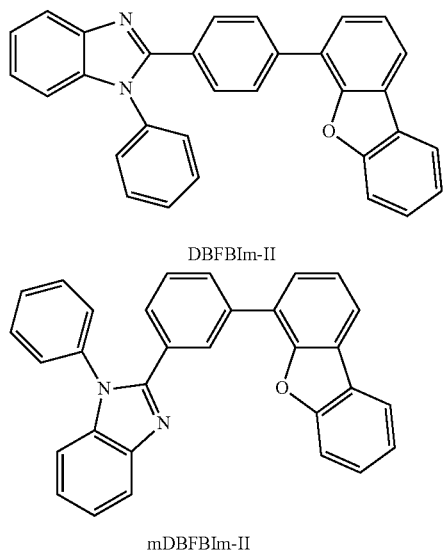

DBFBIm-II mDBFBIm-II

Methods of fabricating Light-emitting Element 8 and Light-emitting Element 9 of this example will now be described.

(Light-Emitting Element 8)

First, ITSO was deposited by a sputtering method on the glass substrate 1100, whereby the first electrode 1101 was formed. Its thickness was 110 nm and the electrode area was 2 mm×2 mm. Here, the first electrode 1101 is an electrode that functions as an anode of the light-emitting element.

Next, as pretreatment for forming the light-emitting element over the substrate 1100, a surface of the substrate was washed with water, baked at 200° C. for one hour, and subjected to UV ozone treatment for 370 seconds.

After that, the substrate 1100 was transferred into a vacuum evaporation apparatus where the pressure had been reduced to approximately 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 was fixed to a substrate holder in a vacuum evaporation apparatus so that a surface of the substrate 1100 on which the first electrode 1101 was formed faced downward. The pressure in the vacuum evaporation apparatus was reduced to about 10$^{-4}$ Pa. Then, by an evaporation method using resistance heating, BPAFLP and molybdenum(VI) oxide were co-evaporated to form the hole-injection layer 1111 over the first electrode 1101. The thickness of the hole-injection layer 1111 was 50 nm, and the weight ratio of BPAFLP to molybdenum(VI) oxide was controlled to be 4:2 (=BPAFLP:molybdenum(VI) oxide). Note that the co-evaporation method refers to an evaporation method in which evaporation is carried out from a plurality of evaporation sources at the same time in one treatment chamber.

Next, BPAFLP was deposited to a thickness of 10 nm over the hole-injection layer 1111, whereby the hole-transport layer 1112 was formed.

Further, 2-[4-(dibenzofuran-4-yl)phenyl]-1-phenyl-1H-benzimidazole (abbreviation: DBFBIm-II) synthesized in Example 5, PCBA1BP, and Ir(ppy)$_3$ were co-evaporated, whereby the first light-emitting layer 1113a was formed over the hole-transport layer 1112. The weight ratio of DBFBIm-II to PCBA1BP and Ir(ppy)$_3$ was adjusted to 1:0.25:0.06 (=DBFBIm-II:PCBA1BP:Ir(ppy)$_3$). The thickness of the first light-emitting layer 1113a was set to 20 nm.

Furthermore, DBFBIm-II and Ir(ppy)$_3$ were co-evaporated, whereby the second light-emitting layer 1113b was formed over the first light-emitting layer 1113a. The weight ratio of DBFBIm-II to Ir(ppy)$_3$ was adjusted to 1:0.06 (=DBFBIm-II:Ir(ppy)$_3$). The thickness of the second light-emitting layer 1113b was set to 20 nm.

Then, over the second light-emitting layer 1113b, a 15-nm-thick layer of Alq and, a 15-nm-thick layer of BPhen were deposited on the Alq layer, whereby the electron-transport layer 1114 including Alq and BPhen was formed.

Further, a 1-nm-thick film of LiF was formed over the electron-transport layer 1114 by evaporation, whereby the electron-injection layer 1115 was formed.

Lastly, a 200-nm-thick film of aluminum was formed by evaporation to form the second electrode 1103 functioning as a cathode. Thus, Light-emitting Element 8 of this example was fabricated.

Note that, in the above evaporation process, evaporation was all performed by a resistance heating method.

(Light-Emitting Element 9)

The first light-emitting layer 1113a of Light-emitting Element 9 was formed by co-evaporation of 2-[3-(dibenzofuran-4-yl)phenyl]-1-phenyl-1H-benzimidazole (abbreviation: mDBFBIm-II) synthesized in Example 10, PCBA1BP, and Ir(ppy)$_3$, instead of the materials used for Light-emitting Element 8. The weight ratio of mDBFBIm-II to PCBA1BP and Ir(ppy)$_3$ was adjusted to 1:0.25:0.06 (=mDBFBIm-II:PCBA1BP:Ir(ppy)$_3$). The thickness of the first light-emitting layer 1113a was set to 20 nm.

Further, the second light-emitting layer 1113b of Light-emitting Element 9 was formed by co-evaporation of mDBFBIm-II and Ir(ppy)$_3$, instead of the materials used for Light-emitting Element 8. The weight ratio of mDBFBIm-II to Ir(ppy)$_3$ was adjusted to 1:0.06 (=mDBFBIm-II:Ir(ppy)$_3$). The thickness of the second light-emitting layer 1113*b* was set to 20 nm. The structure other than the first light-emitting layer 1113*a* and the second light-emitting layer 1113*b* was formed in the same manner as that of Light-emitting Element 8.

Table 5 shows element structures of Light-emitting Elements 8 and 9 formed as described above.

TABLE 5

| | 1st electrode | HIL | HTL | 1st EmL | 2nd EmL | | ETL | EIL | 2ndd electrode |
|---|---|---|---|---|---|---|---|---|---|
| Light-emitting Element 8 | ITSO 110 nm | BPAFLP:MoOx (=4:2) 50 nm | BPAFLP 10 nm | DBTBIm-II:PCBA1BP:Ir(ppy)$_3$ (=1:0.25:0.06) 20 nm | DBTBIm-II:Ir(ppy)$_3$ (=1:0.06) 20 nm | | Alq 15 nm | BPhen 15 nm | LiF 1 nm | Al 200 nm |
| Light-emitting Element 9 | ITSO 110 nm | BPAFLP:MoOx (=4:2) 50 nm | BPAFLP 10 nm | mDBFBIm-II:PCBA1BP:Ir(ppy)$_3$ (=1:0.25:0.06) 20 nm | mDBFBIm-II:Ir(ppy)$_3$ (=1:0.06) 20 nm | | Alq 15 nm | BPhen 15 nm | LiF 1 nm | Al 200 nm |

Light-emitting Elements 8 and 9 were sealed in a glove box containing a nitrogen atmosphere so as not to be exposed to air. Then, operation characteristics of these elements were measured. Note that the measurement was carried out at room temperature (in the atmosphere kept at 25° C.).

Figure 43:
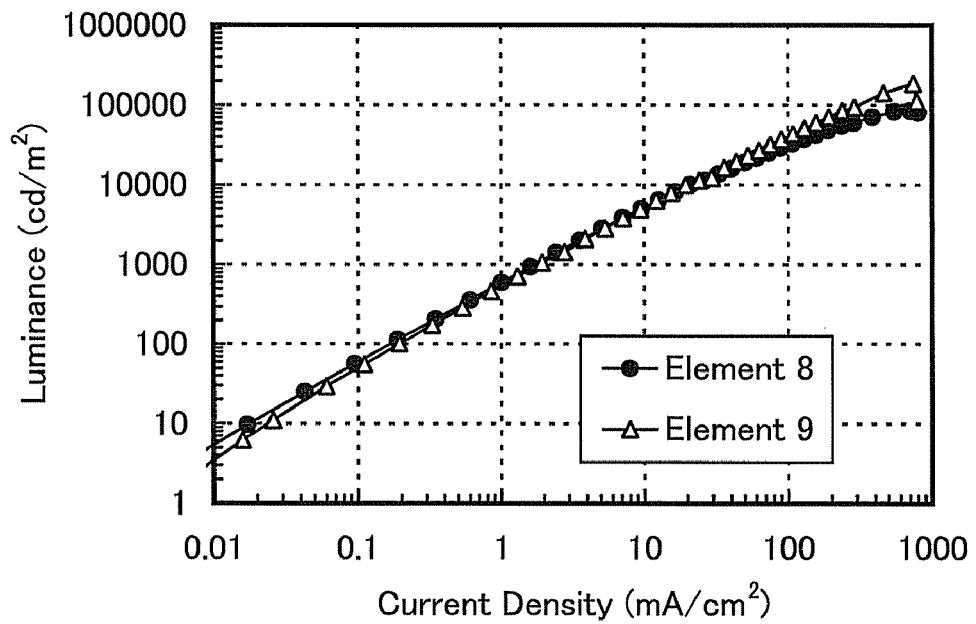
FIG. 43 illustrates current density vs. luminance characteristics of Light-emitting Elements 8 and 9.
Figure 44:
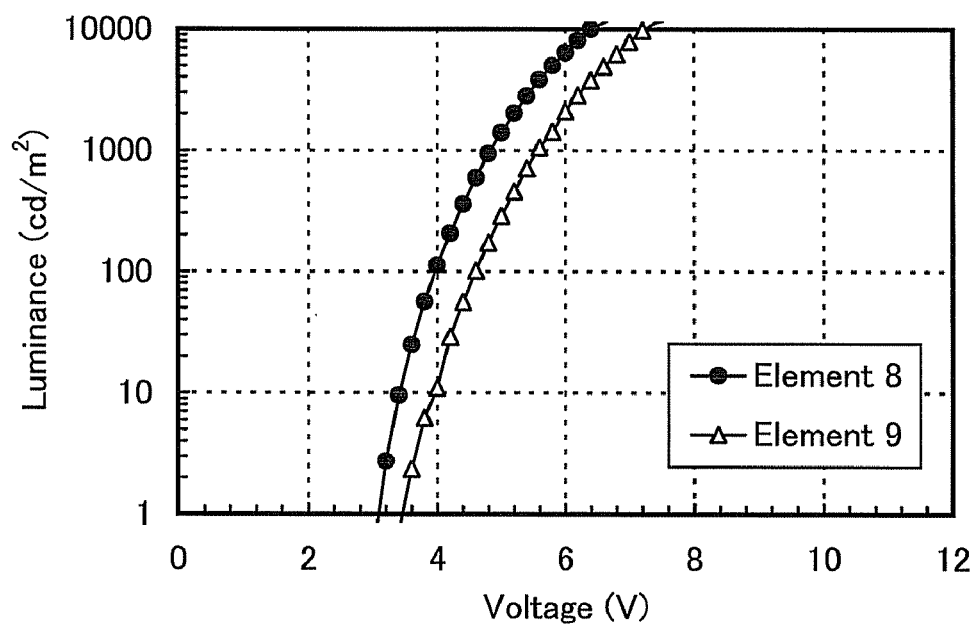
FIG. 44 illustrates voltage vs. luminance characteristics of Light-emitting Elements 8 and 9.
Figure 45:
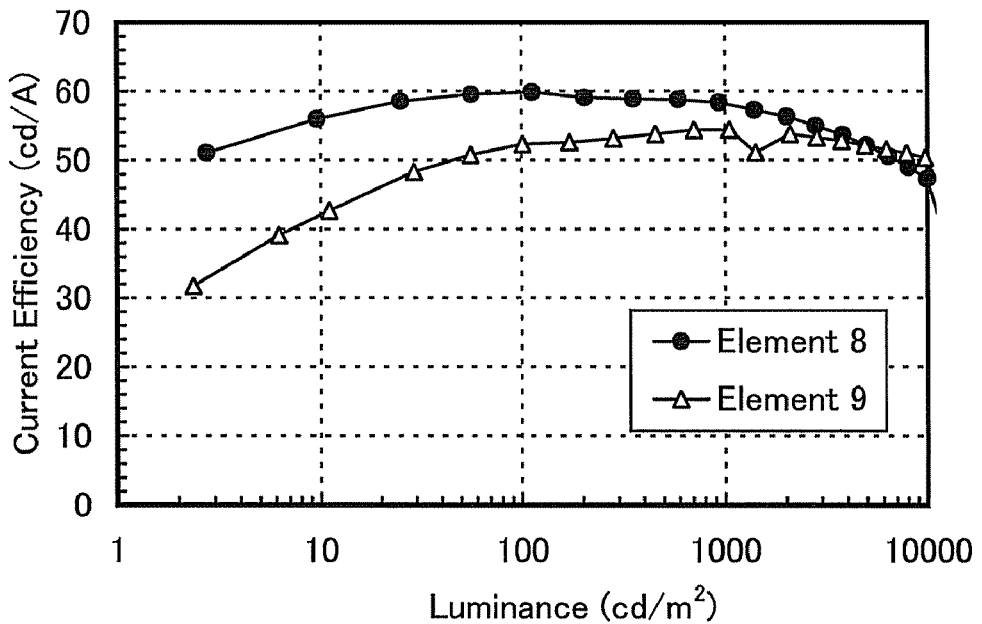
FIG. 45 illustrates luminance vs. current efficiency characteristics of Light-emitting Elements 8 and 9.
Figure 46:
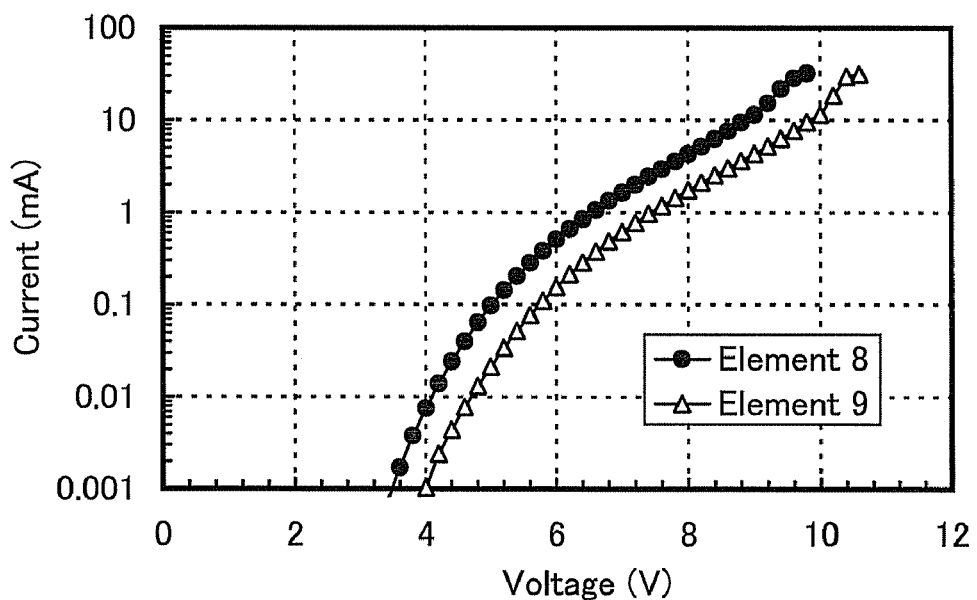
FIG. 46 illustrates voltage vs. current characteristics of Light-emitting Elements 8 and 9.

FIG. 43 shows the current density vs. luminance characteristics of Light-emitting Elements 8 and 9. In FIG. 43, the horizontal axis represents current density (mA/cm$^2$) and the vertical axis represents luminance (cd/m$^2$). FIG. 44 shows the voltage vs. luminance characteristics. In FIG. 44, the horizontal axis represents applied voltage (V) and the vertical axis represents luminance (cd/m$^2$). FIG. 45 shows the luminance vs. current efficiency characteristics. In FIG. 45, the horizontal axis represents luminance (cd/m$^2$) and the vertical axis represents current efficiency (cd/A). FIG. 46 shows the voltage vs. current characteristics. In FIG. 46, the horizontal axis represents voltage (V) and the vertical axis represents current (mA).

The CIE chromaticity coordinates of Light-emitting Element 8 at a luminance of 936 cd/m$^2$ were as follows: (x, y)=(0.33, 0.61), and those of Light-emitting Element 9 at a luminance of 1054 cd/m$^2$ were as follows: (x, y)=(0.32, 0.61). Thus, Light-emitting Elements 8 and 9 are found to emit light from Ir(ppy)$_3$.

FIG. 45 demonstrates that both Light-emitting Elements 8 and 9, which were fabricated, have current efficiency.

As seen from FIG. 44 and FIG. 46, Light-emitting Element 8 shows higher luminance than Light-emitting Element 9 at the same voltage. This is because Light-emitting Element 8 can obtain a larger amount of current than Light-emitting Element 9.

A structural difference between the heterocyclic compounds of embodiments of the present invention used for Light-emitting Elements 8 and 9, in each of which the heterocyclic compound is used as the host material of the light-emitting layer, is that the 2-position of the benzimidazole skeleton and the 4-position of the dibenzofuran skeleton which are included in the heterocyclic compound of one embodiment of the present invention are bonded through a meta-phenylene group in Light-emitting Element 9 while they are bonded through a para-phenylene group in Light-emitting Element 8. Whether the 2-position of the benzimidazole skeleton and the 4-position of the dibenzofuran skeleton are bonded through the meta-phenylene group or the para-phenylene group makes a difference in voltage vs. luminance characteristics between Light-emitting Elements 8 and 9. This reveals that, by having the 2-position of the benzimidazole skeleton and the 4-position of the dibenzofuran skeleton which are bonded through the para-phenylene group, the heterocyclic compound of one embodiment of the present invention is effective in enhancing voltage vs. luminance characteristics.

As described above, by using DBFBIm-II produced in Example 5 and mDBFBIm-II produced in Example 10 as the host materials of the light-emitting layers, the light-emitting elements were each able to have high current efficiency.

Reference Example 1

A method for synthesizing 4-phenyl-4'-(9-phenylfluoren-9-yl)triphenylamine (abbreviation: BPAFLP) used in Examples 6 to 9 above will be specifically described. The structure of BPAFLP is illustrated below.

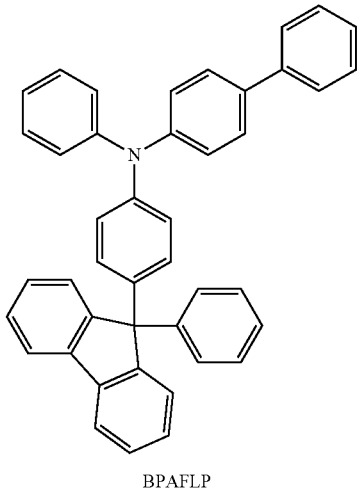 [SMILES: c1ccc(-c2ccc(N(c3ccccc3)c3ccc(C4(c5ccccc5)c5ccccc5-c5ccccc54)cc3)cc2)cc1]

BPAFLP

Step 1: Synthesis method of 9-(4-bromophenyl)-9-phenylfluorene

In a 100-mL three-neck flask, 1.2 g (50 mmol) of magnesium was heated and stirred under reduced pressure for 30 minutes to be activated. After the flask was cooled to room temperature and was made to have a nitrogen atmosphere, several drops of dibromoethane were added, so that foam formation and heat generation were confirmed. After 12 g (50 mmol) of 2-bromobiphenyl dissolved in 10 mL of diethyl ether was slowly dripped into this mixture, the mixture was stirred and heated under reflux for 2.5 hours, whereby a Grignard reagent was prepared.

In a 500-mL three-neck flask were put 10 g (40 mmol) of 4-bromobenzophenone and 100 mL of diethyl ether. After the Grignard reagent prepared as above was slowly dripped into this mixture, the mixture was heated and stirred under reflux for 9 hours.

After reaction, this mixture was filtered to give a residue. The residue was dissolved in 150 mL of ethyl acetate, and 1N-hydrochloric acid was added to the mixture, which was then stirred for 2 hours until it was made acid. The organic layer of the liquid was washed with water. Then, magnesium sulfate was added thereto so that moisture is removed. This suspension was filtered, and the resulting filtrate was concentrated to give a substance.

In a 500-mL recovery flask were put this substance, 50 mL of glacial acetic acid, and 1.0 mL of hydrochloric acid. The mixture was heated and stirred under a nitrogen atmosphere at 130° C. for 1.5 hours to be reacted.

After reaction, this reaction mixture solution was filtered to give a residue. The residue was washed with water, an aqueous sodium hydroxide solution, water, and methanol in this order. Then, the mixture was dried to give 11 g of a white powder in 69% yield, which was the substance to be produced. The reaction scheme of the synthesis method is illustrated in the following (C-1).

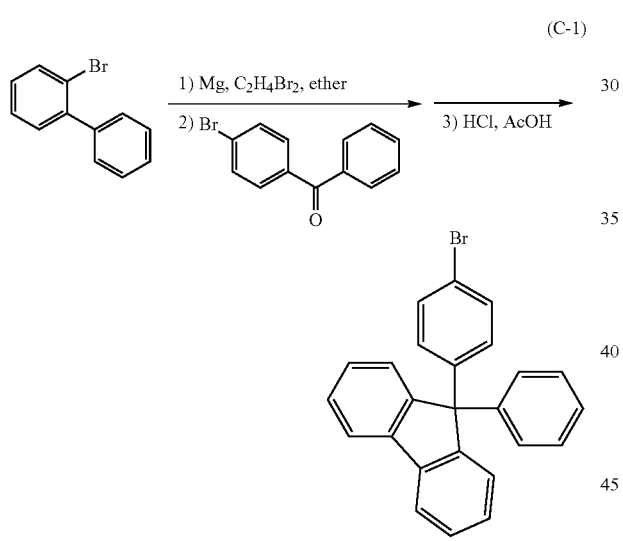

Step 2: Synthesis method of 4-phenyl-4'-(9-phenylfluoren-9-yl)triphenylamine (abbreviation: BPAFLP)

In a 100-mL three-neck flask were put 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide and 23 mg (0.04 mmol) of bis(dibenzylideneacetone)palladium(0). The air in the flask was replaced with nitrogen. Then, 20 mL of dehydrated xylene was added to this mixture. After the mixture was degassed while being stirred under reduced pressure, 0.2 mL (0.1 mmol) of tri(tert-butyl)phosphine (a 10 wt % hexane solution) was added to the mixture. This mixture was heated and stirred under a nitrogen atmosphere at 110° C. for 2 hours to be reacted.

After reaction, 200 mL of toluene was added to the reaction mixture solution, and the resulting suspension was filtered through Florisil (produced by Wako Pure Chemical Industries, Ltd., Catalog No. 540-00135) and Celite (produced by Wako Pure Chemical Industries, Ltd., Catalog No. 531-16855). The filtrate was concentrated, and the resulting substance was purified by silica gel column chromatography (the developing solvent of toluene to hexane in a ratio of 1 to 4). The obtained fractions were concentrated, and acetone and methanol were added to the mixture. The mixture was irradiated with ultrasonic waves and then recrystallized to give 4.1 g of a white powder in 92% yield, which was the substance to be produced. The reaction scheme of the above synthesis method is illustrated in the following (C-2).

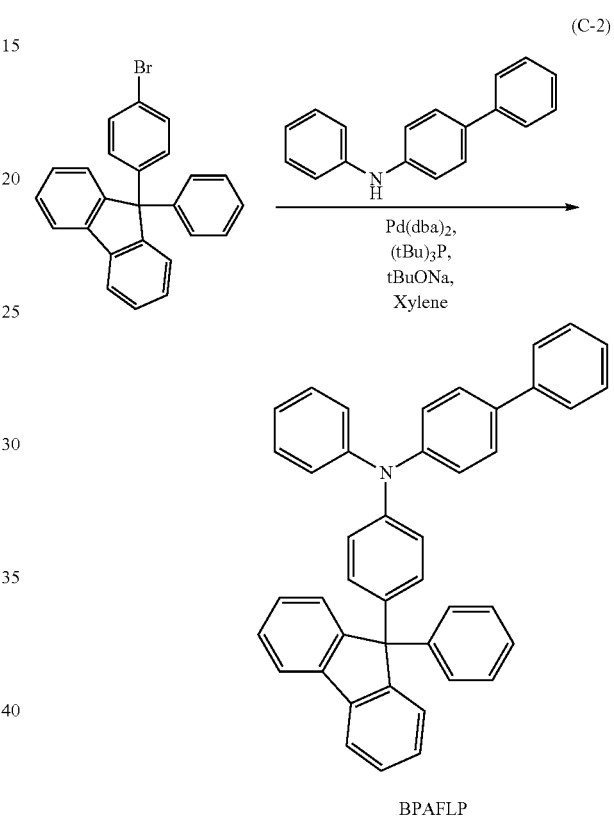

The Rf values of the produced substance, 9-(4-bromophenyl)-9-phenylfluorene, and 4-phenyl-diphenylamine were respectively 0.41, 0.51, and 0.27, which were found by silica gel thin layer chromatography (TLC) (with a developing solvent containing ethyl acetate to hexane in a ratio of 1 to 10).

The compound obtained through the above Step 2 was subjected to a nuclear magnetic resonance (NMR) method. The measurement data are shown below. The measurement results indicate that the obtained compound was BPAFLP, which is a fluorene derivative.

$^1$H NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

Reference Example 2

A method for synthesizing 4-phenyl-4'-(9-phenyl-9H-carbazol-3-yl)triphenylamine (abbreviation: PCBA1BP) used in Examples 6 to 9 above will be specifically described. The structure of PCBA1BP is illustrated below.

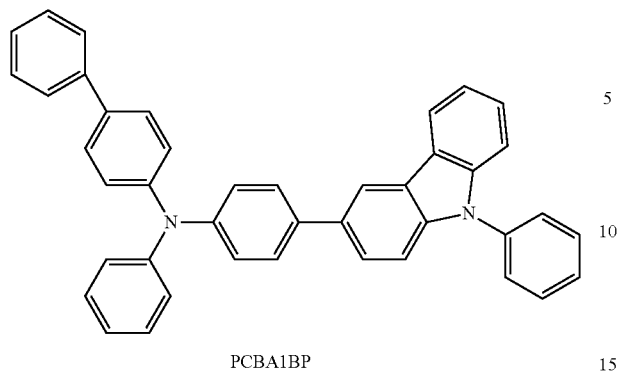

PCBA1BP

Step 1: Synthesis of 4-bromodiphenylamine

The synthesis scheme of 4-bromodiphenylamine in Step 1 is illustrated in the following (D-1).

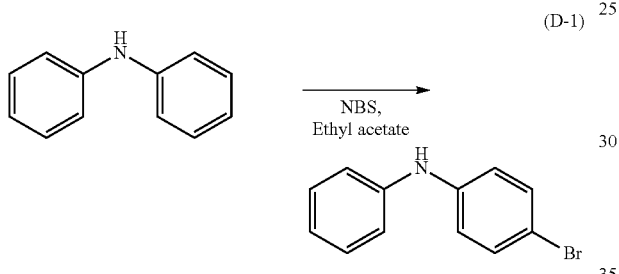

(D-1)

In a 1-L conical flask, 51 g (0.3 mol) of diphenylamine was dissolved in 700 mL of ethyl acetate, and then 54 g (0.3 mol) of N-bromosuccinimide (abbreviation: NBS) was added to this solution. About 300 hours later, this mixture solution was washed with water, and then magnesium sulfate was added thereto to remove moisture. This mixture solution was filtered, the filtrate was concentrated, and the resulting substance was collected. Accordingly, a dark brown oily substance, which was the substance to be produced, was obtained, and the amount and yield of the substance were 70 g and 94%, respectively.

Step 2-1: Synthesis of 3-bromo-9-phenyl-9H-carbazole

The synthesis scheme of 3-bromo-9-phenyl-9H-carbazole in Step 2-1 is illustrated in the following (D-2-1).

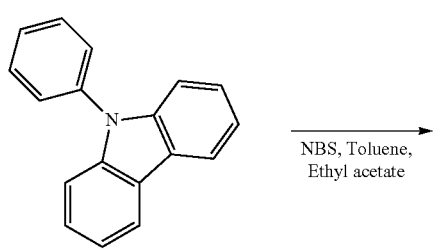

(D-2-1)

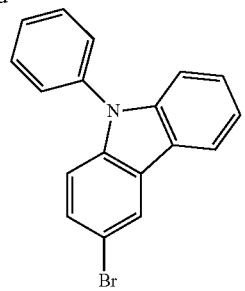

In a 1 L conical flask, 24 g (100 mmol) of 9-phenyl-9H-carbazole, 18 g (100 mmol) of N-bromosuccinimide, 450 mL of toluene, and 200 mL of ethyl acetate were stirred at room temperature for 45 hours. This suspension was washed with water, and magnesium sulfate was added thereto, so that moisture was removed. This suspension was filtered, and the obtained filtrate was concentrated and dried. The amount and yield of a solid, which was the substance to be produced, were 32 g and 99%, respectively.

Step 2-2: Synthesis of 9-phenyl-9H-carbazol-3-boronic acid

The synthesis scheme of 9-phenyl-9H-carbazol-3-boronic acid in Step 2-2 is illustrated in the following (D-2-2).

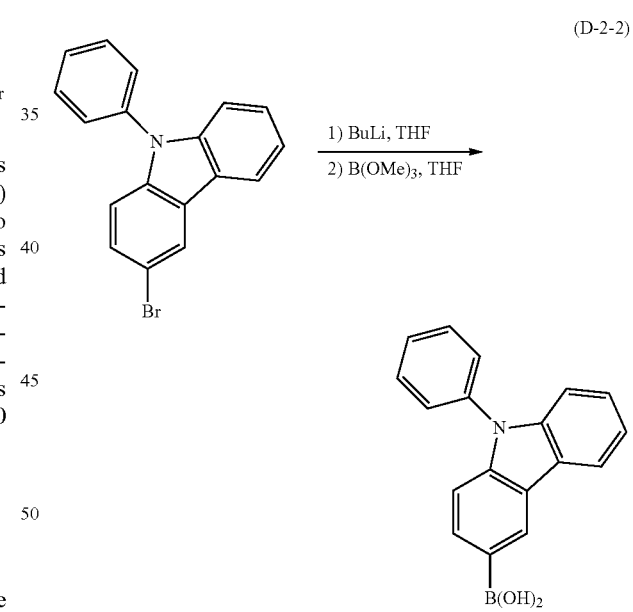

(D-2-2)

In a 500-mL conical flask, 29 g (90 mmol) of 3-bromo-9-phenyl-9H-carbazole and 200 mL of tetrahydrofuran (abbreviation: THF) were stirred at −78° C. to become a solution. After that, 110 mL (69 mmol) of n-butyllithium (a 1.57 mol/L hexane solution) was dripped into this solution. The mixture was stirred at the same temperature for 2 hours. Furthermore, 13 mL (140 mmol) of trimethyl borate was added thereto, and the mixture was stirred at room temperature for 24 hours.

After the reaction, 200 mL of 1.0 mol/L hydrochloric acid was added thereto, and the mixture was stirred at room temperature for 1 hour. This mixture was washed with water, an aqueous sodium hydroxide solution, and water in this order.

Magnesium sulfate was added thereto to remove moisture. This suspension was filtered, the obtained filtrate was concentrated, and chloroform and hexane were added thereto. The mixture was irradiated with ultrasonic waves and then recrystallized. The amount and yield of a white powder, which was the substance to be produced, were 21 g and 80%, respectively.

Step 3: Synthesis of 4-(9-phenyl-9H-carbazol-3-yl)diphenylamine (abbreviated to PCBA)

The synthesis scheme of 4-(9-phenyl-9H-carbazol-3-yl)diphenylamine (abbreviation: PCBA) in Step 3 is illustrated in the following (D-3).

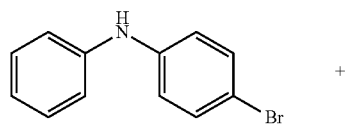

+

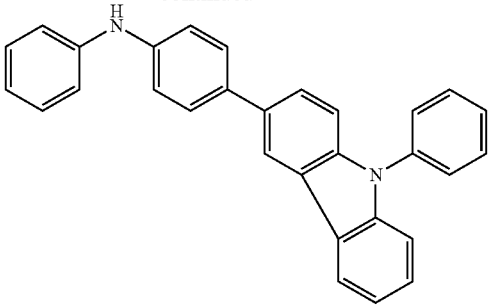

PCBA

In a 500-mL, three-neck flask were put 6.5 g (26 mmol) of 4-bromo-diphenylamine, 7.5 g (26 mmol) of 9-phenyl-9H-carbazole-3-boronic acid, and 400 mg (1.3 mmol) of tri(o-tolyl)phosphine. The air in the flask was replaced with nitrogen. To this mixture were added 100 mL of toluene, 50 mL, of ethanol, and 14 mL (0.2 mol/L) of an aqueous solution of potassium carbonate. Under reduced pressure, this mixture was degassed while being stirred. After the degassing, 67 mg (30 mmol) of palladium(II) acetate was added to the mixture.

This mixture was refluxed at 100° C. for 10 hours. After that, the aqueous layer of this mixture was extracted with toluene. The extracted solution and the organic layer were combined and washed with saturated brine. After magnesium sulfate was added to remove moisture of the organic layer, this mixture was gravity filtered. The obtained filtrate was concentrated to give a pale brown oily substance. The oily substance was purified by silica gel column chromatography (the developing solvent of hexane to toluene in a ratio of 4 to 6). The white solid obtained after the purification was recrystallized from a mixed solvent of dichloromethane and hexane, whereby a white solid which was the substance to be produced was obtained. The amount and yield of the solid were 4.9 g and 45%, respectively.

Step 4: Synthesis of 4-phenyl-4'-(9-phenyl-9H-carbazol-3-yl)triphenylamine (abbreviation: PCBA1BP)

The synthesis scheme of 4-phenyl-4'-(9-phenyl-9H-carbazol-3-yl)triphenylamine (abbreviation: PCBA1BP) in Step 4 is illustrated in the following (D-4).

(D-4)

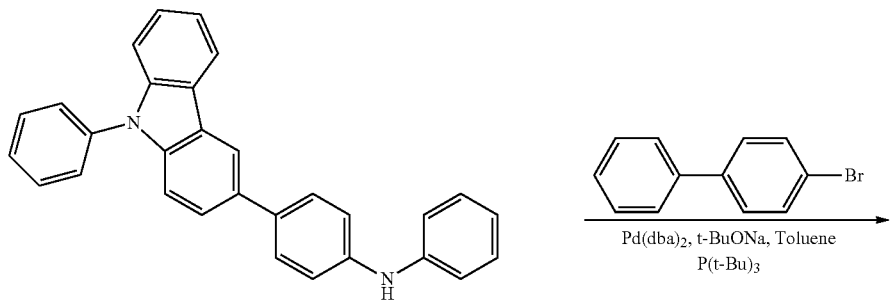

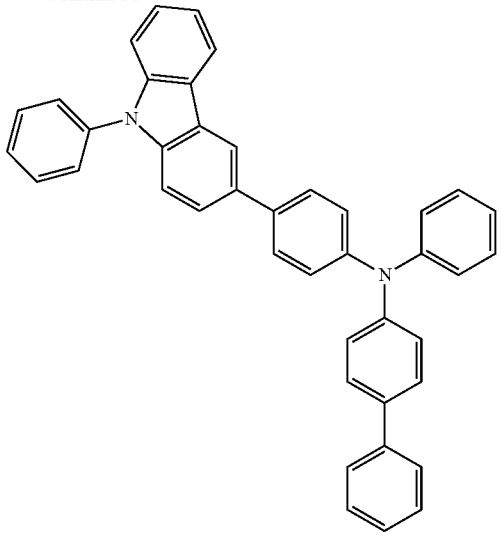

In a 100-mL three-neck flask were put 2.0 g (4.9 mmol) of 4-(9-phenyl-9H-carbazol-3-yl)diphenylamine, 1.1 g (4.9 mmol) of 4-bromobiphenyl, and 2.0 g (20 mmol) of sodium tert-butoxide, and the air in the flask was replaced with nitrogen. To this mixture were added 50 mL of toluene and 0.30 mL of tri(tert-butyl)phosphine (a 10 wt % hexane solution).

Under reduced pressure, this mixture was stirred to be degassed. Then, 0.10 g of bis(dibenzylideneacetone)palladium(0) was added to this mixture. Next, this mixture was heated and stirred at 80° C. for 5 hours to be reacted. After the reaction, toluene was added to this reaction mixture. This suspension was suction filtered through Celite (produced by Wako Pure Chemical Industries, Ltd., Catalog No. 531-16855), alumina, and Florisil (produced by Wako Pure Chemical Industries, Ltd., Catalog No. 540-00135), and thus the filtrate was obtained. The resulting filtrate was washed with an aqueous solution of sodium carbonate and saturated brine in this order. The organic layer was dried by addition of magnesium sulfate thereto. Then, this mixture was suction filtered to remove the magnesium sulfate, and thus the filtrate was obtained.

The obtained filtrate was concentrated, and purified by silica gel column chromatography. The silica gel column chromatography was performed with a mixture solvent of toluene to hexane in a ratio of 1 to 9 as a developing solvent first, and then with a mixture solvent of toluene to hexane in a ratio of 3 to 7 as another developing solvent. The obtained fractions were concentrated to give a solid. Recrystallization of this solid from a mixed solvent of chloroform and hexane gave 2.3 g of a white powdered solid in 84% yield, which was the substance to be produced.

By a train sublimation method, 1.2 g of the obtained white solid was purified. Under reduced pressure of 7.0 Pa with a flow rate of argon at 3 mL/min, the sublimation purification was carried out at 280° C. for 20 hours. The amount and yield of the obtained solid were 1.1 g and 89%, respectively.

The compound obtained through the above Step 4 was measured by a nuclear magnetic resonance (NMR) method. The measurement data are given below. The measurement results indicate that 4-phenyl-4'-(9-phenyl-9H-carbazol-3-yl)triphenylamine (abbreviation: PCBA1BP) was obtained.

$^1$H NMR (CDCl$_6$, 300 MHz): δ (ppm)=7.05-7.20 (m, 7H), 7.28-7.78 (m, 21H), 8.34 (d, J=7.8 Hz, 1H), 8.57 (s, 1H).

This application is based on Japanese Patent Application serial No. 2009-291593 filed with the Japan Patent Office on Dec. 23, 2009, the entire contents of which are hereby incorporated by reference.

What is claimed is:

1. A heterocyclic compound including a structure represented by Formula (G1-1), (G1-1)

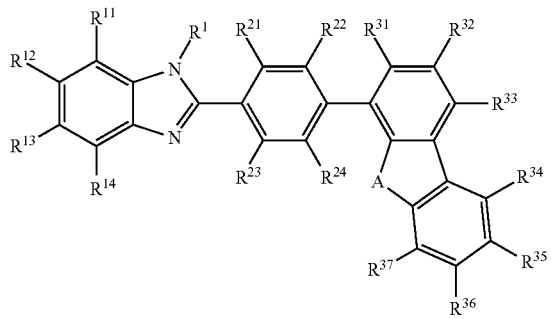

wherein A represents oxygen or sulfur, wherein $R^1$ represents an alkyl group having 1 to 4 carbon atoms or a substituted or unsubstituted aryl group having 6 to 13 carbon atoms, and wherein $R^{11}$ to $R^{14}$, $R^{21}$ to $R^{24}$, and $R^{31}$ to $R^{37}$ separately represent any of hydrogen, an alkyl group having 1 to 4 carbon atoms, and a substituted or unsubstituted aryl group having 6 to 13 carbon atoms.

2. A heterocyclic compound including a structure represented by Formula (G2-1),

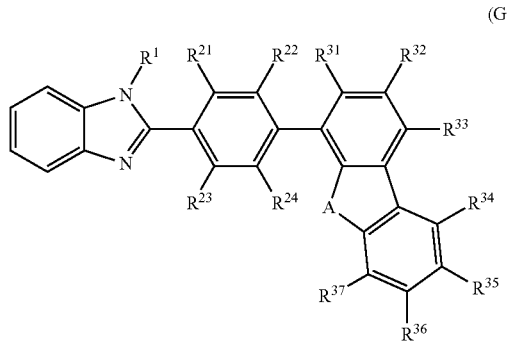

(G2-1)

wherein A represents oxygen or sulfur, wherein $R^1$ represents an alkyl group having 1 to 4 carbon atoms or a substituted or unsubstituted aryl group having 6 to 13 carbon atoms, and wherein $R^{21}$ to $R^{24}$ and $R^{31}$ to $R^{37}$ separately represent any of hydrogen, an alkyl group having 1 to 4 carbon atoms, and a substituted or unsubstituted aryl group having 6 to 13 carbon atoms.

3. A heterocyclic compound including a structure represented by Formula (G2-1),

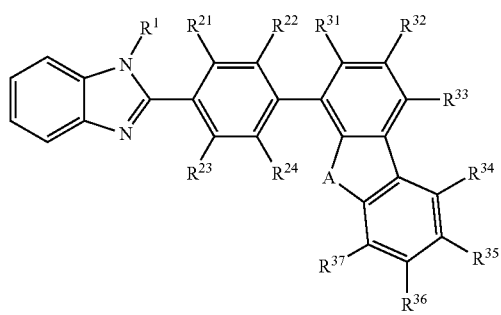

(G2-1)

wherein A represents oxygen or sulfur, wherein $R^1$ represents an alkyl group having 1 to 4 carbon atoms or a substituted or unsubstituted aryl group having 6 to 13 carbon atoms, wherein $R^{21}$ to $R^{24}$ separately represent any of hydrogen, an alkyl group having 1 to 4 carbon atoms, and a substituted or unsubstituted aryl group having 6 to 13 carbon atoms, and wherein $R^{31}$ to $R^{37}$ separately represent hydrogen or a substituted or unsubstituted aryl group having 6 to 13 carbon atoms.

4. A heterocyclic compound including a structure represented by Formula (G2-1),

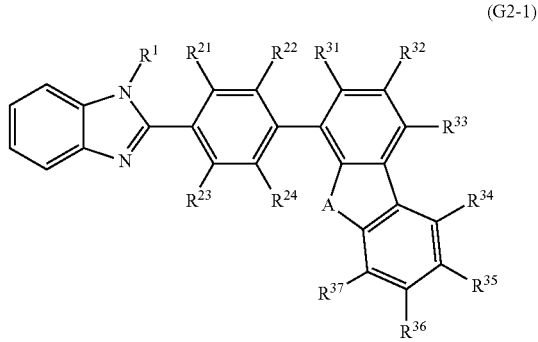

(G2-1)

wherein A represents oxygen or sulfur, wherein $R^1$ represents an alkyl group having 1 to 4 carbon atoms or a substituted or unsubstituted aryl group having 6 to 13 carbon atoms, wherein $R^{21}$ to $R^{24}$ separately represent any of hydrogen, an alkyl group having 1 to 4 carbon atoms, and a substituted or unsubstituted aryl group having 6 to 13 carbon atoms, wherein $R^{31}$ to $R^{37}$ separately represent hydrogen or a substituted or unsubstituted aryl group having 6 to 13 carbon atoms, and wherein at least one of $R^{31}$ to $R^{37}$ represents a substituted or unsubstituted aryl group having 6 to 13 carbon atoms.

5. A heterocyclic compound including a structure represented by Formula (G3-1),

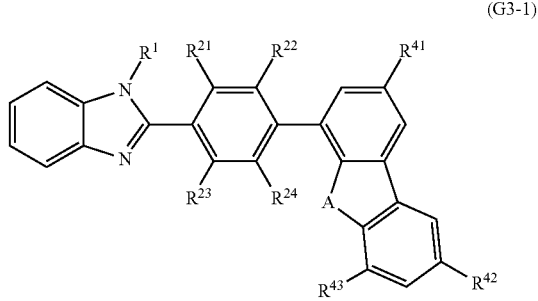

(G3-1)

wherein A represents oxygen or sulfur, wherein $R^1$ represents an alkyl group having 1 to 4 carbon atoms or a substituted or unsubstituted aryl group having 6 to 13 carbon atoms, wherein $R^{21}$ to $R^{24}$ separately represent any of hydrogen, an alkyl group having 1 to 4 carbon atoms, and a substituted or unsubstituted aryl group having 6 to 13 carbon atoms, wherein $R^{41}$ to $R^{43}$ separately represent hydrogen or a substituted or unsubstituted aryl group having 6 to 13 carbon atoms, and wherein at least one of $R^{41}$ to $R^{43}$ represents a substituted or unsubstituted aryl group having 6 to 13 carbon atoms.

6. A heterocyclic compound including a structure represented by Formula (G4-1),

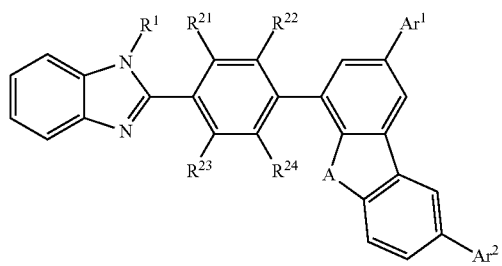

wherein A represents oxygen or sulfur,
wherein $R^1$ represents an alkyl group having 1 to 4 carbon atoms or a substituted or unsubstituted aryl group having 6 to 13 carbon atoms,
wherein $R^{21}$ to $R^{24}$ separately represent any of hydrogen, an alkyl group having 1 to 4 carbon atoms, and a substituted or unsubstituted aryl group having 6 to 13 carbon atoms, and
wherein $Ar^1$ and $Ar^2$ separately represent a substituted or unsubstituted aryl group having 6 to 13 carbon atoms.

7. A heterocyclic compound including a structure represented by Formula (G1-2),

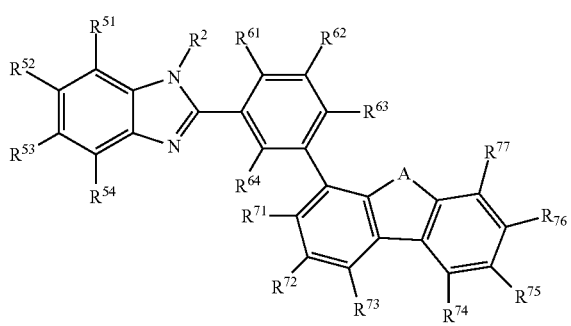

wherein A represents oxygen or sulfur,
wherein $R^2$ represents an alkyl group having 1 to 4 carbon atoms or a substituted or unsubstituted aryl group having 6 to 13 carbon atoms, and
wherein $R^{51}$ to $R^{54}$, $R^{61}$ to $R^{64}$, and $R^{71}$ to $R^{77}$ separately represent any of hydrogen, an alkyl group having 1 to 4 carbon atoms, and a substituted or unsubstituted aryl group having 6 to 13 carbon atoms.

8. A heterocyclic compound including a structure represented by Formula (G2-2),

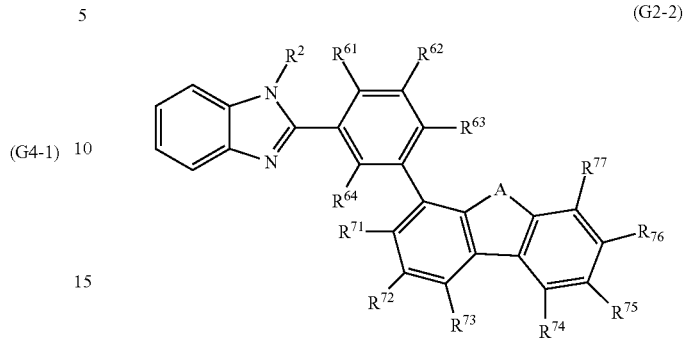

wherein A represents oxygen or sulfur,
wherein $R^2$ represents an alkyl group having 1 to 4 carbon atoms or a substituted or unsubstituted aryl group having 6 to 13 carbon atoms, and
wherein $R^{61}$ to $R^{64}$ and $R^{71}$ to $R^{77}$ separately represent any of hydrogen, an alkyl group having 1 to 4 carbon atoms, and a substituted or unsubstituted aryl group having 6 to 13 carbon atoms.

9. A heterocyclic compound including a structure represented by Formula (G2-2),

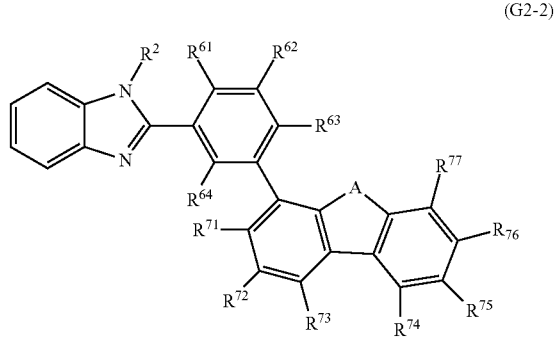

wherein A represents oxygen or sulfur,
wherein $R^2$ represents an alkyl group having 1 to 4 carbon atoms or a substituted or unsubstituted aryl group having 6 to 13 carbon atoms,
wherein $R^{61}$ to $R^{64}$ separately represent any of hydrogen, an alkyl group having 1 to 4 carbon atoms, and a substituted or unsubstituted aryl group having 6 to 13 carbon atoms, and
wherein $R^{71}$ to $R^{77}$ separately represent hydrogen or a substituted or unsubstituted aryl group having 6 to 13 carbon atoms.

10. A light-emitting element comprising the heterocyclic compound according to any one of claims 1 to 9 between a pair of electrodes.

11. A light-emitting element comprising a light-emitting layer between a pair of electrodes, wherein the light-emitting layer comprises a light-emitting substance and the heterocyclic compound according to any one of claims 1 to 9.

12. A light-emitting element comprising at least a light-emitting layer and an electron-transport layer between a pair of electrodes, wherein the electron-transport layer comprises the heterocyclic compound according to any one of claims 1 to 9.

13. A light-emitting device comprising the heterocyclic compound according to any one of claims 1 to 9.

14. An electronic device comprising the light-emitting device according to claim 13, wherein the electronic device is one selected from the group consisting of a television set, a computer, a cellular phone and a camera.

15. A lighting device comprising the light-emitting device according to claim 13, wherein the lighting device is one selected from the group consisting of a desk lamp and an indoor lighting device.

* * * * *